United States Patent
Hayashizaki et al.

(10) Patent No.: US 6,265,569 B1
(45) Date of Patent: Jul. 24, 2001

(54) 3'-DEOXYRIBONUCLEOTIDE DERIVATIVES

(75) Inventors: Yoshihide Hayashizaki, Ibaraki; Kaori Ozawa, Hyogo; Kazunari Fujio, Hyogo; Takumi Tanaka, Hyogo, all of (JP)

(73) Assignee: The Institute of Physical and Chemical Research (JP)

( * ) Notice: Subject to any disclaimer, the term of this patent is extended or adjusted under 35 U.S.C. 154(b) by 0 days.

(21) Appl. No.: 09/263,520

(22) Filed: Mar. 5, 1999

Related U.S. Application Data

(63) Continuation-in-part of application No. PCT/JP98/03038, filed on Jul. 6, 1998.

(30) Foreign Application Priority Data

Jul. 7, 1997 (JP) .................................................. 9-180879
Jun. 4, 1998 (JP) ................................................. 10-155774

(51) Int. Cl.$^7$ .................................................. C07H 19/00
(52) U.S. Cl. ..................... 536/26.26; 536/26.3; 536/26.6; 536/26.7; 536/26.8; 536/28.1; 536/28.4; 536/23.1; 536/24.3
(58) Field of Search ............................... 536/26.26, 26.3, 536/26.6, 26.7, 26.8, 28.1, 28.4, 23.1, 24.3

(56) References Cited

U.S. PATENT DOCUMENTS 5,047,519 * 9/1991 Hobbs, Jr. et al. ..................... 536/23
5,821,356 * 10/1998 Khan et al. ........................ 536/26.26
6,165,765 * 12/2000 Hong et al. ............................ 435/194

FOREIGN PATENT DOCUMENTS 4-320699    11/1992   (JP) .
08140700-A2 *  6/1996   (JP) .
10-158293    6/1998   (JP) .
WO-9902543-A1 *  1/1999   (WO) .

OTHER PUBLICATIONS

Nobuya et al. "Transcriptional sequencing: A method for DNA sequencing using RNA polymerase." Proc. Natl. Acad. Sci. vol. 95, pp 3455–3460, Mar. 1998.*

Mcewan, N.R. "Fluorescent labeling of oligonucleotides using terminal transferase." Biotechnol. Tech. (1997), 11(10), 727–728.*

Sasaki, N. et al "Transcriptional sequencing: A method for DNA sequencing using RNA polymerase", Proc. Natl. Acad. Sci. USA, vol. 95, (Mar. 1998), p. 3455–3460.

Axelrod, D. et al "Transcription from Bacteriophage T7 and SP6 RNA Polymerase Promoters in the Presence of 3'–Deoxyribonucleoside 5'–Triphosphate Chain Terminators", Biochemistry, vol. 24, (1985), p. 5716–5723.

* cited by examiner

*Primary Examiner*—Ralph Gitomer
*Assistant Examiner*—Devesh Khare
(74) *Attorney, Agent, or Firm*—Burns, Doane, Swecker & Mathis, L.L.P.

(57) ABSTRACT

Disclosed are 3'-deoxyribonucleotide derivatives represented by the following general formula [I]:

$$Q-V-(CH_2)_n-NH-R \qquad [I]$$

wherein Q represents a 3'-deoxyribonucleotide residue, n represents an integer not less than 4, V represents —C≡C— or —CH=CH—, and R represents a fluorescent group.

The above 3'-deoxyribonucleotide derivatives are derivatives with improved rates for incorporation using RNA polymerases, which are useful as terminators in the DNA sequence determination methods utilizing RNA polymerases.

21 Claims, 10 Drawing Sheets

3'-DEOXYRIBONUCLEOTIDE DERIVATIVES

CROSS-REFERENCE TO RELATED APPLICATIONS

This application is a continuation-in-art of application PCT/JP98/03038, filed Jul. 6, 1998. This application is incorporated by reference in its entirety herein.

TECHNICAL FIELD

The present invention relates to novel 3'-deoxyribonucleotide derivatives. More precisely, the present invention relates to 3'-deoxyribonucleotide derivatives useful as terminators used in methods for determining nucleotide sequences utilizing RNA polymerases.

BACKGROUND ART

Nucleotide sequence analysis of DNA is one of the basic techniques in molecular biology.

As methods for determining DNA sequences, there have been known two fundamental methods, i.e., the Maxam-Gilbert method (chemical degradation method) [Methods Enzymology, 65, 499–560 (1980)] and the Sanger method (dideoxy chain termination method) [Proc. Natl. Acad. Sci., USA, 74, 5463–5467 (1977)]. Among these, the dideoxy chain termination method is simpler and enables more quick sequencing in comparison with the chemical degradation method, and therefore it has been the mainstream of the DNA sequencing methods.

The basic principle of the dideoxy chain termination method is as follows.

First, a single-stranded DNA containing a DNA fragment of which nucleotide sequence is to be determined is prepared, and used as a template for the replication step. Then, a primer is annealed to a region of the DNA in the proximity of the inserted region of the DNA fragment, and a DNA complementary to the single-stranded DNA is synthesized with an enzyme called Klenow fragment. This synthesis is performed in the presence of the four kinds of naturally occurring 2'-deoxyribonucleotides and 2',3'-dideoxynucleotides labeled with radioactive isotopes, fluorescent dyes and the like and corresponding to the four kinds of nucleotides as chain terminators (terminators). The 2',3'-dideoxynucleotides are 2'-deoxyribonucleotides of which 3'-OH groups are replaced by H groups, and they may be the substrate for the Klenow fragment like the 2'-deoxyribonucleotides, but the DNA chain extension is terminated when the 2',3'-dideoxynucleotides are incorporated. As a result, various DNA chains having common 5'-ends but having various chain lengths are synthesized.

That is, the above reaction is performed by using the 2',3'-dideoxynucleotide compounds together with 2'-deoxyribonucleotides for all of the bases, adenine (A), guanine (G), cytosine (C), and thymine (T), and the products are subjected to electrophoresis. This enables reading of the order of the nucleotide sequence based on the sizes of the DNA fragments.

However, under the recent circumstance where total DNA sequence or even whole genomic genes of humans, animals and plants are determined as in, for example, the so-called human genome project, there have been pointed out problems of the above dideoxy chain termination method, for example, complexity of the operation procedure (for preparation of template single-stranded DNA and the like), difficulty of shortening the process time and the like.

As the method for determining DNA sequences, the method where products amplified by the polymerase chain reaction (PCR) method [Randall K. Saiki et al. Science, 239:487–491 (1988)] are sequenced without cloning them [the direct sequencing method, Corinne Wong et al. Nature, 330:384–386 (1988)] is also a useful method. This method does not require the library construction and screening, and is a quick method capable of simultaneously obtaining sequence information of many samples.

However, the above direct sequencing method suffers from two major problems. One is that primers and 2'-deoxyribonucleoside 5'-triphosphates (2'-dNTPs) not incorporated remain in the reaction system, and they inhibit the sequencing reaction. Therefore, in conventional methods, such primers and 2'-dNTPs must be removed from PCR products before sequencing. There are many methods for purification of PCR products such as purification by electrophoresis, ethanol precipitation, gel filtration, HPLC purification and the like [see, for example, Dorit R. L et al. Current Protocols in Molecular Biology, Vol. 11, John Wiley and Sons, New York, 15.2.1–15.2.11 (1991)]. However, these methods are complicated without exception.

The second problem is quick renaturation of PCR products. When the PCR products are renatured into a double-stranded DNA, they are no longer single-stranded templates, and annealing between primers and single-stranded templates is inhibited. As methods for minimizing the renaturation, there have been reported, for example, quenching after denaturation, biotilation of one primer and absorption of PCR products onto streptavidin-coated articles, use of exonuclease, asymmetric PCR and the like. They are disclosed in, for example, Barbara Bachmann et al., Nucleic Acid Res., 18:1309 1990. However, most of these methods are time-consuming and very laborious.

DNA sequencing methods by chain elongation utilizing RNA polymerases have been researched as one of the means which solve these problems. Among such DNA sequencing methods utilizing RNA polymerases, there has been known a method utilizing four kinds of naturally occurring nucleotides and labeled 3'-deoxynucleotides having radioisotopes such as $^{32}P$ as the label and corresponding to the four kinds of nucleotides as terminators [Biochemistry, 24, 5716–5723 (1985)].

However, because these labeled terminators contain radioactive isotopes as the label, they are not preferred from the viewpoints of safety for human bodies and waste disposal. Therefore, it is expected to use terminators having fluorescent labels in stead of radioisotopes.

As for the labeled terminators used for the dideoxy chain termination method mentioned above, there have been various reports, for example, the report of Sanger et al. [J. Mol. Biol., 143, 161–178 (1980)], the report of Smith et al. [Nucleic Acids Res., 13, 2399–2412 (1985)], the report of Plober et al. [Science, 238, 336–341 (1987)], the report of Connel et al. [BioTechniques, 5, 342–348 (1987)], the report of Lee et al. [Nucleic Acids Res., 20, 2471–2483 (1992)], PCT International Application Unexamined publication in Japanese (KOHYO) No. (Hei) 5-502371/1993, Japanese Patent Publication (KOKOKU) No. (Hei) 7-121239/1995 and the like. However, all of the methods mentioned in these reports are those utilizing DNA polymerases, and therefore they use 2',3'-dideoxyribonucleotides as the terminators, and do not refer fluorescence-labeled 3'-deoxyribonucleotides at all.

Japanese Patent Publication No. (Hei) 8-5908/1996 mentions various labeled 2',3'-dideoxyribonucleotides, labeled 2'-deoxyribonucleotides, labeled 3'-deoxyribonucleotides and labeled ribonucleotides. However, as for the labeled 3'-deoxyribonucleotides, though they are disclosed as compounds falling within the scope of the general formula mentioned in the claims, they are not specifically exemplified as working examples and their synthesis is not verified. Therefore, they are considered still uncompleted. In addition, this patent document does not mention examples of actual use of the nucleotide derivatives for DNA sequencing at all.

On the other hand, it has been known that the incorporation of 2'-deoxyribonucleotides by DNA polymerase during DNA synthesis shows fluctuation depending on a base group each nucleotide has. Similar tendency is expected for labeled nucleotide derivatives, and fluctuation of the incorporation by DNA polymerase depending on differences between the labels is also expected. In spite of this, the above Japanese Patent Publication No. (Hei) 8-5908/1996 did not evaluate the incorporation of the disclosed derivatives by DNA polymerase at all. Labeled 3'-deoxyribonucleotides were of course not evaluated, since such compounds themselves were not synthesized.

The situation explained above is for the DNA sequencing methods using DNA polymerases, and it has not been known yet what kind of tendency would be observed for DNA sequencing methods using RNA polymerases. That is, there has not been any substantial knowledge about a difference in the incorporation efficiency among ribonucleotides resulting from a base group difference and a difference in the incorporation efficiency of labeled 3'-deoxyribonucleotides as well as the influence of these differences on DNA sequencing methods. In the fields requiring such an exquisite technique as DNA sequencing, fluorescence-labeled compounds and fluorescence-labeled 3'-deoxyribonucleotides are used for the dideoxy chain termination method which imposes the severe requirement that the materials must not inhibit the activity of RNA polymerase. Therefore, it is extremely difficult to estimate fluorescence-labeled terminators useful for the chain termination method using RNA polymerases from known labeled terminators such as those mentioned above based on structural correlation between DNA polymerases and RNA polymerases and the like.

Under these circumstances explained above, the present inventors previously developed various fluorescence-labeled 3'-deoxyribonucleotide derivatives useful as the terminators for the method of determining nucleotide sequences of nucleic acids utilizing RNA polymerases, and filed a patent application therefor (Japanese Patent Application No. (Hei) 8-227904/1996).

Thereafter, those fluorescence-labeled 3'-deoxyribonucleotide derivatives were actually used in methods for determining nucleotide sequences of nucleic acids utilizing RNA polymerases, and as a result nucleotide sequences of template DNA could be determined. However, even though the reason has not been clear, those fluorescence-labeled 3'-deoxyribonucleotide derivatives could not be incorporated by RNA polymerases with an efficiency sufficient for practical use in methods for determining DNA sequences. Therefore, in order to enable practical use of the DNA sequence determination methods utilizing RNA polymerases, it has been desired to provide fluorescence-labeled 3'-deoxyribonucleotide derivatives with improved incorporation rates by RNA polymerases.

Accordingly, an object of the present invention is to provide 3'-deoxyribonucleotide derivatives with improved incorporation rates by RNA polymerases, which are useful as terminators in the DNA sequence determination methods utilizing RNA polymerases.

SUMMARY OF THE INVENTION

The present invention relates to 3'-deoxyribonucleotide derivatives represented by the following general formula [I]:

$$Q-V-(CH_2)_n-NH-R \qquad [I]$$

In the formula, Q represents a 3'-deoxyribonucleotide residue, n represents an integer not less than 4, V represents —C≡C— or —CH=CH—, and R represents a fluorescent group.

The present inventors conducted various studies to achieve the above object. As a result, it was found that the fluorescence-labeled 3'-deoxyribonucleotide derivatives represented by the above general formula [I], that is, the fluorescence-labeled 3'-deoxyribonucleotide derivative having the number of n not less than 4 in the methylene chain represented by —(CH$_2$)$_n$— and comprising a fluorescent group represented by R are highly safe for human bodies, environment and the like, and detectable with high sensitivity, and can be a substrate of RNA polymerases, and that when they are used as the terminators in the DNA sequence determination methods utilizing RNA polymerases, they exhibit high incorporation rates by RNA polymerases, and thus completed the present invention.

DESCRIPTION OF THE PREFERRED EMBODIMENTS

Figure 1:
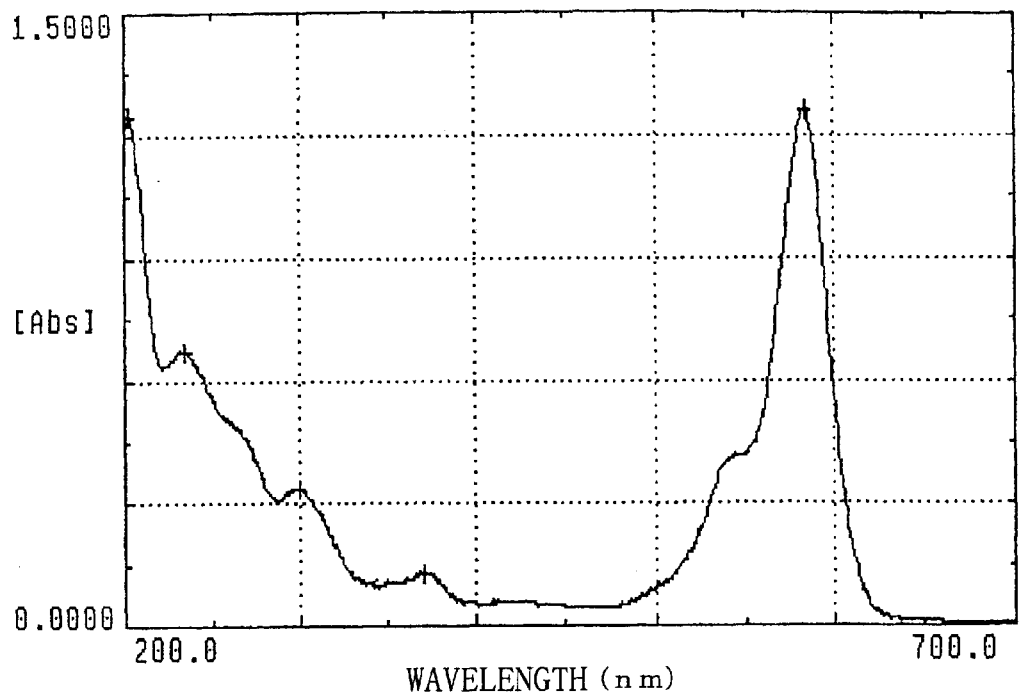
FIG. 1 shows the result of UV-visible region spectrophotometry of the carboxyrhodamine-X-labeled 3'-deoxycytidine-5'-triphosphate (a compound of the general formula [I] where V is —C≡C— and n=3) obtained in Reference Example 6.

The 3'-deoxyribonucleotide derivatives represented by the general formula [I] of the present invention are composed of three structural components:

(a) 3'-deoxyribonucleotide residue: Q,
(b) linker of the general formula [VI]:

 [VI]

wherein V and n have the same meanings as defined above, and (c) fluorescent group.

As the 3'-deoxyribonucleotide residue represented by Q, 7-deazapurine nucleotide residues represented by the following general formulae [II] and [III], and pyrimidine nucleotide residues represented by the following general formulae [IV] and [V] can be mentioned.

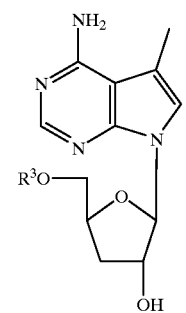

[II]

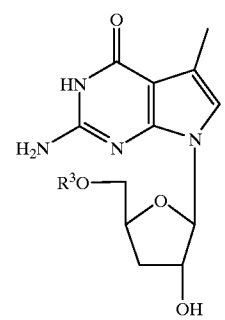

[III]

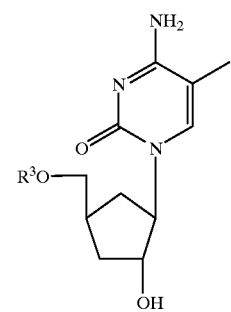

[IV]

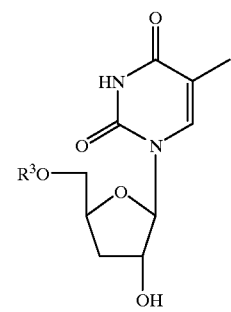

[V]

In above general formulae [II]–[V], $R_3$ represents —$PO_3H_2$, —$P_2O_6H_3$, —$P_3O_9H_4$ or a salt thereof. Preferred examples of the salt include, for example, alkali metal salts such as sodium salts, potassium salts and lithium salts, alkaline earth metal salts such as barium salts, ammonium salts such as triethylammonium salts, organic amine salts such as pyridine salts and the like.

The linker represented by the above general formula [VI] is a linker for binding the 3'-deoxyribonucleotide residue represented by Q and the fluorescent group.

That is, one of the carbon atoms forming double bond or triple bond in the linker is bonded to any of the 3'-deoxyribonucleotide residues represented by Q at 5-position for the pyrimidine nucleotide residues, or at 7-position for the 7-deazapurine nucleotide residues, respectively, and the —NH— group of the linker is bonded to a carboxyl group of the fluorescent dye group, so that a compound which have the 3'-deoxyribonucleotide residue and the fluorescent dye group is formed.

In the linker represented by the general formula [VI], examples of the methylene chain where n is not less than 4 include, for example, the methylene chain where n is 4–15, more specifically, a tetramethylene group, a pentamethylene group, a hexamethylenegroup, a heptamethylenegroup, an octamethylene group, a nonamethylene group, a decamethylene group and the like. From the viewpoint of improvement of incorporation rate by RNA polymerases, n should be an integer not less than 4, preferably n is an integer of 4–10, more preferably n is an integer of 4–8, particularly preferably n is 4 or 6.

The fluorescent group represented by R may be directly bound to the —NH— group, or bound to the —NH— group through a linker. The fluorescent group is not particularly limited, and may be suitably selected in view of fluorescence intensity, wavelength of fluorescence, easiness of incorporation by RNA polymerases and the like. However, the fluorescent group is preferably a fluorescent dye generating detectable luminescence emission subsequent to stimulation by energy absorption from a suitable energy source such as argon laser.

Examples of the fluorescent group R include, for example, groups represented by the following general formula [VII]. The fluorescent groups represented by the general formula [VII] are fluorescent dye groups generating detectable luminescence emission subsequent to stimulation by energy absorption from a suitable energy source such as argon laser.

[VII]

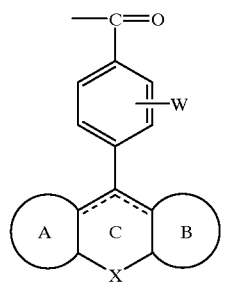

In the formula, W represents carboxyl group, X represents —O—, —S—, —NR'— where R' represents hydrogen atom, a lower alkyl group, an aralkyl group or an aryl group, or —CH$_2$—, one of the ring A and the ring B represents

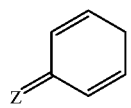

and the other one represents

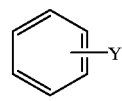

where Z represents O or =N$^+$R$_1$R$_2$, and Y represents OH or —NR$_1$R$_2$ where R$_1$ and R$_2$ each independently represent hydrogen atom or a lower alkyl group, or both of R$_1$ and R$_2$ represent a trimethylene group (i.e., R$_1$ and R$_2$ represent two trimethylene groups, of which other end is bonded to either one of the carbon atoms next to the nitrogen atom to which the trimethylene group is bonded), the broken line — — — — — — in the ring C:

represents a bond present at a position decided by the structures of the ring A and the ring B, and the rings A, B and C and the benzene ring having w may optionally have one or more additional substituents.

The lower alkyl group represented by R' in —NR'— for X in the general formula [VII] may be linear, branched or cyclic, and examples thereof include, for example, alkyl groups having 1–6 carbon atoms such as, specifically, a methyl group, an ethyl group, an n-propyl group, an isopropyl group, an n-butyl group, an isobutyl group, a sec-butyl group, a pentyl group, an isopentyl group, a tert-pentyl group, a 1-methylpentyl group, an n-hexyl group, an isohexyl group, a cyclopropyl group, a cyclopentyl group, a cyclohexyl group and the like. Examples of the aralkyl group represented by R' include, for example, aralkyl groups having 7–20 carbon atoms such as, specifically, a benzyl group, a phenethyl group, a phenylpropyl group, a methylbenzyl group, a methylphenethyl group, an ethylbenzyl group, a naphthylmethyl group, a naphthylethyl group and the like, and examples of the aryl group represented by the same include, for example, a phenyl group, a tolyl group, a xylyl group, a naphthyl group and the like.

The lower alkyl group represented by R$_1$ or R$_2$ in =N$^+$R$_1$R$_2$ represented by Z or in —NR$_1$R$_2$ represented by Y in the general formula [VII] may be linear, branched or cyclic, and examples thereof include, for example, alkyl groups having 1–6 carbon atoms such as, specifically, a methyl group, an ethyl group, an n-propyl group, an isopropyl group, an n-butyl group, an isobutyl group, a sec-butyl group, a pentyl group, an isopentyl group, a tert-pentyl group, a 1-methylpentyl group, an n-hexyl group, an isohexyl group, a cyclopropyl group, a cyclopentyl group, a cyclohexyl group and the like.

In the above general formula [VII], when the carboxyl group represented by W is bound at such a position as represented in the following general formula [VIII]:

[VIII]

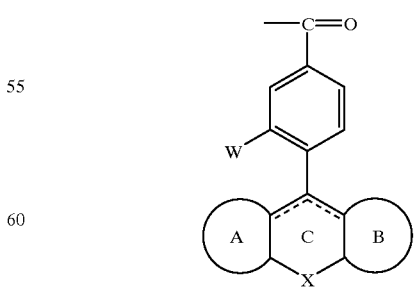

the portion of the fluorescent dye group in the 3'-deoxyribonucleotide derivatives of the present invention can take either of the following structures:

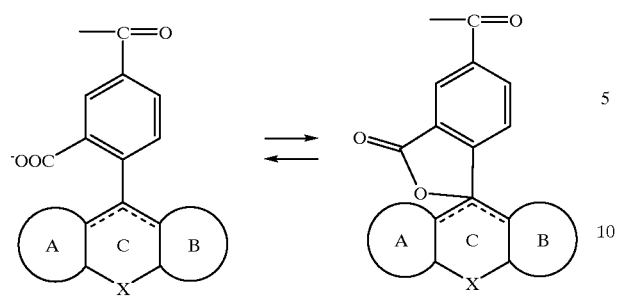

The carboxyl group may form a salt, for example, an alkali metal salt such as a sodium salt, a potassium salt and a lithium salt, an alkaline earth metal salt such as a barium salt, an ammonium salt such as a triethylammonium salt, an organic amine salt such as a pyridine salt or the like.

As an example of the compounds of the above general formula [VII] where, in the rings A and B, Z represents =$N^+R_1R_2$, and Y represents —$NR_1R_2$ where both of $R_1$ and $R_2$ represent a trimethylene group of which other end is bonded to either one of the carbon atoms next to the nitrogen atom to which the trimethylene group is bonded, a compound represented by the following formula can be mentioned:

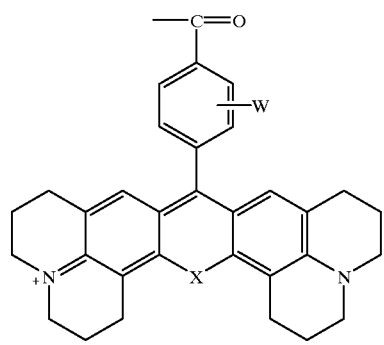

In above general formula [VII], the broken line — — — — — — in the ring C:

represents a bond present at a position decided by the structures of the ring A and the ring B. More specifically, it can be exemplified as follows.

That is, when the ring A is

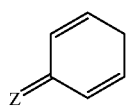

the bonding configuration of the ring C will be as follows:

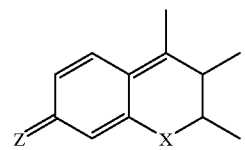

When the ring B is

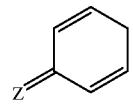

the bonding configuration of the ring C will be as follows:

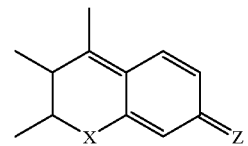

Further, when X is —NH—, the ring A (or the ring B) and the ring C can take either of the following configurations:

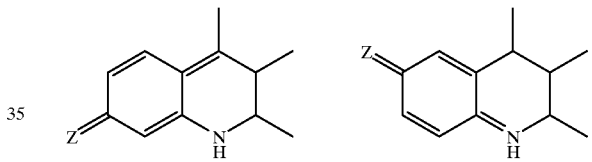

The rings A, B and C and the benzene ring having W may optionally have one or more additional substituents, and examples of such substituents include, for example, alkyl groups, alkoxy groups, halogen atoms and the like.

The alkyl groups may be linear, branched or cyclic, and may have a double bond, and examples thereof include, for example, alkyl groups having 1–20 carbon atoms, preferably alkyl groups having 1–6 carbon atoms. Specific examples thereof include, for example, a methyl group, an ethyl group, an n-propyl group, an isopropyl group, an n-butyl group, an isobutyl group, a sec-butyl group, a pentyl group, an isopentyl group, a tert-pentyl group, a 1-methylpentyl group, an n-hexyl group, an isohexyl group, a cyclopropyl group, a cyclopentyl group, a cyclohexyl group and the like. The alkoxy groups are preferably, for example, a lower alkoxy group, for example, lower alkoxy groups having 1–6 carbon atoms. Specific examples thereof are, for example, a methoxy group, an ethoxy group, an n-propoxy group, an isopropoxy group, an n-butoxy group, a pentyloxy group, an isopentyloxy group, a tert-pentyloxy group, a 1-methylpentyloxy group, an n-hexyloxy group, an isohexyloxy group and the like. Examples of the halogen atoms include fluorine, chlorine, bromine, iodine and the like.

Preferred specific examples of the fluorescent dye group represented by the above general formula [VII] include, for example, those derived from fluorescent dyes such as 5- or 6-carboxytetramethylrhodamine (abbreviated as TMR hereinafter), 5- or 6-carboxyrhodamine-X (abbreviated as XR hereinafter), 5- or 6-carboxyrhodamine-6G (abbreviated as R6G hereinafter), 5- or 6-carboxyrhodamine-110 (abbreviated as R110 hereinafter), 5- or 6-carboxyfluorescein, 5- or 6-carboxy-2',7'-dichlorofluorescein, 5- or 6-carboxy-2',4',5',7'-tetrachlorofluorescein, 5- or 6-carboxy-4,7-dichloro-2',7'-dimethoxyfluorescein, 5- or 6-carboxy-4,7,4',5'-tetrachloro-2',7'-dimethoxyfluorescein, 5- or 6-carboxy-4',5'-dichloro-2',7'-dimethoxyfluorescein, 5- or 6-carboxy-4A,7-dichloro-1',2',7',8'-dibenzofluorescein, 5- or 6-carboxy-4, 7-dichloro-1',2',7',8'-dibenzofluorescein and the like.

The 3'-deoxyribonucleotide derivatives of the present invention represented by general formula [I] can be synthesized easily, for example, according to the following synthesis schemes.

In the following synthesis schemes, $R_4$ represents a fluorescent dye group such as those mentioned above. Authorized nomenclatures for the abbreviations used in the following synthesis schemes are as follows.

CAN: cerium (IV) diammonium nitrate,
AcOH: acetic acid,
NPETFA: 5-trifluoroacetamido-1-pentyne,
NHETFA: 6-trifluoroacetamido-1-hexyne,
NOTFA: 8-trifluoroacetamido-1-octyne,
$Et_3N$: triethylamine,
$(Ph_3P)_4Pd$: tetrakis(triphenylphosphine)palladium (0),
DMF: N,N-dimethylformamide,
NHTfa: trifluoroacetamide
$(EtO)_3PO$: triethyl phosphate,
Tris(TBA)PP: tris(tri-n-butylammonium)pyrophosphate,
TEAB: triethylammonium hydrogencarbonate buffer,
TBDMSCl: tert-butyldimethylsilyl chloride,
THF: tetrahydrofuran,
TCDI: 1,1'-thiocarbonyldiimidazole,
n-$Bu_3$SnH: tri-n-butyltin hydride,
AIBN: 2,2'-azobis(isobutyronitrile),
pyr.: pyridine,
n-$Bu_4$NF: tetrabutylammonium fluoride,
$Ac_2O$: acetic anhydride,
MeOH: methanol,
NIS: N-iodosuccinimide,
STC: 4-thiocresol,
HMPA: hexamethylphosphoramide,
MCPBA: m-chloroperbenzoic acid,
$R_4$—OSu: succinimidyl ester of fluorescent dye group.

(1) Synthesis of fluorescence-labeled 3'-deoxyuridine 5'-triphosphates (compounds of the general formula [I] where V is —C≡C— and n=4)

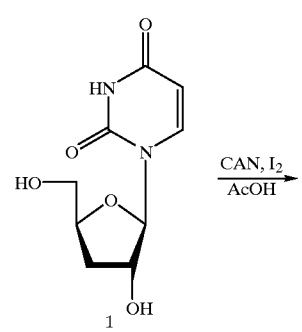

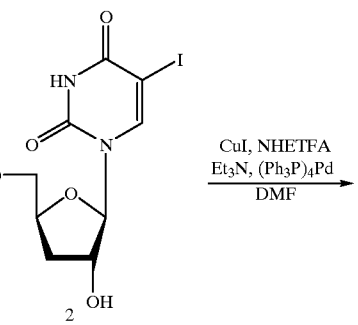

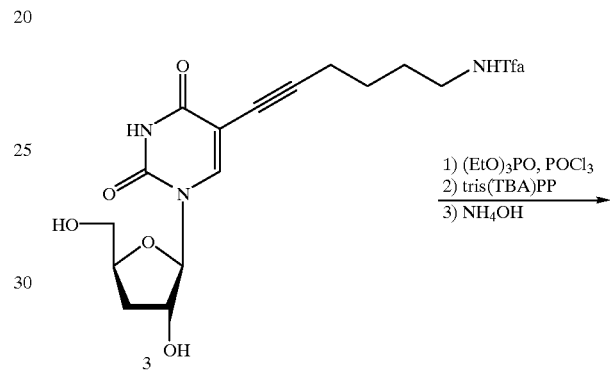

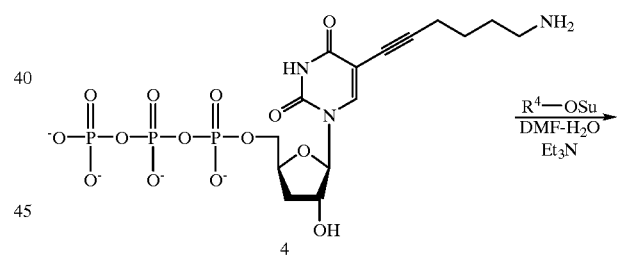

(2) Synthesis of fluorescence-labeled 3'-deoxycytidine 5'-triphosphates (compounds of the general formula [I] where V is —C≡C— and n=4)

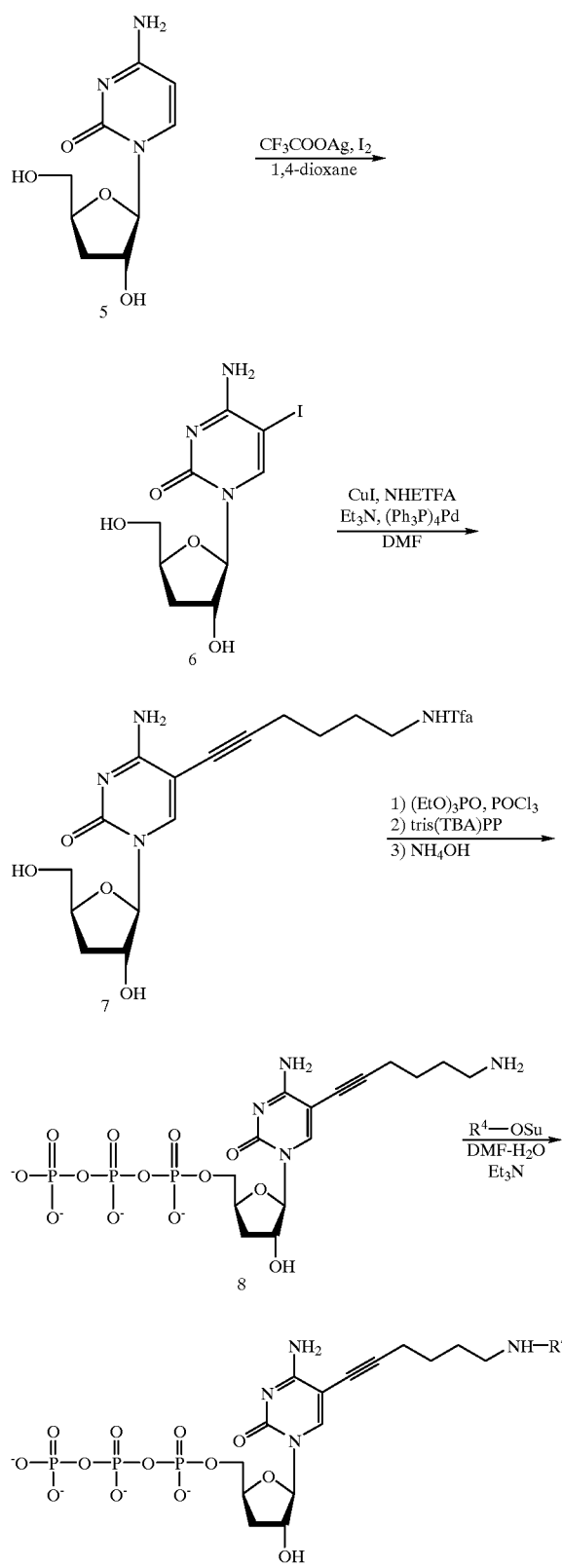
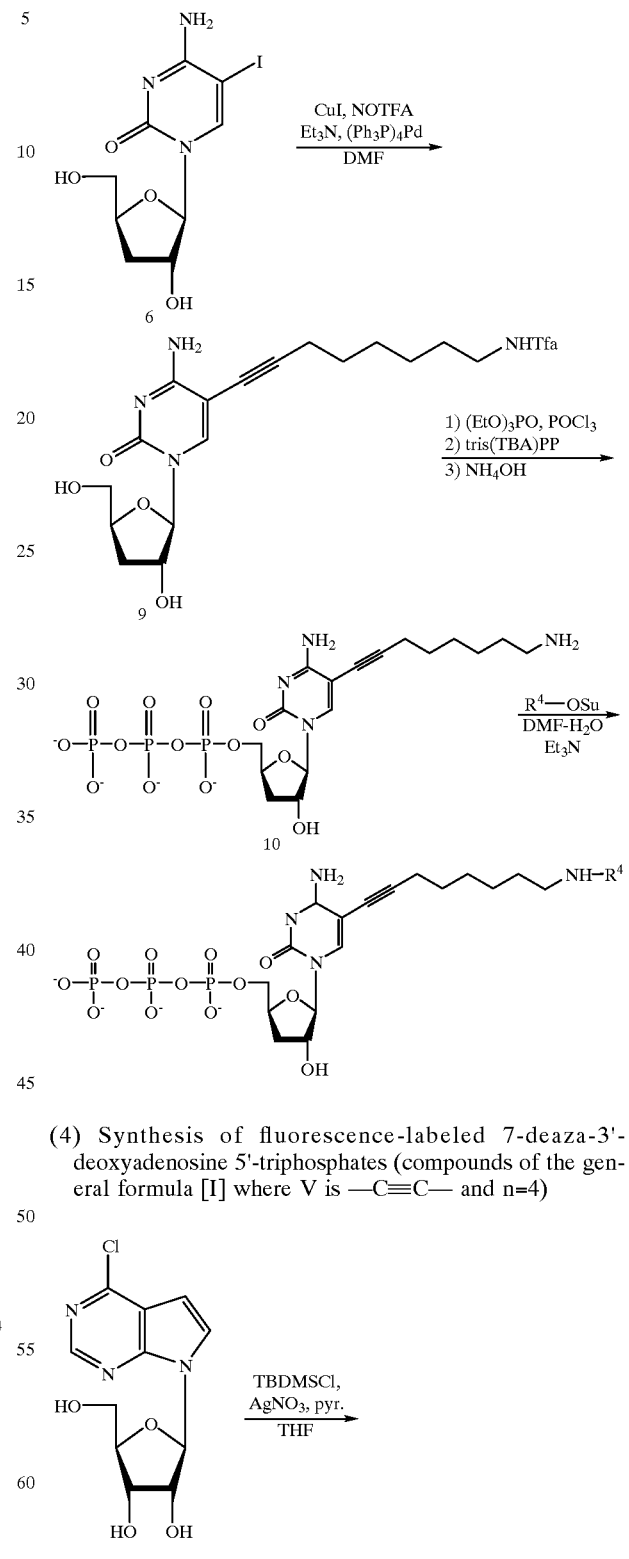
(3) Synthesis of fluorescence-labeled 3'-deoxycytidine 5'-triphosphates (compounds of the general formula [I] where v is —C≡C— and n=6)
(4) Synthesis of fluorescence-labeled 7-deaza-3'-deoxyadenosine 5'-triphosphates (compounds of the general formula [I] where V is —C≡C— and n=4)

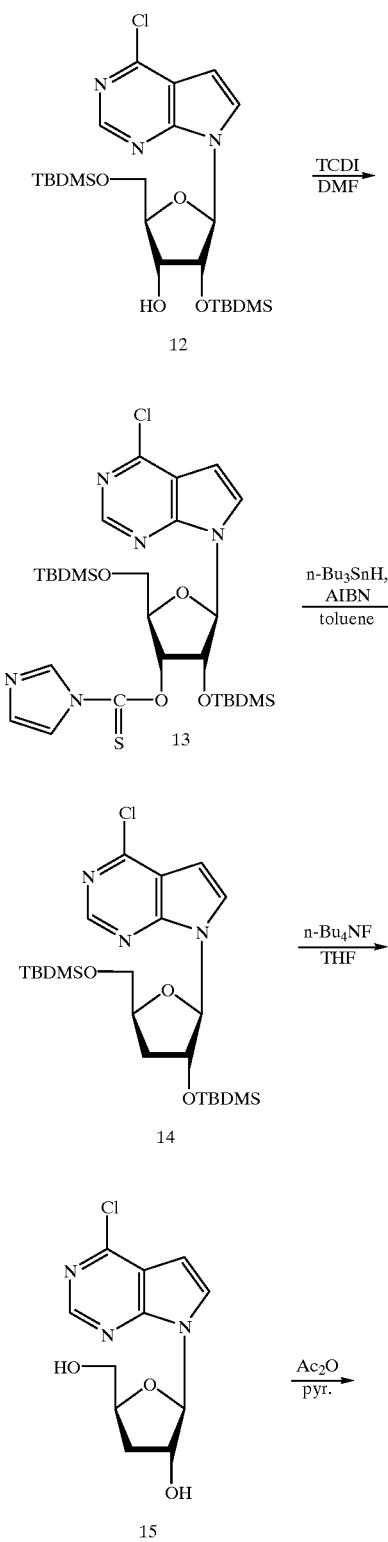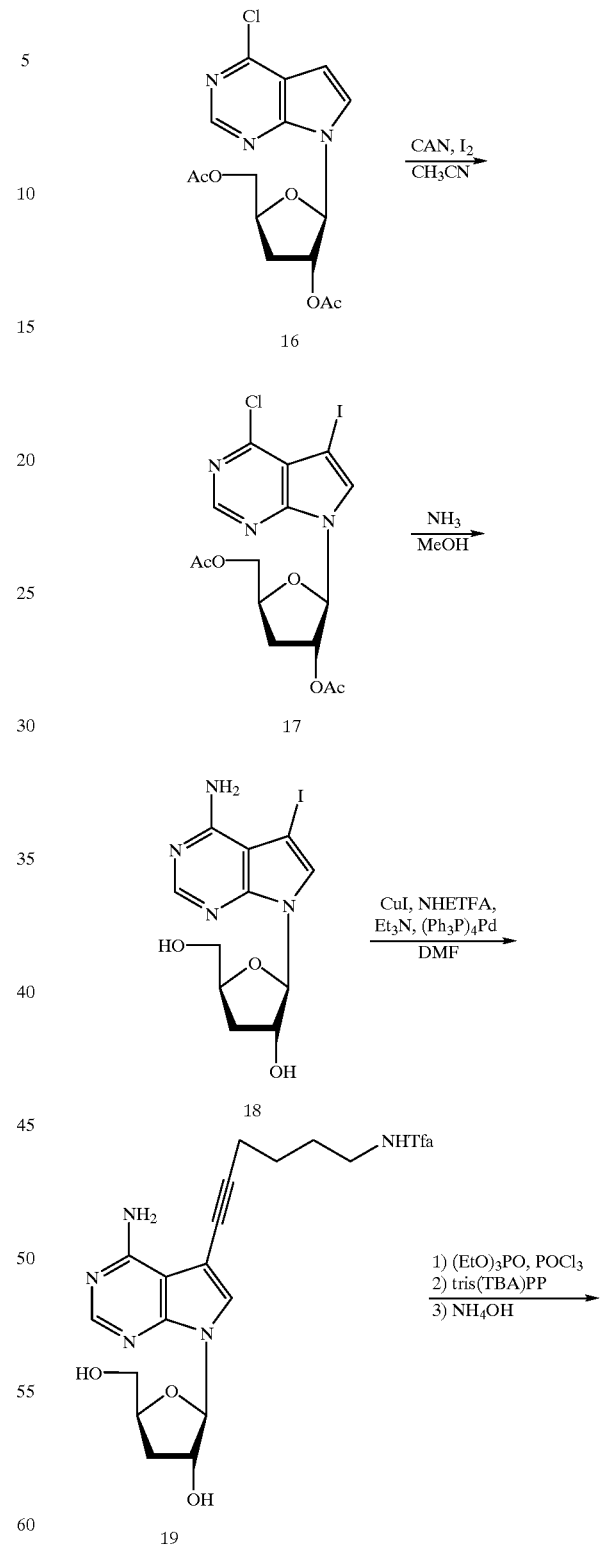

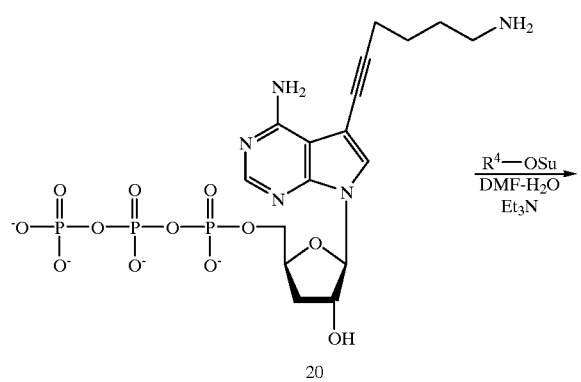
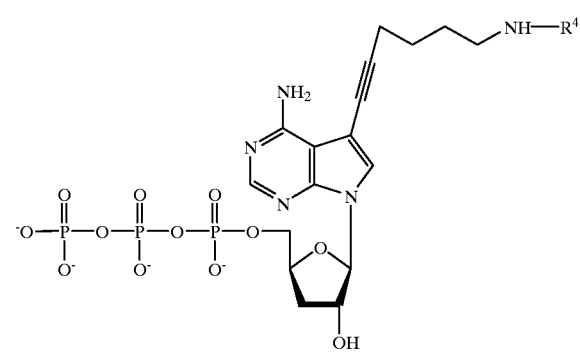
(5) Synthesis of fluorescence-labeled 7-deaza-3'-deoxyadenosine 5'-triphosphates (compounds of the general formula [I] where V is —C≡C— and n=6)
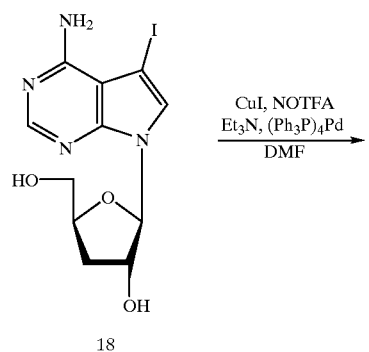
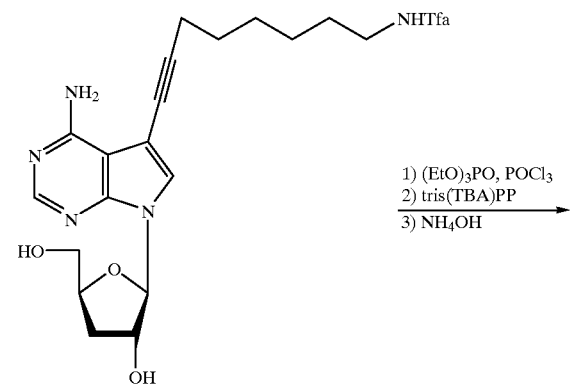
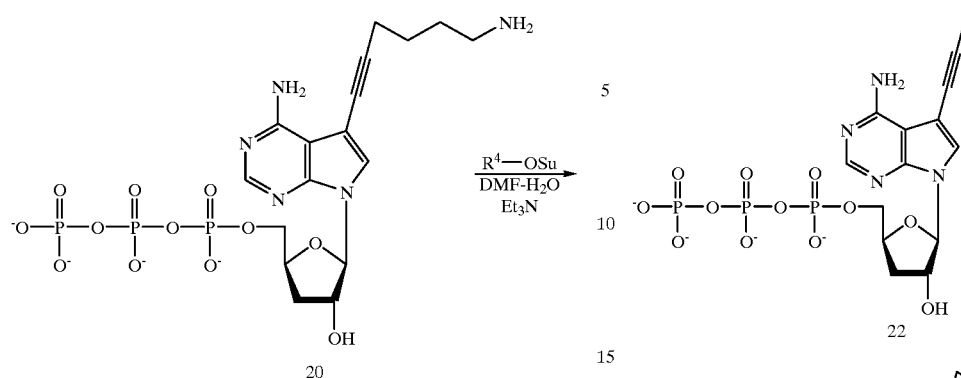
(6) Synthesis of fluorescence-labeled 7-deaza-3'-deoxyguanosine 5'-triphosphate (compounds of the general formula [I] where V is —C≡C— and n=4)
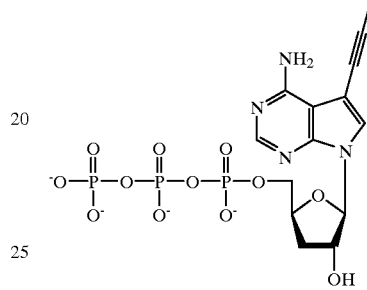
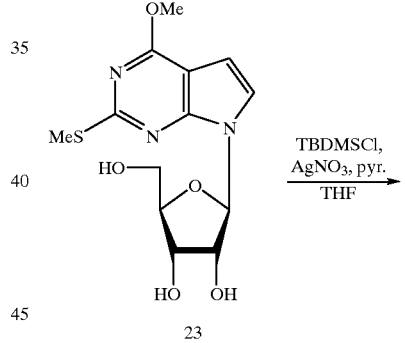
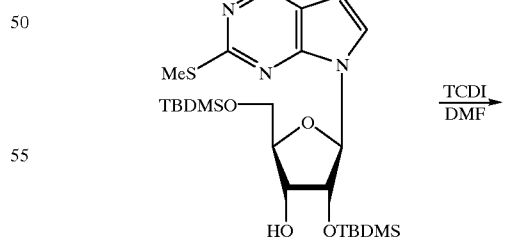

19
-continued
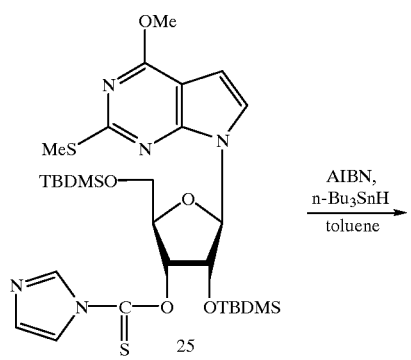
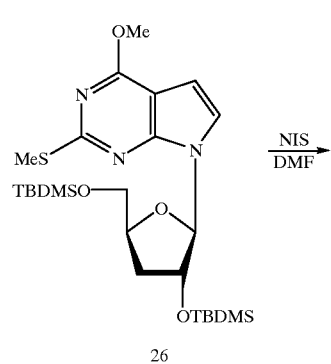
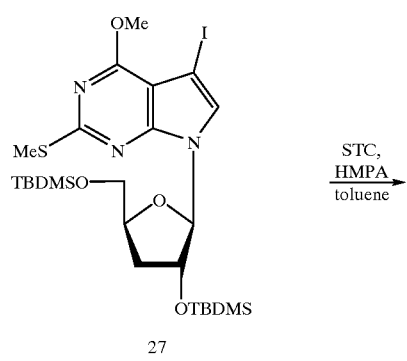
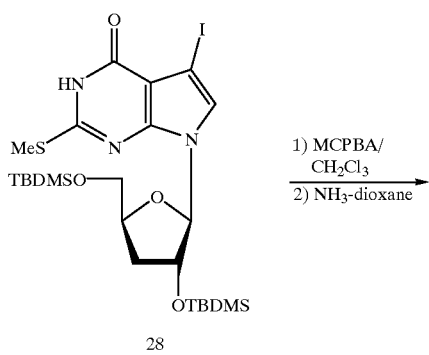
20
-continued
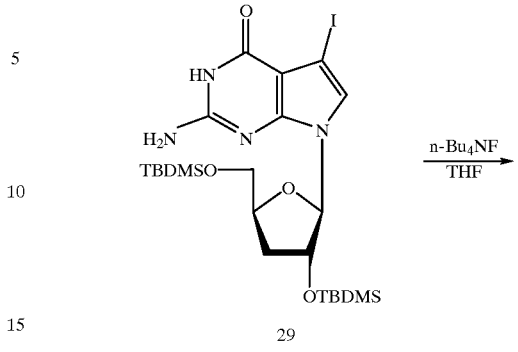
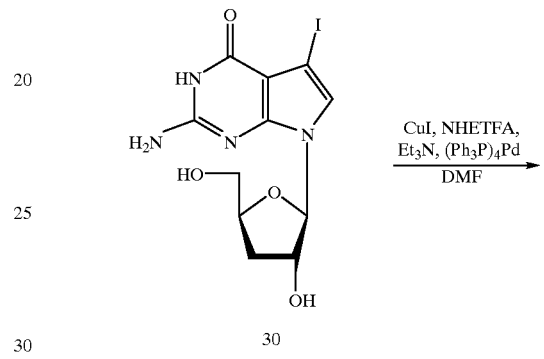
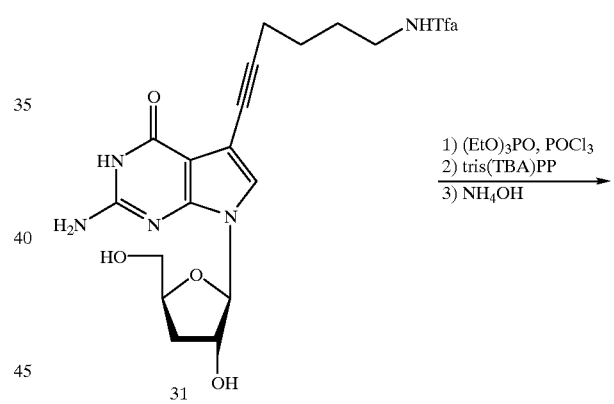
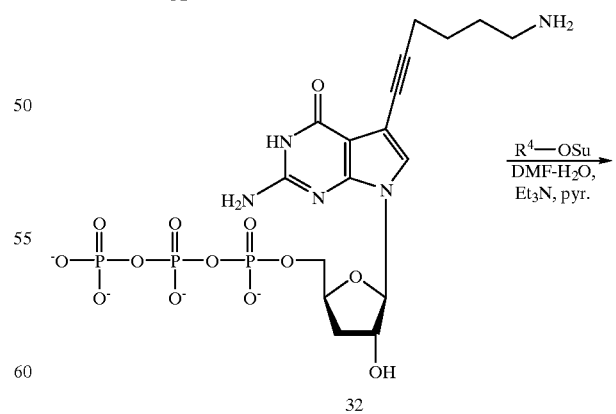

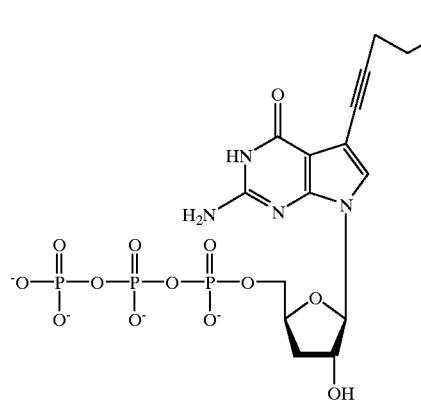

(7) Synthesis of fluorescence-labeled 3'-deoxyuridine 5'-triphosphates (compounds of the general formula [I] where V is —CH≡CH— and n=4)

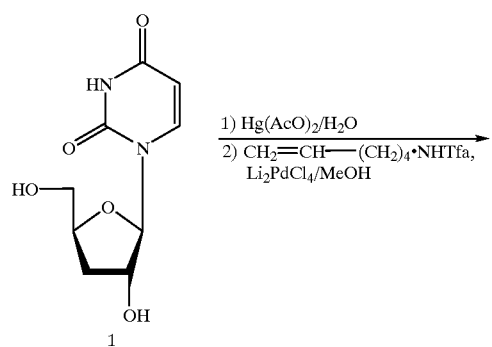

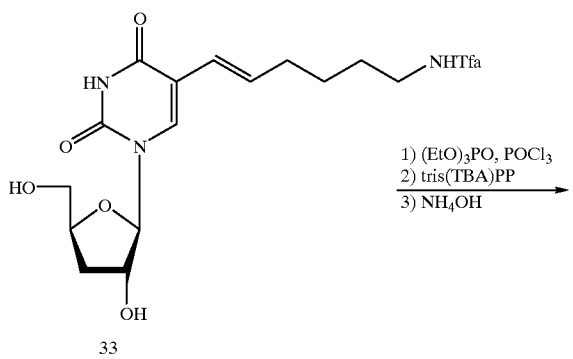

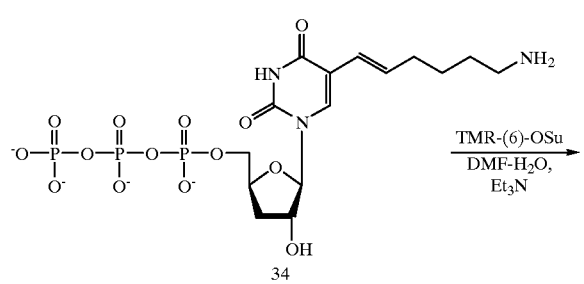

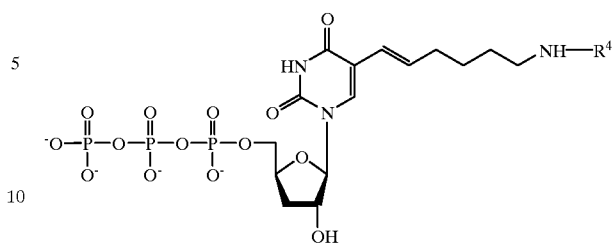

(8) Synthesis of fluorescence-labeled 3'-deoxyuridine 5'-triphosphates (compounds of the general formula [I] where V is —CH=CH— and n=4)

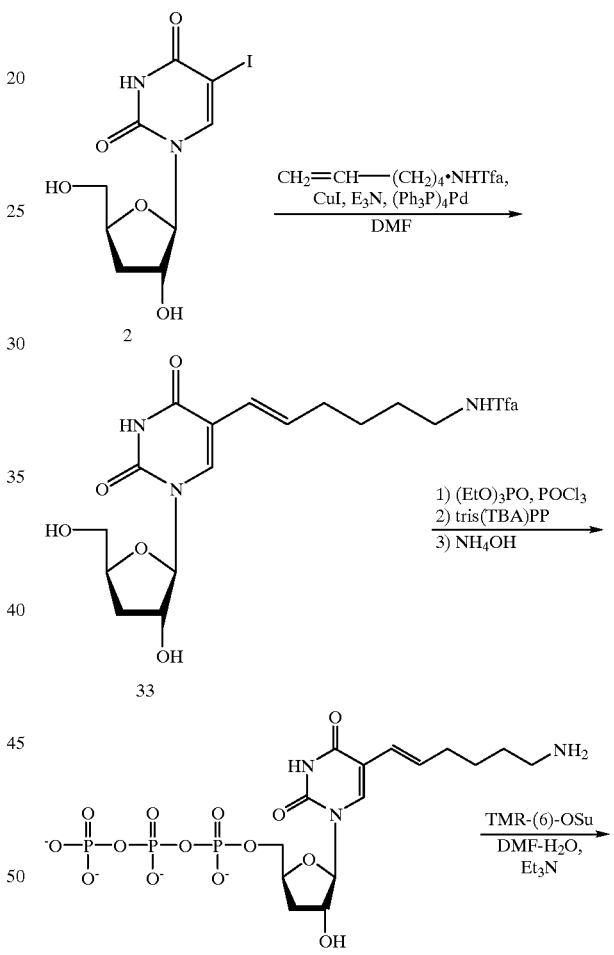

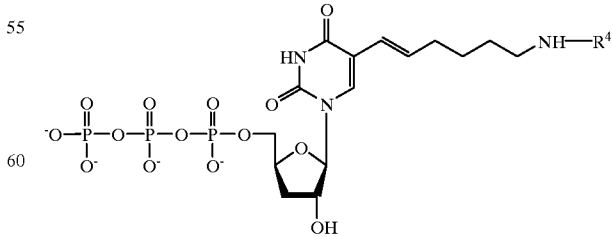

(9) Synthesis of fluorescence-labeled 7-deaza-3'-deoxycytidine 5'-triphosphates (compounds of the general formula [I] where V is —CH=CH— and n=4)

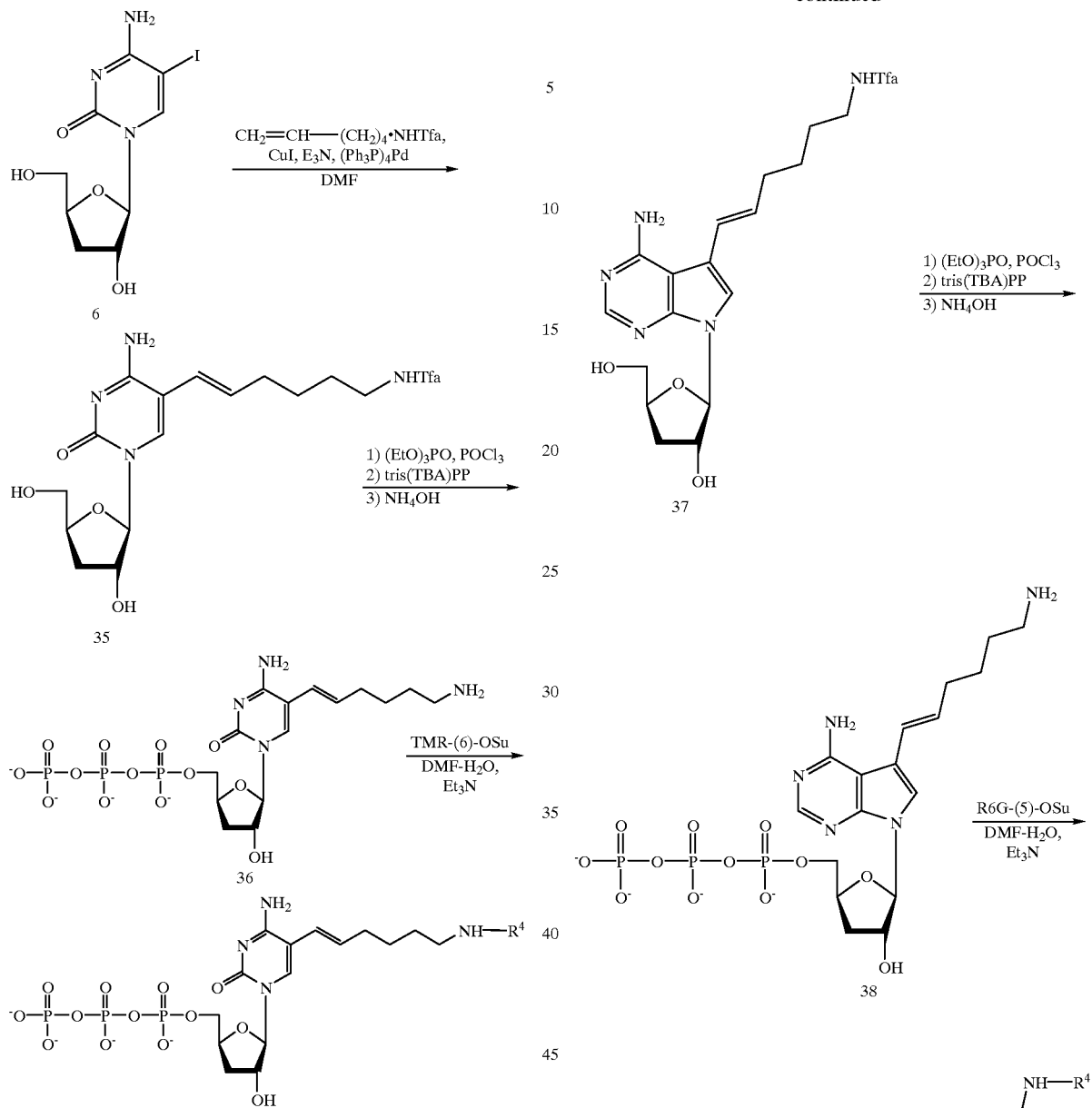
(10) Synthesis of fluorescence-labeled 7-deaza-3'-deoxyadenosine 5'-triphosphates (compounds of the general formula [I] where V is —CH=CH— and n=4)
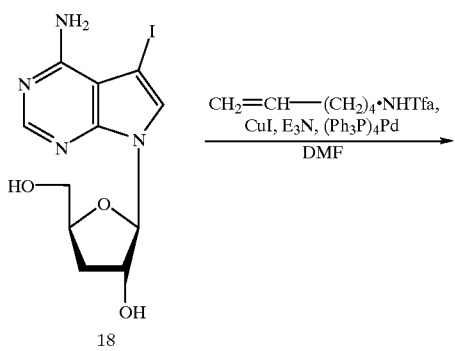
(11) Synthesis of fluorescence-labeled 7-deaza-3'-deoxyguanosine 5'-triphosphates (compounds of the general formula [I] where V is —CH=CH— and n=4)
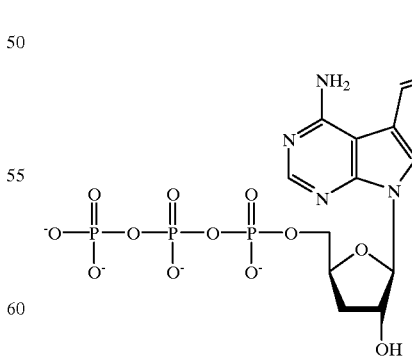

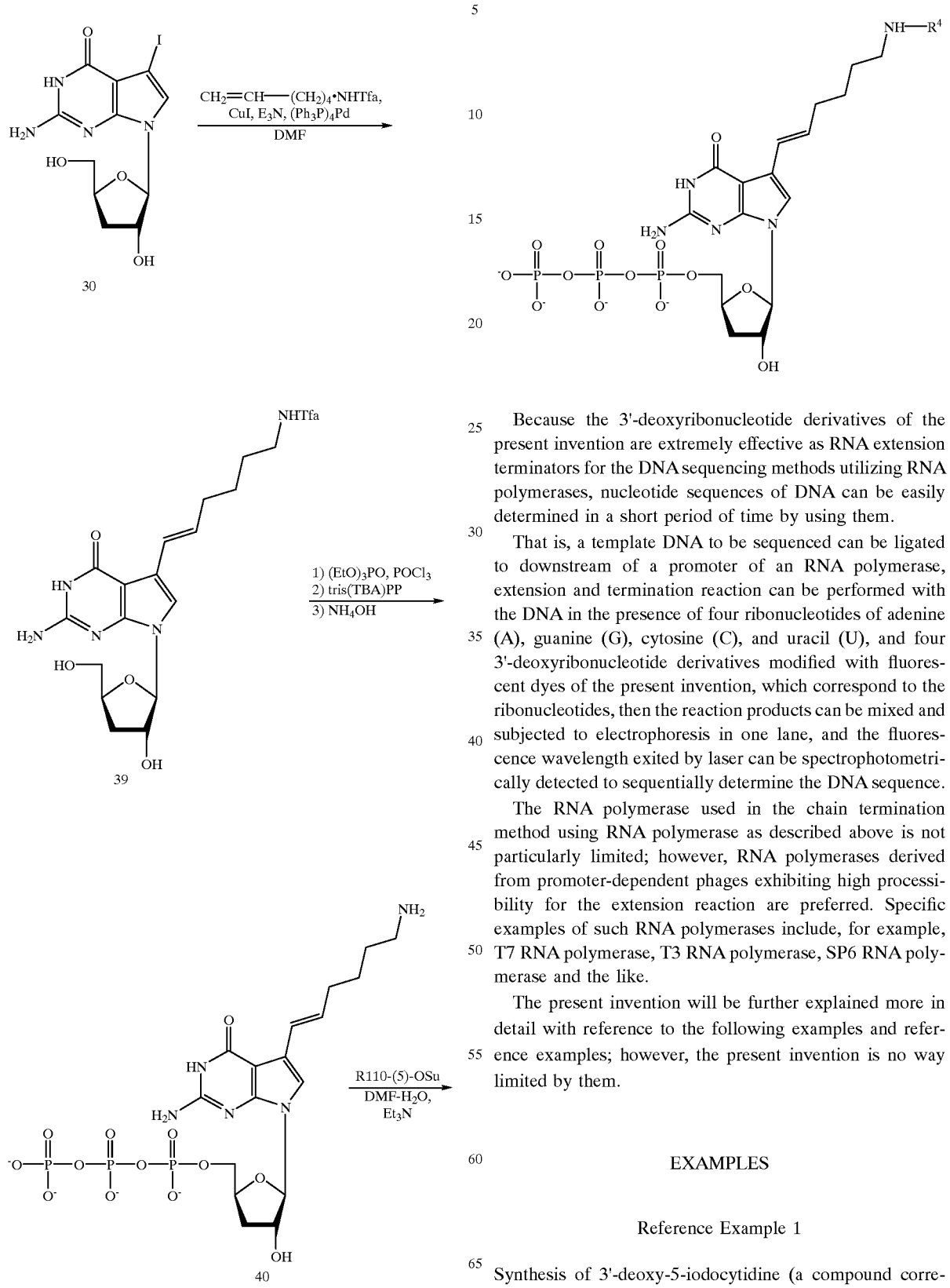

Because the 3'-deoxyribonucleotide derivatives of the present invention are extremely effective as RNA extension terminators for the DNA sequencing methods utilizing RNA polymerases, nucleotide sequences of DNA can be easily determined in a short period of time by using them.

That is, a template DNA to be sequenced can be ligated to downstream of a promoter of an RNA polymerase, extension and termination reaction can be performed with the DNA in the presence of four ribonucleotides of adenine (A), guanine (G), cytosine (C), and uracil (U), and four 3'-deoxyribonucleotide derivatives modified with fluorescent dyes of the present invention, which correspond to the ribonucleotides, then the reaction products can be mixed and subjected to electrophoresis in one lane, and the fluorescence wavelength exited by laser can be spectrophotometrically detected to sequentially determine the DNA sequence.

The RNA polymerase used in the chain termination method using RNA polymerase as described above is not particularly limited; however, RNA polymerases derived from promoter-dependent phages exhibiting high processibility for the extension reaction are preferred. Specific examples of such RNA polymerases include, for example, T7 RNA polymerase, T3 RNA polymerase, SP6 RNA polymerase and the like.

The present invention will be further explained more in detail with reference to the following examples and reference examples; however, the present invention is no way limited by them.

EXAMPLES

Reference Example 1

Synthesis of 3'-deoxy-5-iodocytidine (a compound corresponding to Compound 6 in the above-mentioned synthesis scheme; referred to as Compound 6 hereinafter; the compound Nos. used hereinafter similarly indicate those in the synthesis schemes)

3'-Deoxycytidine (Compound 5, 3.0 g, 13.2 mmol) was suspended in a mixed solution of 1,4-dioxane (300 ml) and ethanol (30 ml), cooled to 10° C., added with silver trifluoroacetate (7.0 g, 31.7 mmol) and iodine (8.04 g, 31.7 mmol), and stirred at room temperature for two hours. After the reaction was completed, the precipitates were removed by filtration through celite, and washed with 1,4-dioxane, and the filtrate and the wash were combined, and concentrated to afford 3.84 g of 3'-deoxy-5-iodocytidine (Compound 6, yield; 82.4%).

$^1$H-NMR (270 MHz, DMSO-$d_6$) δ ppm: 1.64–1.70 (m, 1H, 3'-Ha), 1.88–1.99 (m, 1H, 3'-Hb), 3.60–3.89 (m, 2H, 5'-Ha,b), 4.20–4.21 (m, 1H, 4'-H), 4.37–4.39 (m, 1H, 2'-H), 5.59 (s, 1H, 1'-H), 7.58 (brs, 1H, NH$_2$a), 8.41 (brs, 1H, NH$_2$b), 8.79 (brs, 1H, 6-H)

Reference Example 2

Synthesis of 5-trifluoroacetamido-1-pentyne

To a solution of sodium hydride (60% oil, 5.99 g, 0.15 mol) in DMF (340 ml), trifluoroacetamido (19.2 g, 0.17 mol) was added portionwise as 10 portions with ice cooling. Then, the solution was added with sodium iodide (20.4 g, 0.136 mol), then with a solution of 5-chloro-1-pentyne (13.97 g, 0.136 mol) in dimethylformamide (DMF, 50 ml), and allowed to react at room temperature for 4.5 hours and at 60° C. for 21 hours with stirring. After the reaction mixture was cooled, it was added with an aqueous solution (500 ml) of potassium dihydrogenphosphate (59.2 g), and extracted with ether (500 ml). The ether layer was washed with water, dried over magnesium sulfate and concentrated under reduced pressure, and the resulting residue was purified by silica gel column chromatography (eluent; hexane-ethyl acetate mixed solvent) to afford 17.6 g of 5-trifluoroacetamido-1-pentyne (yield; 67%).

$^1$H-NMR (270 MHz, CDCl$_3$) δ ppm: 1.83 (m, 2H, —CH$_2$CH$_2$—), 2.04 (t, 1H, J=2.7 Hz, H—CC—), 2.31 (dt, 2H, J=2.7, 6.6 Hz, —CCCH$_2$—), 3.52 (q, 2H, J=6.7 Hz, CH$_2$N), 6.88 (brs, 1H, NHTfa)

Reference Example 3

Synthesis of 3'-deoxy-5-(5"-trifluoroacetamido-1"-pentynyl)cytidine

To a solution of 3'-deoxy-5-iodocytidine (Compound 6, 777 mg, 2.20 mmol) in DMF (11 ml), the 5-trifluoroacetamido-1-pentyne (1.18 g, 6.60 mmol) obtained in Reference Example 2, cuprous (I) iodide (83.8 mg, 0.44 mmol), tetrakis(triphenylphosphine)palladium (0) (254 mg, 0.22 mmol), and triethylamine (0.613 ml, 4.4 mmol) were added under nitrogen gas flow, and allowed to reacted at room temperature for 30 minutes. The reaction mixture was diluted with a methylene chloride-methanol mixture (20 ml), added with ion exchange resin AG1X8 (Biolad, HCO$_3^-$ type, 2.02 g), and stirred for 30 minutes. After filtration of the reaction mixture, the filtrate was concentrated, and the residue was purified by silica gel column chromatography (eluent; chloroform-methanol mixed solution), and crystallized from a methanol-ether mixture to afford 409 mg of a novel substance, 3'-deoxy-5-(5"-trifluoroacetamido-1"-pentynyl)cytidine (yield; 46.0%). Melting point: 191–193° C.

$^1$H-NMR (270 MHz, DMSO-$d_6$) δ ppm: 1.63–1.78 (m, 3H, 3'-Ha and CH$_2$CH$_2$CH$_2$N), 1.86–1.96 (m, 1H, 3'-Hb), 2.39–2.44 (m, 2H, CH$_2$CH$_2$CH$_2$N), 3.27–3.31 (m, 2H, CH$_2$N), 3.51–3.82 (m, 2H, 5'-Ha, b), 4.12–4.31 (m, 2H, 2'-H and 4'-H), 5.15 (t, 1H, J=5.1 Hz, 5'-OH), 5.51 (d, 1H, J=4.1 Hz, 2'-OH), 5.62 (s, 1H, 1'-H), 6.69 (brs, 1H, 4-NHa), 7.64 (brs, 1H, 4-NHb), 8.30 (s, 1H, 6-H), 9.50 (brs, 1H, NHTfa)

Reference Example 4

Synthesis of tris(tri-n-butylammonium)pyrophosphate

Tetrasodium pyrophosphate decahydrate (2.23 g) was dissolved in water (50 ml), and loaded on an ion exchange resin column Dowex 50WX8 (Dowex, H$^+$ type, 45 ml). The column was eluted with water, and the eluent was collected until its pH became substantially neutral. The eluent was added with tri-n-butylamine (3.55 ml) and stirred sufficiently. The mixture was concentrated under reduced pressure, and the residue was further concentrated to dryness by azeotropy with ethanol, pyridine, and DMF. The resulting residue was dissolved in dry DMF to a total volume of 10 ml to afford 0.5 M concentration of tris(tri-n-butylammonium) pyrophosphate.

Reference Example 5

Synthesis of 5-(5"-amino-1"-pentynyl)-3'-deoxycytidine-5'-triphosphate

3'-Deoxy-5-(5"-trifluoroacetamido-1"-pentynyl) cytidine (121 mg, 0.3 mmol) was dissolved in triethyl phosphate (1.21 ml), cooled to –20° C., then added with phosphorus oxychloride (25 μl), and stirred at –20° C. After 30 minutes, the reaction mixture was added with further phosphorus oxychloride (22 μl), and stirred for further 5 hours. The reaction mixture was added to 0.5 M solution of the tris(tri-n-butylammonium)pyrophosphate obtained in Reference Example 4 in DMF (3.6 ml) cooled to –20° C., and stirred at room temperature for two hours. After the reaction was completed, the reaction mixture was added with a triethylamine-water mixture (5 ml), left stand overnight, then added with 25% aqueous ammonia (20 ml), and left stand for 4 hours. The reaction mixture was washed with ether, and concentrated to dryness, and the resulting residue was purified by DEAE-Toyopearl ion exchange column chromatography (Tosoh Corporation, 1.7×30 cm, eluent; triethylammonium hydrogencarbonate buffer (pH 7.5), 0 M→0.3 M linear gradient (total volume; 1 L)) to afford 105 mg of a novel substance, 5-(5"-amino-1"-pentynyl)-3'-deoxycytidine-5'-triphosphate (yield; 36.6%).

Reference Example 6

Synthesis of XR-labeled 3'-deoxycytidine-5'-triphosphate (a compound of general formula [I] where V is —C≡C— and n=3)

To 5-(5"-amino-1"-pentynyl)-3'-deoxycytidine-5'-triphosphate (8 μmol) dissolved in a mixture of DMF (300 μl) and water (300 μl) was added with triethylamine (10 μl) and 5-carboxy-X-rhodamine succinimide ester (Molecular Probe, 26.9 μmol), and stirred at room temperature overnight. The reaction mixture was diluted with water (30 ml), and purified by DEAE-Toyopearl ion exchange column chromatography (1.7×15 cm, eluent; triethylammonium hydrogencarbonate buffer (pH 7.5), 0.1 M→0.7 M linear gradient (total volume; 2 L)) to afford 6.28 μmol (yield; 78.5%) of XR-labeled 3'-deoxycytidine-5'-triphosphate represented by the following formula [a compound of the general formula [I] where V is —C≡C— and n=3, abbreviated as XR-3'dCTP(n3) hereinafter].

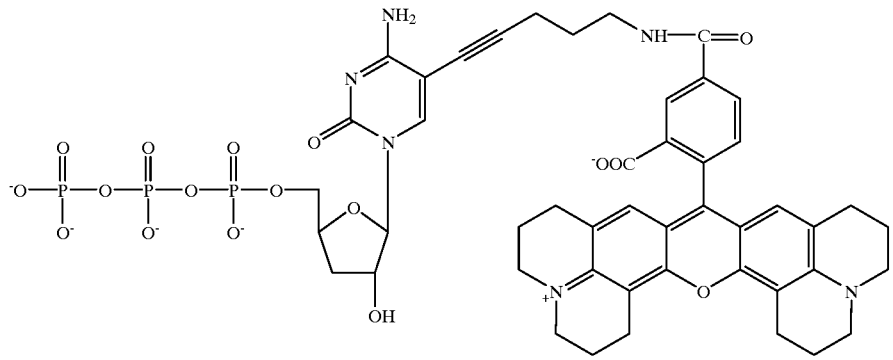

The absorption spectrum for UV-visible region resulting from spectroscopy of the obtained XR-3'dCTP(n3) (measurement wavelength; 700 nm to 200 nm, reference; distilled water) performed by using DU640 UV-visible region spectrophotometer [Beckman] is shown in FIG. 1.

Reference Example 7
Synthesis of 6-trifluoroacetamido-1-hexyne
1) Synthesis of 5-hexynyl-p-toluenesulfonate To an ice-cooled solution of p-toluenesulfonyl chloride (20.11 g, 105.5 mmol) in pyridine (30 ml), 5-hexyn-1-ol (Tokyo Chemical Industry Co., Ltd., 10 ml, 91.7 mmol) was added dropwise, and stirred at room temperature for 20 hours. The reaction mixture was added with water (15 ml), stirred, and then poured into water (500 ml). This solution was extracted with ether (300 ml), and the ether layer was washed with cold 1N-hydrochloric acid, saturated aqueous sodium hydrogencarbonate and water, dried over magnesium sulfate, and concentrated under reduced pressure to afford 7.33 g of 5-hexynyl-p-toluenesulfonate (yield; 32%).

2) Synthesis of 6-iodo-1-hexyne

A mixture of 5-hexynyl-p-toluenesulfonate (7.33 g, 33.3 mmol), sodium iodide (4.99 g, 33.3 mmol) and acetone (37 ml) was allowed to react under reflux for one hour. After cooling, the precipitates were removed by filtration, and the filtrate was concentrated. The resulting residue was purified by silica gel column chromatography (eluent; hexane) to afford 3.31 g of 6-iodo-1-hexyne (yield; 54.8%).

3) Synthesis of 6-trifluoroacetamido-1-hexyne

To a solution of sodium hydride (60% oil, 2.55 g, 63.6 mol) in DMF (50 ml), trifluoroacetamide (8.99 g, 79.6 mmol) was added portionwise as about 10 portions with ice cooling. Subsequently, a solution of 6-iodo-1-hexyne (3.31 g, 15.9 mmol) in DMF (15 ml) was added to the reaction mixture. The reaction mixture was stirred at room temperature for four hours. The reaction mixture was added with saturated aqueous ammonium chloride (100 ml) and ether (100 ml) for extraction. The ether layer was dried over magnesium sulfate, and concentrated under reduced pressure, and the resulting residue was purified by silica gel column chromatography (eluent; hexane-ethyl acetate mixed solvent) to afford 2.0 g of 6-trifluoroacetamido-1-hexyne (yield; 65.4%). Melting point: 41.0–42.5° C.

$^1$H-NMR (270 MHz, CDCl$_3$) δ ppm: 1.53–1.80 (m, 4H, —CH$_2$(CH$_2$)$_2$—), 1.98 (t, 1H, J=2.7 Hz, H—CC—), 2.26 (dt, 2H, J=2.5, 6.7 Hz, CC—CH$_2$—), 3.41 (q, 2H, J=6.8 Hz, CH$_2$—N), 6.48 (brs, 1H, NHTfa)

Reference Example 8
Synthesis of 3'-deoxy-5-(6"-trifluoroacetamido-1"-hexynyl)cytidine (Compound 7)

To a solution of 3'-deoxy-5-iodocytidine (Compound 6, 800 mg, 2.27 mmol) in DMF (11.4 ml), the 6-trifluoroacetamido-1-hexyne obtained in Reference Example 7 (1.31 g, 6.80 mmol) cuprous (I) iodide (86.3 mg, 0.453 mmol), tetrakis(triphenylphosphine)palladium (0) (262 mg, 0.227 mmol), and triethylamine (0.632 ml, 4.53 mmol) were added under nitrogen gas flow, and allowed to react at room temperature for 30 minutes. The reaction mixture was diluted with a methylene chloride-methanol mixture (20 ml), added with ion exchange resin AG1X8 (HCO$_3^-$ type, 2.02 g), and stirred for 30 minutes. After filtration of the reaction mixture, the filtrate was concentrated, and the resulting residue was purified by silica gel column chromatography (eluent, chloroform-methanol mixed solution), crystallized from a methanol-ether mixture to afford 399 mg of a novel substance, 3'-deoxy-5-(6"-trifluoroacetamido-1"-hexynyl)cytidine (Compound 7, yield; 42.1%) Melting point: 195–197° C.

$^1$H-NMR (270 MHz, DMSO-d$_6$) δ ppm: 1.52–1.69 (m, 5H, 3'-Ha and CH$_2$CH$_2$CH$_2$CH$_2$N), 1.86–1.96 (m, 1H, 3'-Hb), 2.39–2.50 (m, 2H, CCH$_2$—), 3.18–3.28 (m, 2H, CH$_2$N), 3.50–3.83 (m, 2H, 5'-Ha, b), 4.11–4.33 (m, 2H, 2'-H and 4'-H), 5.14 (t, 1H, J=4.9 Hz, 5'-OH), 5.50 (d, 1H, J=4.0 Hz, 2'-OH), 5.62 (s, 1H, 1'-H), 6.65 (brs, 1H, 4-NHa), 7.59 (brs, 1H, 4-NHb), 8.29 (s, 1H, 6-H), 9.41 (brs, 1H, NHTfa)

Reference Example 9
Synthesis of 5-(6"-amino-1"-hexynyl)-3'-deoxycytidine-5'-triphosphate (Compound 8)

3'-Deoxy-5-(6"-trifluoroacetamido-1"-hexynyl)cytidine (Compound 7, 125.5 mg, 0.3 mmol) was dissolved in triethyl phosphate (1.26 ml), cooled to −20° C., added with phosphorus oxychloride (25.11 µl), and stirred at −20° C. After 30 minutes, the reaction mixture was added with further phosphorus oxychloride (22.32 µl), and stirred for further 5 hours. This reaction mixture was added to 0.5 M solution of tris(tri-n-butylammonium)pyrophosphate in DMF (3.6 ml) cooled to −20° C., and stirred at room temperature for two hours. After the reaction was completed, the reaction mixture was added with a triethylamine-water mixture (4 ml), left stand overnight, added with 25% aqueous ammonia (20 ml), and left stand for four hours. The reaction mixture was washed with ether, and concentrated to dryness, and the obtained residue was purified by DEAE-Toyopearl ion exchange column chromatography (1.7×30 cm, eluent; triethylammonium hydrogencarbonate buffer (pH 7.5), 0 M→0.3 M linear gradient (total volume; 1 L)) to afford 200 mg of a novel substance, 5-(6"-amino-1"-hexynyl)-3'-deoxycytidine-5'-triphosphate (Compound 8, yield; 69.0%).

Example 1

Synthesis of XR-labeled 3'-deoxycytidine-5'-triphosphate (a compound of the general formula [I] where V is —C≡C— and n=4)

To 5-(6"-amino-1"-hexynyl)-3'-deoxycytidine-5'-triphosphate (Compound 8, 10 μmol) dissolved in a mixture of DMF (300 μl) and water (300 μl), triethylamine (10 μl), and 5-carboxy-X-rhodamine succinimide ester (Molecular Probe, 15 μmol) were added, and stirred at room temperature overnight. The reaction mixture was diluted with water (30 ml), and purified by DEAE-Toyopearl ion exchange column chromatography (1.7×15 cm, eluent; triethylammonium hydrogencarbonate buffer (pH 7.5), 0.1 M→0.7 M linear gradient (total volume; 2 L)) to afford 8.02 μmol (yield; 80.2%) of XR-labeled 3'-deoxycytidine-5'-triphosphate represented by the following formula where n of the methylene chain in the linker section is 4 [a compound of the general formula [I] where V is —C≡C— and n=4, abbreviated as XR-3'dCTP(n4) hereinafter].

20 hours. The reaction mixture was added with water (15 ml), stirred, then poured into water (500 ml), and extracted with ether (500 ml). The ether layer was washed with cold 1N-hydrochloric acid, saturated aqueous sodium hydrogencarbonate and water, dried over magnesium sulfate, and concentrated under reduced pressure to afford 18.3 g of 7-octynyl-p-toluenesulfonate (yield; 85.7%).

3) Synthesis of 8-iodo-1-octyne

A mixture of 7-octynyl-p-toluenesulfonate (18.3 g, 65.2 mmol), sodium iodide (9.77 g, 65.2 mmol) and acetone (91 ml) was allowed to react for four hours under reflux. After cooling, the precipitates were removed by filtration, and the filtrate was concentrated. The resulting residue was purified by silica gel column chromatography (eluent; hexane) to afford 14.5 g of 8-iodo-1-octyne (yield; 94.2%).

4) Synthesis of 8-trifluoroacetamido-1-octyne

To a solution of sodium hydride (60% oil, 9.82 g, 245 mmol) in DMF (200 ml), trifluoroacetamide (34.7 g, 307 mmol) divided into 10 portion was added portionwise with

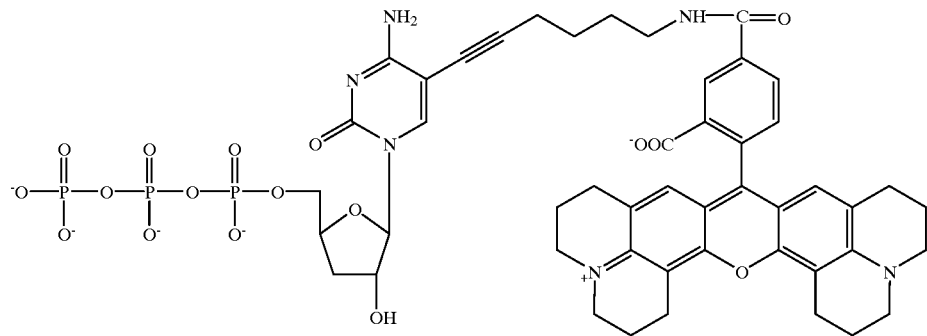

Figure 2:
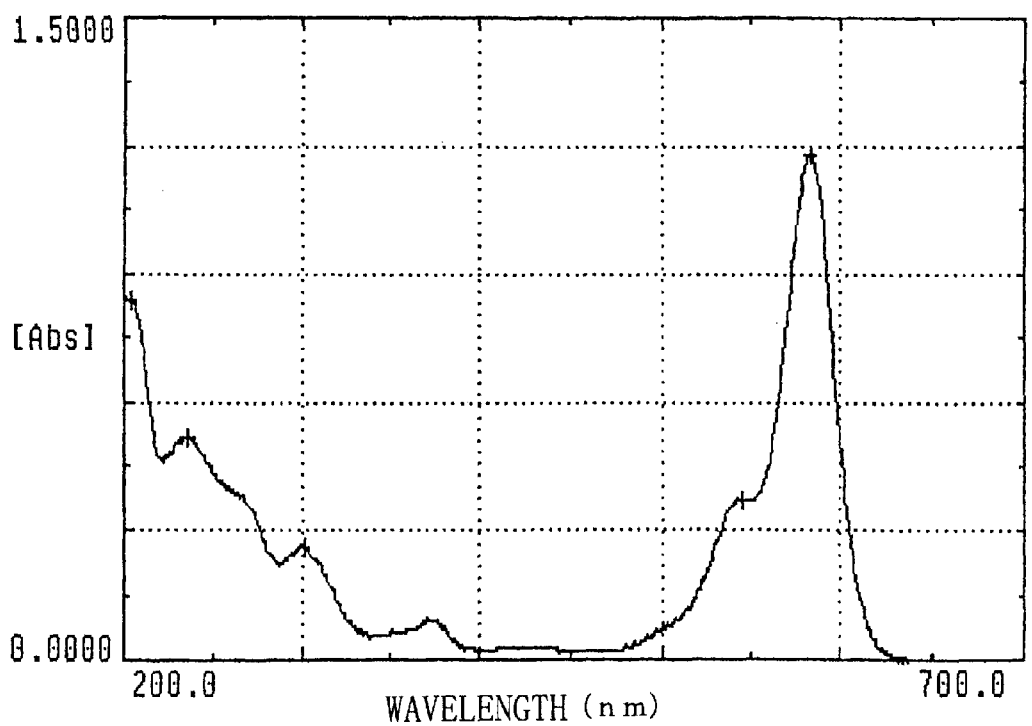
FIG. 2 shows the result of UV-visible region spectrophotometry of the carboxyrhodamine-X-labeled 3'-deoxycytidine-5'-triphosphate (a compound of the general formula [I] where V is —C≡C— and n=4) obtained in Example 1.

The absorption spectrum for UV-visible region resulting from spectroscopy of the obtained XR-3'dCTP(n4) (measurement wavelength; 700 nm to 200 nm, reference; distilled water) performed by using DU640 UV-visible region spectrophotometer [Beckman] is shown in FIG. 2.

Reference Example 10

Synthesis of 8-trifluoroacetamido-1-octyne

1) Synthesis of 7-octyn-1-ol

A suspension of lithium acetylide ethylenediamine complex (Aldrich, 11.3 g, 122.5 mmol) and dimethyl sulfoxide (50 ml) was cooled to 5–10° C., and added dropwise with 1-bromo-6-tetrahydropyranyloxyhexane (Sigma, 25 g, 94.3 mmol) over two hours. Then, the reaction mixture was stirred at room temperature for two hours. The reaction mixture was added with water (10 ml), stirred for ten minutes, then poured into water (150 ml), and extracted with ether (300 ml). The ether layer was washed with water, dried over magnesium sulfate, and concentrated under reduced pressure to afford 18.1 g of 8-(tetrahydropyranyloxy)-1-octyne as oil (yield; 91.2%). Dowex 50WX8 (H$^+$ type, 18 g) was added to a mixture of 8-(tetrahydropyranyloxy)-1-octyne (18 g, 85.6 mmol), chloroform (40 ml) and methanol (140 ml), and heated for 1 hour under reflux. After the resin was separated by filtration, the filtrate was concentrated, and the resulting residue was purified by silica gel column chromatography (eluent; hexane-ethyl acetate mixed solvent) to afford 9.6 g of 7-octyn-1-ol (yield; 88.6%).

2) Synthesis of 7-octynyl-p-toluenesulfonate

To an ice-cooled solution of p-toluenesulfonyl chloride (17.4 g, 91.3 mmol) in pyridine (30 ml), 7-octyn-1-ol (9.6 g, 76.1 mmol) was added dropwise, and stirred at 5–10° C. for ice cooling. Then, the reaction mixture was added with a solution of 8-iodo-1-octyne (14.5 g, 61.4 mmol) in DMF (60 ml), and stirred at room temperature for two hours. The reaction mixture was added with saturated aqueous ammonium chloride (400 ml) and ether (400 ml) for extraction. The ether layer was dried over magnesium sulfate, and concentrated under reduced pressure, and the resulting residue was purified by silica gel column chromatography (eluent; hexane-ethyl acetate mixed solvent), and crystallized from hexane to afford 10.8 g of 8-trifluoroacetamido-1-octyne (yield; 79.3%). Melting point: 29.5–30.0° C.

$^1$H-NMR (270 MHz, CDCl$_3$) δ ppm: 1.36–1.63 (m, 8H, —CH$_2$(CH$_2$)$_4$—), 1.94 (t, 1H, J=2.7 Hz, H—CC—), 2.20 (dt, 2H, J=2.5, 6.7 Hz, CC—CH$_2$—), 3.37 (q, 2H, J=6.8 Hz, CH$_2$—N), 6.28 (brs, 1H, NHTfa)

Reference Example 11

Synthesis of 3'-deoxy-5-(8"-trifluoroacetamido-1"-octynyl)cytidine (Compound 9)

To a solution of 3'-deoxy-5-iodocytidine (Compound 6, 450 mg, 1.27 mmol) in DMF (6.4 ml), the 8-trifluoroacetamido-1-octyne (846 mg, 3.82 mmol) obtained in Reference Example 10, cuprous (I) iodide (48.5 mg, 0.25 mmol), tetrakis(triphenylphosphine)palladium (0) (147 mg, 0.127 mmol), and triethylamine (0.355 ml, 2.55 mmol) were added under nitrogen gas flow, and allowed to react at room temperature for 30 minutes. The reaction mixture was diluted with a methylene chloride-methanol mixture (12 ml), added with ion exchange resin AG1X8 (HCO$_3^-$ type, 1.17 g), and stirred for 30 minutes. After filtration of the reaction mixture, the filtrate was concentrated, and the resulting residue was purified by silica gel column chromatography (eluent; chloroform-methanol mixed solution), and crystallized from a methanol-ether mixture to afford 219 mg of a novel substance, 3'-deoxy-5-(8"-trifluoroacetamido-1"-octynyl)cytidine (Compound 9, yield; 38.5%). Melting point: 165–167° C.

$^1$H-NMR (270 MHz, DMSO-$d_6$) δ ppm: 1.27–1.54 (m, 8H, —(CH$_2$)$_4$—), 1.63–1.69 (m, 1H, 3'-Ha), 1.86–1.97 (m, 1H, 3'-Hb), 2.37 (t, 2H, J=7.0 Hz, CCCH$_2$), 3.14–3.21 (m, 2H, CH$_2$N), 3.49–3.56 (m, 1H, 5'-Ha), 3.75–3.81 (m, 1H, 5'-Hb), 4.08–4.31 (m, 2H, 2'-H and 4'-H), 5.13 (t, 1H, J=5.0 Hz, 5'-OH), 5.49 (d, 1H, J=4.1 Hz, 2'-OH), 5.62 (d, 1H, J=1.4 Hz, 1'-H), 6.62 (brs, 1H, 4-NHa), 7.58 (brs, 1H, 4-NHb), 8.28 (s, 1H, 6-H), 9.41 (brs, 1H, NHTfa)

Reference Example 12
Synthesis of 5-(8"-amino-1"-octynyl)-3'-deoxycytidine-5'-triphosphate (Compound 10)

3'-Deoxy-5-(8"-trifluoroacetamido-1"-octynyl)cytidine (Compound 9, 134 mg, 0.3 mmol) was dissolved in triethyl phosphate (1.34 ml), cooled to −20° C., added with phosphorus oxychloride (25.11 μl), and stirred at −20° C. After 30 minutes, the mixture was added with further phosphorus oxychloride (22.32 μl), and stirred for further 3.5 hours. This reaction mixture was added to 0.5 M solution of tris(tri-n-butylammonium)pyrophosphate in DMF (3.6 ml) cooled to −20° C., and stirred at room temperature for two hours. After the reaction was completed, the reaction mixture was added with a triethylamine-water mixture (5 ml), left stand overnight, then added with 25% aqueous ammonia (20 ml), and left stand for four hours. The reaction mixture was washed with ether, and concentrated to dryness, and the obtained residue was purified by DEAE-Toyopearl ion exchange column chromatography (1.7×30 cm, eluent; triethylammonium hydrogencarbonate buffer (pH 7.5), 0 M→0.3 M linear gradient (total volume; 1 L)) to afford 262 mg of a novel substance, 5-(8"-amino-1"-octynyl)-3'-deoxycytidine-5'-triphosphate (Compound 10, yield; 50.0%).

Example 2
Synthesis of XR-labeled 3'-deoxycytidine-5'-triphosphate (a compound of the general formula [I] where V is —C≡C— and n=6)

To 5-(8"-amino-1"-octynyl)-3'-deoxycytidine-5'-triphosphate (Compound 10, 8 μmol) dissolved in a mixture of DMF (300 μl) and water (300 μl), triethylamine (10 μl) and 5-carboxy-X-rhodamine succinimide ester (Molecular Probe, 12 μmol) were added, and stirred at room temperature overnight. The reaction mixture was diluted with water (30 ml), and purified by DEAE-Toyopearl ion exchange column chromatography (1.7×15 cm, eluent; triethylammonium hydrogencarbonate buffer (pH 7.5), 0.1 M→0.7 M linear gradient (total volume; 2 L)) to afford 5.34 μmol (yield; 66.7%) of XR-labeled 3'-deoxycytidine-5'-triphosphate represented by the following formula [a compound of the general formula [I] where V is —C≡C— and n=6, abbreviated as XR-3'dCTP(n6) hereinafter].

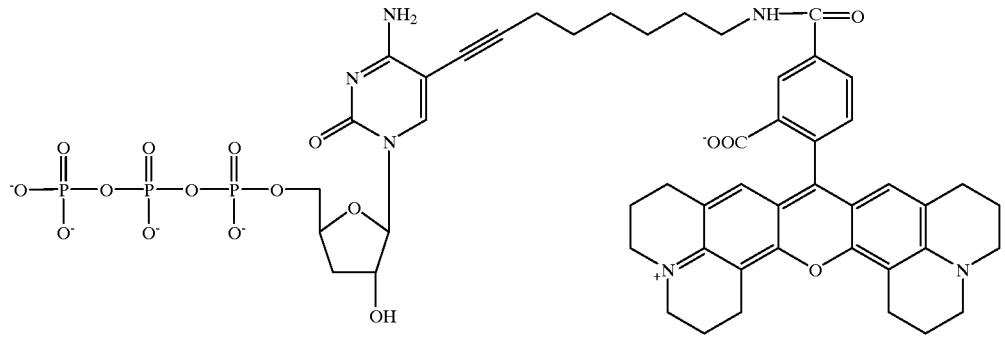

Figure 3:
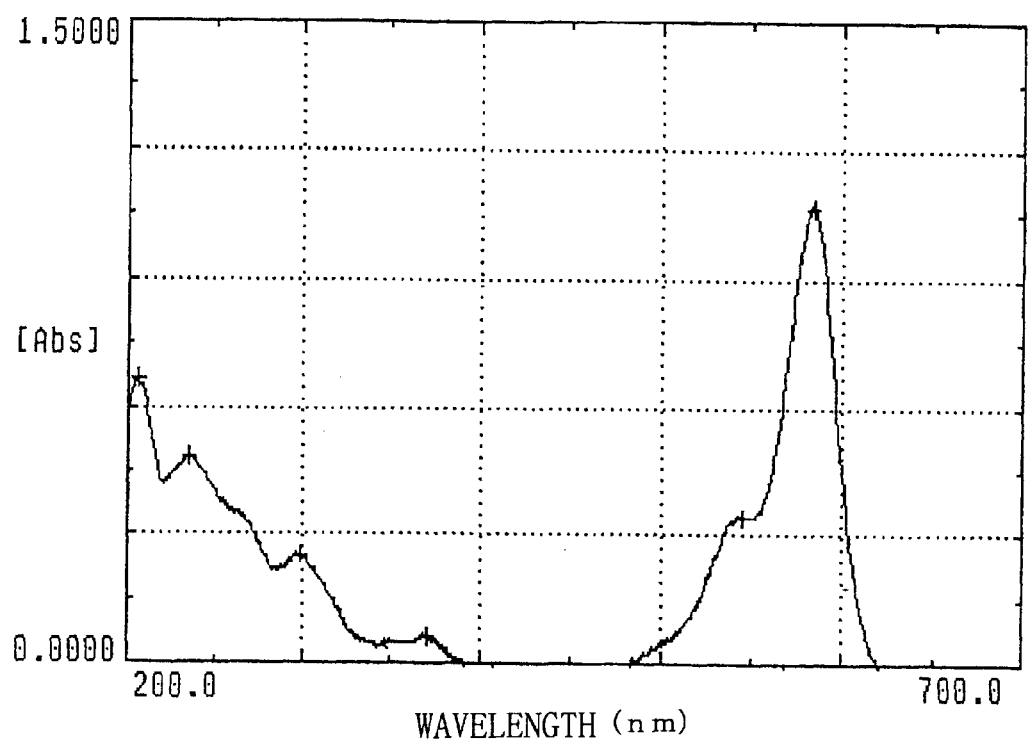
FIG. 3 shows the result of UV-visible region spectrophotometry of the carboxyrhodamine-X-labeled 3'-deoxycytidine-5'-triphosphate (a compound of the general formula [I] where V is —C≡C— and n=6) obtained in Example 2.

The absorption spectrum for UV-visible region resulting from spectroscopy of the obtained XR-3'dCTP(n6) (measurement wavelength; 700 nm to 200 nm, reference; distilled water) performed by using DU640 UV-visible region spectrophotometer [Beckman] is shown in FIG. 3.

Reference Example 13
Synthesis of 6-chloro-9-{2',5'-bis(O-tert-butyldimethylsilyl)-3'-O-[(imidazol-1"-yl) thiocarbonyl]-β-D-ribofuranosyl}-7-deazapurine (Compound 13)

6-Chloro-9-(β-D-ribofuranosyl)-7-deazapurine (Compound 11, 3.58 g, 12.5 mmol) was dissolved in THF (160 ml), added with pyridine (5.1 ml, 62.7 mmol), silver nitrate (4.68 g, 27.6 mmol) and tert-butyldimethylsilyl chloride (4.16 g, 27.6 mmol), and stirred at room temperature overnight. After the reaction was completed, the precipitates were removed by filtration through celite, and the filtrate was concentrated, dissolved in chloroform, and washed with 0.2 N hydrochloric acid and saturated saline. The chloroform layer was dried over anhydrous magnesium sulfate, and the chloroform was evaporated to quantitatively afford 6.42 g of a novel substance, 6-chloro-9-[2,5-bis(O-tert-butyldimethylsilyl)-β-D-ribofuranosyl]-7-deazapurine (Compound 12). This compound was dissolved in DMF (120 ml) without further purification, added with 1,1'-thiocarbonyldiimidazole (13.36 g, 75.0 mmol), and stirred at room temperature overnight. After the reaction was completed, the reaction mixture was added with ethyl acetate and water, and the organic layer was washed with saturated saline. The ethyl acetate layer was dried over anhydrous magnesium sulfate, and concentrated under reduced pressure, and the resulting residue was purified by silica gel column chromatography (eluent; ethyl acetate-n-hexane mixed solvent) to afford 4.03 g of a novel substance, 6-chloro-9-{2',5'-bis(O-tert-butyldimethylsilyl)-3'-O-[(imidazol-1-yl)thiocarbonyl]-β-D-ribofuranosyl}-7-deazapurine (Compound 13, yield; 51.5%).

Reference Example 14
Synthesis of 6-chloro-9-[2',5'-bis(O-tert-butyldimethylsilyl)-3'-deoxy-β-D-ribofuranosyl]-7-deazapurine (Compound 14)

6-Chloro-9-{2',5'-bis(O-tert-butyldimethylsilyl)-3'-O-[(imidazol-1-yl)thiocarbonyl]-β-D-ribofuranosyl}-7- deazpurine (Compound 13, 4.0 g, 6.41 mmol) was dissolved in toluene (200 ml), added with 2,2'-azobis(isobutyronitrile) (0.21 g, 1.3 mmol) and tri-n-butyltin hydride (3.45 ml, 13 mmol), and stirred under nitrogen gas flow at 80° C. for 30 minutes. After the reaction was completed, the toluene was evaporated, and the residue was purified by silica gel column chromatography (eluent; ethyl acetate-n-hexane mixed solvent) to afford 2.60 g of a novel substance, 6-chloro-9-[2',5'-bis(O-tert-butyldimethylsilyl)-3'-deoxy-β-D-ribofuranosyl]-7-deazapurine (Compound 14, yield; 81.5%).

Reference Example 15
Synthesis of 6-chloro-9-(3'-deoxy-β-D-ribofuranosyl)-7-deazapurine (Compound 15)

6-Chloro-9-[2',5'-bis(O-tert-butyldimethylsilyl)-3'-deoxy-β-D-ribofuranosyl] -7-deazapurine (Compound 14, 2.6 g, 5.2 mmol) was dissolved in THF (30 ml), added with 1 M tetrabutylammonium fluoride (12.5 ml, 12.5 mmol), and stirred at room temperature overnight. After the reaction was completed, the reaction mixture was concentrated under reduced pressure, and purified by silica gel column chromatography (eluent; chloroform-methanol mixed solvent) to quantitatively afford 1.47 g of a novel substance, 6-chloro-9-(3'-deoxy-β-D-ribofuranosyl)-7-deazapurine (Compound 15).

$^1$H-NMR (270 MHz, DMSO-$d_6$) δ ppm: 1.93, 2.23 (m, 2H, 3'-Ha, b), 3.55, 3.71 (2dd, 2H, J=4.1, 11.9; 3.2, 11.6 Hz, 5'-Ha, b), 4.36 (m, 1H, 2'-H), 4.45 (m, 1H, 4'-H), 5.02 (brs, 1H, 5'-OH), 5.66 (brs, 1H, 2'-OH), 6.19 (d, 1H, J 2.4 Hz, 1'-H), 6.70 (d, 1H, J 3.8 Hz, 7-H), 8.02 (d, 1H, J=4.1 Hz, 8-H), 8.66 (s, 1H, 2-H)

Reference Example 16
Synthesis of 6-chloro-9-(3'-deoxy-2',5'-di-O-acetyl-β-D-ribofuranosyl)-7-deazapurine (Compound 16)

6-Chloro-9-(3'-deoxy-β-D-ribofuranosyl)-7-deazapurine (Compound 15, 1.47 g, 5.45 mmol) was dissolved in pyridine (15 ml), added with acetic anhydride (5 ml), and stirred at room temperature overnight. After the reaction was completed, the reaction mixture was cooled to 0° C., added with methanol (5 ml), and concentrated under reduced pressure. The residue was dissolved in chloroform, and washed with 0.5 N hydrochloric acid and saturated saline. The chloroform layer was dried over anhydrous magnesium sulfate, and the chloroform was evaporated to quantitatively afford 2.00 g of a novel substance, 6-chloro-9-(3'-deoxy-2',5'-di-O-acetyl-β-D-ribofuranosyl)-7-deazapurine (Compound 16).

Reference Example 17
Synthesis of 6-chloro-7-iodo-9-(3'-deoxy-2',5'-di-O-acetyl-β-D-ribofuranosyl)-7-deazapurine (Compound 17)

6-Chloro-9-(3'-deoxy-2',5'-di-O-acetyl-β-D-ribofuranosyl)-7-deazapurine (Compound 16, 1.44 g, 4.07 mmol) was dissolved in acetonitrile (67 ml), added with cerium (IV) diammonium nitrate (0.62 g, 2.44 mmol) and iodine (1.12 g, 2.03 mmol), and stirred at 80° C. for 30 minutes. After the reaction was completed, the acetonitrile was concentrated under reduced pressure, and the residue was dissolved in ethyl acetate, and washed with 5% sodium hydrogensulfite solution, saturated sodium hydrogencarbonate solution and saturated saline. The ethyl acetate layer was dried over anhydrous magnesium sulfate, and evaporated, and the residue was crystallized from methylene chloride-ether to afford 1.46 g of a novel substance, 6-chloro-7-iodo-9-(3'-deoxy-2',5'-di-O-acetyl-β-D-ribofuranosyl)-7-deazapurine (Compound 17, yield; 75.0%). Melting point: 149–150° C.

$^1$H-NMR (270 MHz, DMSO-$d_6$) δ ppm: 2.14, 2.17 (2s, 6H, 2Ac), 2.23–2.49 (m, 2H, 3'-Ha, b), 4.25–4.48 (m, 2H, 5'-Ha, b), 4.58–4.68 (m, 1H, 4'-H), 5.52–5.54 (m, 1H, 2'-H), 6.33 (d, 1H, J=1.4 Hz, 1'-H), 7.64 (s, 1H, 8-H), 8.63 (s, 1H, 2-H)

Reference Example 18
Synthesis of 7-iodo-3'-deoxy-7-deazaadenosine (Compound 18)

6-Chloro-7-iodo-9-(3'-deoxy-2',5'-di-O-acetyl-β-D-ribofuranosyl)-7-deazapurine (Compound 17, 1.63 g, 3.40 mmol) and ammonia-methanol (70 ml) were allowed to react at 110° C. for 20 hours. After the reaction was completed, the reaction mixture was concentrated under reduced pressure, and crystallized from methanol to afford 1.00 g of a novel substance, 7-iodo-3'-deoxy-7-deazaadenosine (Compound 18, yield; 78.8%). Melting point: 223–225° C. (decomposition)

Reference Example 19
Synthesis of 7-deaza-7-(6"-trifluoroacetamido-1"-hexynyl)-3'-deoxyadenosine (Compound 19)

To a solution of 7-iodo-3'-deoxy-7-deazaadenosine (Compound 18, 220 mg, 0.585 mmol) in DMF (3 ml), the 6-trifluoroacetamido-1-hexyne obtained in Reference Example 7 (339 mg, 1.75 mmol), cuprous (I) iodide (22.3 mg, 0.117 mmol), tetrakis(triphenylphosphine)palladium (0) (67.5 mg, 0.058 mmol), and triethylamine (0.163 ml, 1.17 mmol) were added under nitrogen gas flow, and allowed to react at room temperature for 30 minutes. The reaction mixture was diluted with a methylene chloride-methanol mixture (6 ml), added with ion exchange resin AG1X8 ($HCO_3^-$ type, 0.55 g), and stirred for 30 minutes. After filtration of the reaction mixture, the filtrate was concentrated, and the resulting residue was purified by silica gel column chromatography (eluent; chloroform-methanol mixed solution) to afford 210 mg of a novel substance, 7-deaza-7-(6"-trifluoroacetamido-1"-hexynyl)-3'-deoxyadenosine (Compound 19, yield; 81.6%).

$^1$H-NMR (270 MHz, DMSO-$d_6$) δ ppm: 1.55–1.63 (m, 4H, —$(CH_2)_2$—), 1.83–1.92 (m, 1H, 3'-Ha), 2.13–2.24 (m, 1H, 3'-Hb), 2.47–2.52 (m, 2H, CCC$H_2$—), 3.16–3.24 (m, 2H, C$H_2$N), 3.46–3.54 (m, 1H, 5'-Ha), 3.62–3.68 (m, 1H, 5'-Hb), 4.23–4.38 (m, 2H, 2'-H and 4'-H), 5.03 (t, 1H, J=5.5 Hz, 5'-OH), 5.56 (d, 1H, J=4.3 Hz, 2'-OH), 6.01 (d, 1H, J=2.2 Hz, 1'-H), 6.60 (brs, 2H, 6-$NH_2$), 7.65 (s, 1H, 8-H), 8.11 (s, 1H, 2-H), 9.44 (brs, 1H, NHTfa)

Reference Example 20
Synthesis of 7-deaza-7-(6"-amino1"-hexynyl)-3'-deoxyadenosine-5'-triphosphate (Compound 20)

7-Deaza-7-(6"-trifluoroacetamido-1"-hexynyl)-3'-deoxyadenosine (Compound 19, 181 mg, 0.41 mmol) was dissolved in triethyl phosphate (1.81 ml), cooled to −20° C., then added with phosphorus oxychloride (34.32 μl), and stirred at −20° C. After 30 minutes, the reaction mixture was added with further phosphorus oxychloride (30.5 μl), and stirred for further four hours. This reaction mixture was added to 0.5 M solution of tris(tri-n-butylammonium) pyrophosphate in DMF (4.9 ml) cooled to −20 ° C., and stirred at room temperature for three hours. After the reaction was completed, the reaction mixture was added with a triethylamine-water mixture (5 ml), left stand overnight, added with 25% aqueous ammonia (20 ml), and left stand for four hours. The reaction mixture was washed with ether, and concentrated to dryness, and the resulting residue was purified by DEAE-Toyopearl ion exchange column chromatography (1.2×30 cm, eluent; triethylammonium hydrogencarbonate buffer (pH 7.5), 0 M→0.3 M linear gradient (total volume; 1 L)) to afford 283 mg of a novel substance 7-deaza-7-(6"-amino-1"-hexynyl)-3'-deoxyadenosine-5'-triphosphate (Compound 20, yield; 69.6%).

Example 3
Synthesis of R6G-labeled 7-deaza-3'-deoxyadenosine-5'-triphosphate (a compound of the general formula [I] where V is —C≡C— and n=4)

To 7-deaza-7-(6"-amino-1"-hexynyl)-3'-deoxyadenosine-5'-triphosphate (Compound 20, 8 μmol) dissolved in a mixture of DMF (0.6 ml) and water (0.3 ml), triethylamine (10 μl) and a solution of 5-carboxyrhodamine-6G succinimide ester (Molecular Probe, 16 μmol) in DMF (1.3 ml) were added, and stirred at room temperature overnight. The reaction mixture was diluted with water (30 ml), and purified by DEAE-Toyopearl ion exchange column chromatography (1.2×30 cm, eluent; triethylammonium hydrogencarbonate buffer (pH 7.5), 0.1 M→0.6 M linear gradient (total volume; 2 L)) to afford 5.33 μmol (yield; 66.7%) of R6G-labeled 7-deaza-3'-deoxyadenosine-5'-triphosphate represented by the following formula [a compound of the general formula [I] where V is —C≡C— and n=4, abbreviated as R6G-3'dATP(n4) hereinafter].

gel column chromatography (eluent; chloroform-methanol mixed solution) to afford 216 mg of a novel substance, 7-deaza-7-(8"-trifluoroacetamido-1"-octynyl)-3'-deoxyadenosine (Compound 21, yield; 78.7%).

$^1$H-NMR (270 MHz, DMSO-$d_6$) δ ppm: 1.29–1.58 (m, 8H, —(CH$_2$)$_4$—), 1.83–1.91 (m, 1H, 3'-Ha), 2.14–2.24 (m, 1H, 3'-Hb), 2.44–2.51 (m, 2H, CCCH$_2$), 3.15–3.22 (m, 2H, CH$_2$N), 3.46–3.54 (m, 1H, 5'-Ha), 3.62–3.70 (m, 1H, 5'-Hb), 4.26–4.36 (m, 2H, 2'-H and 4'-H), 5.04 (t, 1H, J=5.4 Hz, 5'-OH), 5.56 (d, 1H, J=4.6 Hz, 2'-OH), 6.01 (d, 1H, J=2.4 Hz, 1'-H), 6.60 (brs, 2H, 6-NH$_2$), 7.65 (s, 1H, 8-H), 8.11 (s, 1H, 2-H), 9.38 (brs, 1H, NHTfa)

Reference Example 22
Synthesis of 7-deaza-7-(8"-amino1"-octynyl)-3'-deoxyadenosine-5'-triphosphate (Compound 22)

7-Deaza-7-(8"-trifluoroacetamido-1"-octynyl)-3'-deoxyadenosine (Compound 21, 189 mg, 0.403 mmol) was dissolved in triethyl phosphate (1.89 ml), cooled to −20° C., then added with phosphorus oxychloride (33.7 μl), and stirred at −20° C. After 30 minutes, the reaction mixture was added with further phosphorus oxychloride (30.0 μl), and stirred for further four hours. This reaction mixture was added to 0.5 M solution of tris(tri-n-butylammonium)

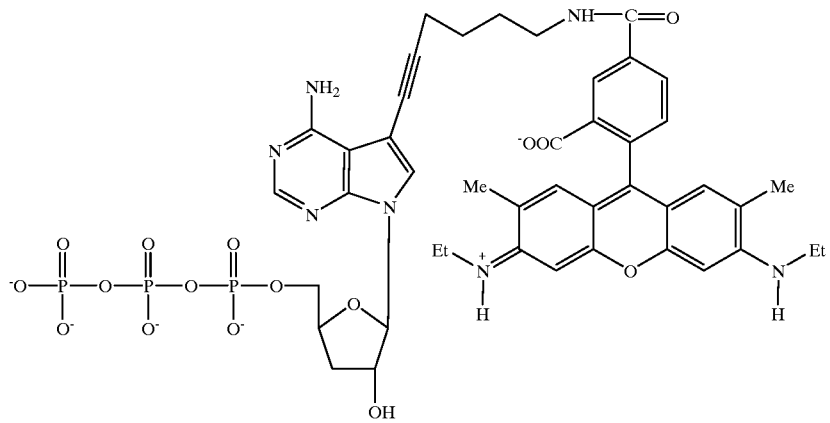

In the formula, Et represents an ethyl group, and Me represents a methyl group.

Figure 4:
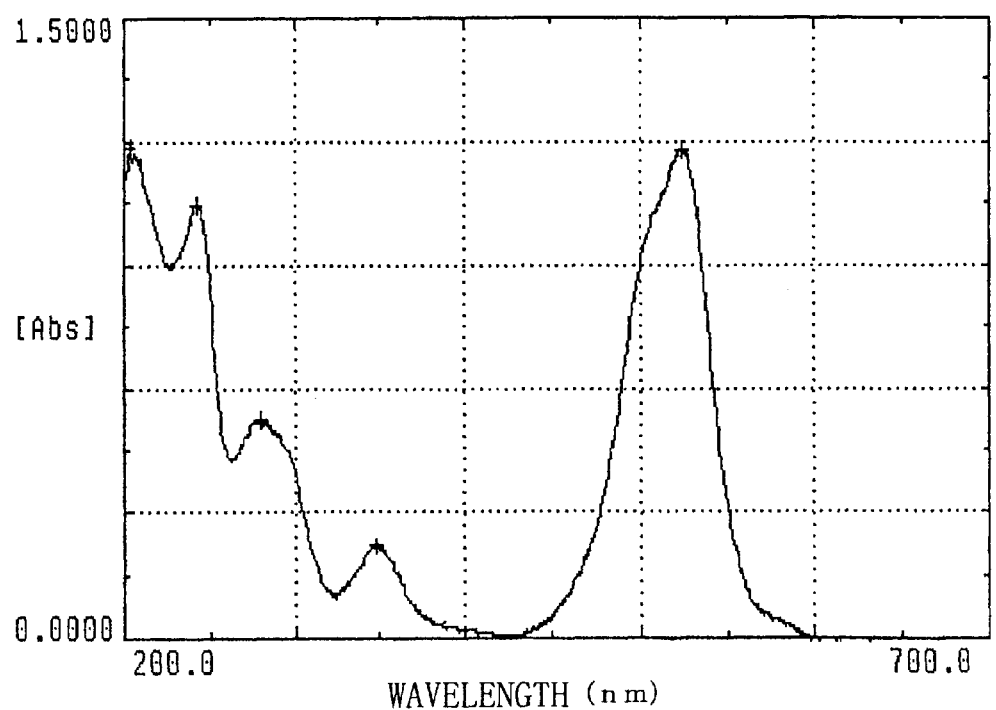
FIG. 4 shows the result of UV-visible region spectrophotometry of the carboxyrhodamine-6G-labeled 7-deaza-3'-deoxyadenosine-5'-triphosphate (a compound of the general formula [I] where V is —C≡C— and n=4) obtained in Example 3.

The absorption spectrum for UV-visible region resulting from spectroscopy of the obtained R6G-3'dATP(n4) (measurement wavelength; 700 nm to 200 nm, reference; distilled water) performed by using DU640 UV-visible region spectrophotometer [Beckman] is shown in FIG. 4.

Reference Example 21
Synthesis of 7-deaza-7-(8"-trifluoroacetamido1"-octynyl)-3'-deoxyadenosine (Compound 21)

To a solution of 7-iodo-3'-deoxy-7-deazaadenosine (Compound 18, 220 mg, 0.585 mmol) in DMF (3 ml), the 8-trifluoroacetamido-1-octyne obtained in Reference Example 10 (388 mg, 1.75 mmol), cuprous (I) iodide (22.3 mg, 0.117 mmol), tetrakis(triphenylphosphine)palladium (0) (67.5 mg, 0.058 mmol), and triethylamine (0.163 ml, 1.17 mmol) were added under nitrogen gas flow, and allowed to react at room temperature for 30 minutes. The reaction mixture was diluted with a methylene chloride-methanol mixture (6 ml), added with ion exchange resin AG1X8 (HCO$_3^-$ type, 0.55 g), and stirred for 30 minutes. After filtration of the reaction mixture, the filtrate was concentrated, and the resulting residue was purified by silica pyrophosphate in DMF (4.8 ml) cooled to −20° C., and stirred at room temperature for three hours. After the reaction was completed, the reaction mixture was added with a triethylamine-water mixture (15 ml), left stand overnight, added with 25% aqueous ammonia (20 ml), and left stand for four hours. The reaction mixture was washed with ether, and concentrated to dryness, and the resulting residue was purified by DEAE-Toyopearl ion exchange column chromatography (1.2×30 cm, eluent; triethylammonium hydrogencarbonate buffer (pH 7.5), 0 M→0.6 M linear gradient (total volume; 1 L)) to afford 143 mg of a novel substance, 7-deaza-7-(8"-amino-1"-octynyl)-3'-deoxyadenosine-5'-triphosphate (Compound 22, yield; 35%)).

Example 4
Synthesis of R6G-labeled 7-deaza-3'-deoxyadenosine-5'-triphosphate (a compound of the general formula [I] where V is —C≡C— and n=6)

To 7-deaza-7-(8"-amino-1"-octynyl)-3'-deoxyadenosine-5'-triphosphate (Compound 22, 8 μmol) dissolved in a mixture of DMF (0.6 ml) and water (0.3 ml), triethylamine (10 μl) and a solution of 5-carboxyrhodamine-6G succinimide ester (Molecular Probe, 16 μmol) in DMF (1.3 ml) were added, and stirred at room temperature overnight. The reaction mixture was diluted with water (30 ml), and purified by DEAE-Toyopearl ion exchange column chromatography (1.2×30 cm, eluent; triethylammonium hydrogencarbonate buffer (pH 7.5), 0.1 M→0.6 M linear gradient (total volume; 2 L)) to afford 4.3 μmol (yield; 53.8%) of R6G-labeled 7-deaza-3'-deoxyadenosine-5'-triphosphate represented by the following formula [a compound of the general formula [I] where V is —C≡C— and n=6, abbreviated as R6G-3'DATP(n6) hereinafter].

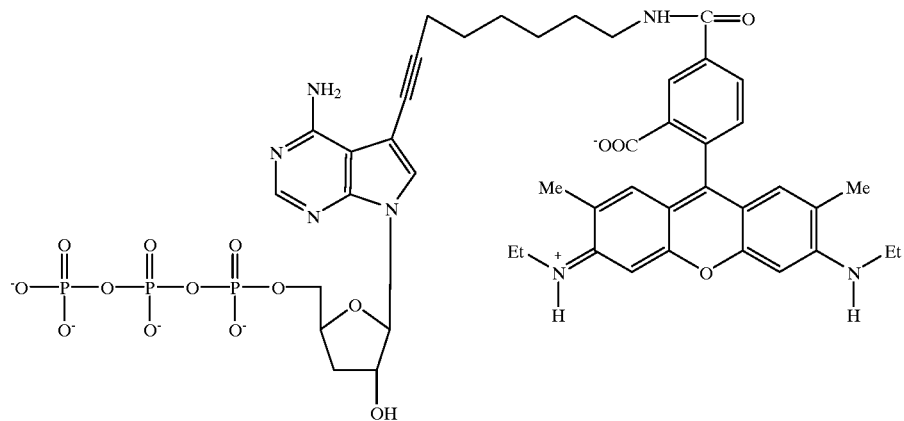

In the formula, Et represents an ethyl group, and Me represents a methyl group.

Figure 5:
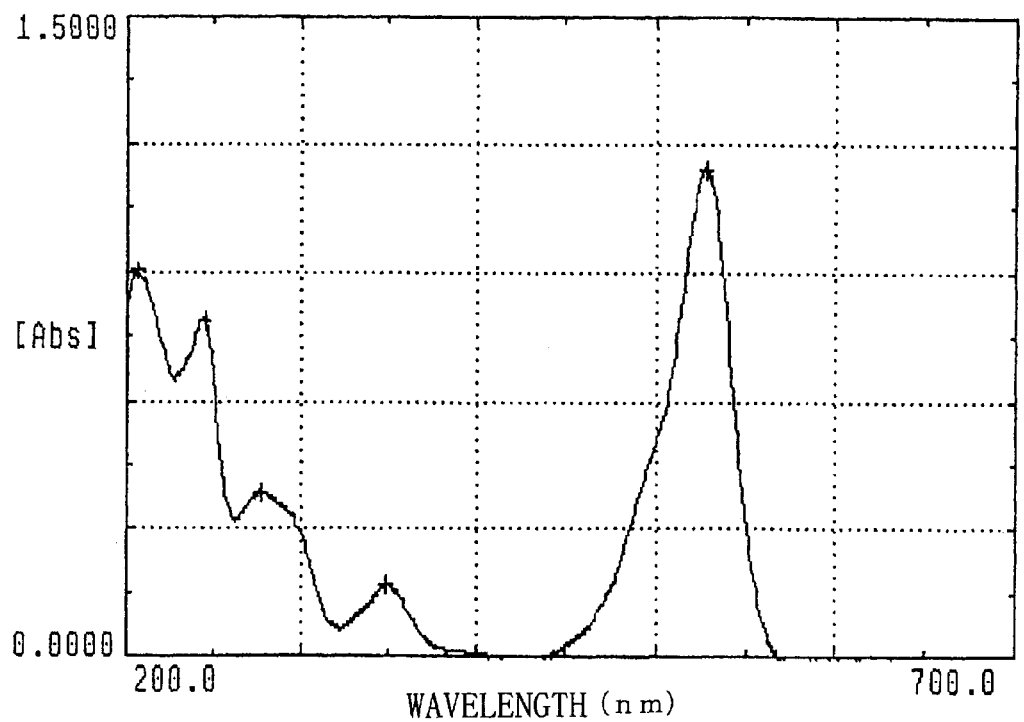
FIG. 5 shows the result of UV-visible region spectrophotometry of the carboxyrhodamine-6G-labeled 7-deaza-3'-deoxyadenosine-5'-triphosphate (a compound of the general formula [I] where V is —C≡C— and n=6) obtained in Example 4.

The absorption spectrum for UV-visible region resulting from spectroscopy of the obtained R6G-3'dATP(n6) (measurement wavelength; 700 nm to 200 nm, reference; distilled water) performed by using DU640 UV-visible region spectrophotometer [Beckman] is shown in FIG. 5.

Reference Example 23
Synthesis of 3'-deoxy-5-iodouridine (Compound 2)

3'-Deoxyuridine (Compound 1, 2.08 g, 9.11 μmol) was dissolved in acetic acid (75 ml), added with cerium (IV) diammoniumnitrate (2.50 g, 4.56 mmol) and iodine (1.39 g, 2.73 mmol), and stirred at 80° C. for 30 minutes. After the reaction was completed, the reaction mixture was concentrated under reduced pressure, and further concentrated by azeotropy three times with an ethanol-toluene mixture (1:2 v/v; 30 ml), and three times with a water-ethanol mixture (1:2 v/v; 30 ml) to afford an oily product. The resulting residue was purified by silica gel column chromatography (eluent; methylene chloride-methanol mixed solvent) to afford 1.78 g of 3'-deoxy-5-iodouridine (Compound 2, yield; 55.08%).

1H-NMR (270 MHz, DMSO-$d_6$) δ ppm: 1.89–1.92 (m, 1H, 3'-Ha), 2.17–2.26 (m, 1H, 31'-Hb), 3.51–3.56 (m, 1H, 5'-Ha), 3.74–3.79 (m, 1H, 5'-Hb), 4.22–4.30 (m, 2H, 2'-H and 4'-H), 5.59 (s, 1H, 1'-H), 8.31 (s, 1H, 6-H), 11.72 (s, 1H, NH)

Reference Example 24
Synthesis of 3'-deoxy-5-(6"-trifluoroacetamido-1"-hexynyl) uridine (Compound 3)

To a solution of 3'-deoxy-5-iodouridine (Compound 2, 805 mg, 2.27 mmol) in DMF (12 ml), the 6-trifluoroacetamido-1-hexyne obtained in Reference Example 7 (1.31 g, 6.80 mmol), cuprous (I) iodide (86.3 mg, 0.453 mmol), tetrakis(triphenylphosphine)palladium (0) (262 mg, 0.227 mmol), and triethylamine (0.63 ml, 4.53 mmol) were added under nitrogen gas flow, and allowed to react at room temperature for four hours. The reaction mixture was concentrated under reduced pressure, and the resulting residue was dissolved in a methylene chloride-methanol mixture (20 ml), added with ion exchange resin AG1X8 (Biolad, $HCO_3^-$ type, 2 g), and stirred for 30 minutes. After filtration of the reaction mixture, the filtrate was concentrated, and the resulting residue was purified by silica gel column chromatography (eluent; methylene chloride-methanol mixed solution) to afford 419 mg of a novel substance, 3'-deoxy-5-(6"-trifluoroacetamido-1"-hexynyl)uridine (Compound 3, yield; 45.5%).

$^1$H-NMR (270 MHz, DMSO-$d_6$) δ ppm: 1.49–1.64 (m, 4H, —(CH$_2$)$_2$—), 1.92–1.97 (m, 1H, 3'-Ha), 2.17–2.28 (m, 1H, 3'-Hb), 2.39 (t, 2H, J=6.9 Hz, —CCCH$_2$), 3.21 (q, 2H, J=6.3 Hz, CH$_2$N), 3.49–3.54 (m, 1H, 5'-Ha), 3.72–3.75 (m, 1H, 5'-Hb), 4.24–4.35 (m, 2H, 2'-H and 4'H), 5.20 (t, 1H, J=4.9 Hz, 5'-OH), 5.52 (d, 1H, J=3.8 Hz, 2'-OH), 5.75 (s, 1H, J=2.2 Hz, 1'-H), 8.23 (s, 1H, 6-H), 9.42 (brs, 1H, NHTfa), 11.57 (s, 1H, 3-NH)

Reference Example 25
Synthesis of 5-(6"-amino-1"-hexynyl)-3'-deoxyuridine-5'-triphosphate (Compound 4)

3'-Deoxy-5-(6"-trifluoroacetamido-1"-hexynyl)uridine (Compound 3, 122.5 mg, 0.3 mmol) was dissolved in triethyl phosphate (1.23 ml), cooled to −20° C., added with phosphorus oxychloride (25 μl), and stirred at −20° C. After 30 minutes, the reaction mixture was added with further phosphorus oxychloride (22 μl), and stirred for further five hours. This reaction mixture was added to 0.5 M solution of tris(tri-n-butylammonium)pyrophosphate in the DMF (3.6 ml) cooled to −20° C., and stirred at room temperature for four hours. After the reaction was completed, the reaction mixture was added with a triethylamine-water mixture (5 ml), left stand overnight, added with 25% aqueous ammonia (20 ml), and left stand for four hours. The reaction mixture was washed with ether, and concentrated to dryness, and the resulting residue was purified by DEAE-Toyopearl ion exchange column chromatography (Tosoh Corporation, 1.2× 30 cm, eluent; triethylammonium hydrogencarbonate buffer (pH 7.5), 0 M→0.3 M linear gradient (total volume; 1 L)) to afford 172 mg of a novel substance, 5-(6"-amino-1"-hexynyl)-3'-deoxyuridine-5'-triphosphate (Compound 4, yield; 60.0%).

Example 5
Synthesis of TMR-labeled 3'-deoxyuridine-5'-triphosphate (a compound of the general formula [I] where V is —C≡C— and n=4)

To 5-(6"-amino-1"-hexynyl)-3'-deoxyuridine-5'-triphosphate (Compound 4, 8 μmol) dissolved in a mixture of DMF (300 μl) and water (300 μl), triethylamine (10 μl) and 5-carboxytetramethylrhodamine succinimide ester (Molecular Probe, 13 μmol) were added, and stirred at room temperature overnight. The reaction mixture was diluted with water (30 ml), and purified by DEAE-Toyopearl ion exchange column chromatography (1.7×30 cm, eluent; triethylammonium hydrogencarbonate buffer (pH 7.5), 0.05 M→0.7 M linear gradient (total volume; 2 L)) to afford 5.9 μmol (yield; 73.8%) of TMR-labeled 3'-deoxyuridine-5'-triphosphate represented by the following formula [a compound of the general formula [I] where V is —C≡C— and n=4, abbreviated as TMR-3'dUTP(n4) hereinafter].

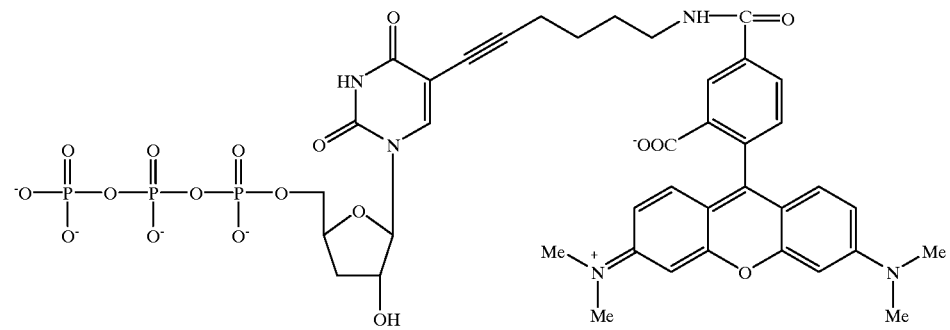

In the formula, Me represents a methyl group.

Figure 6:
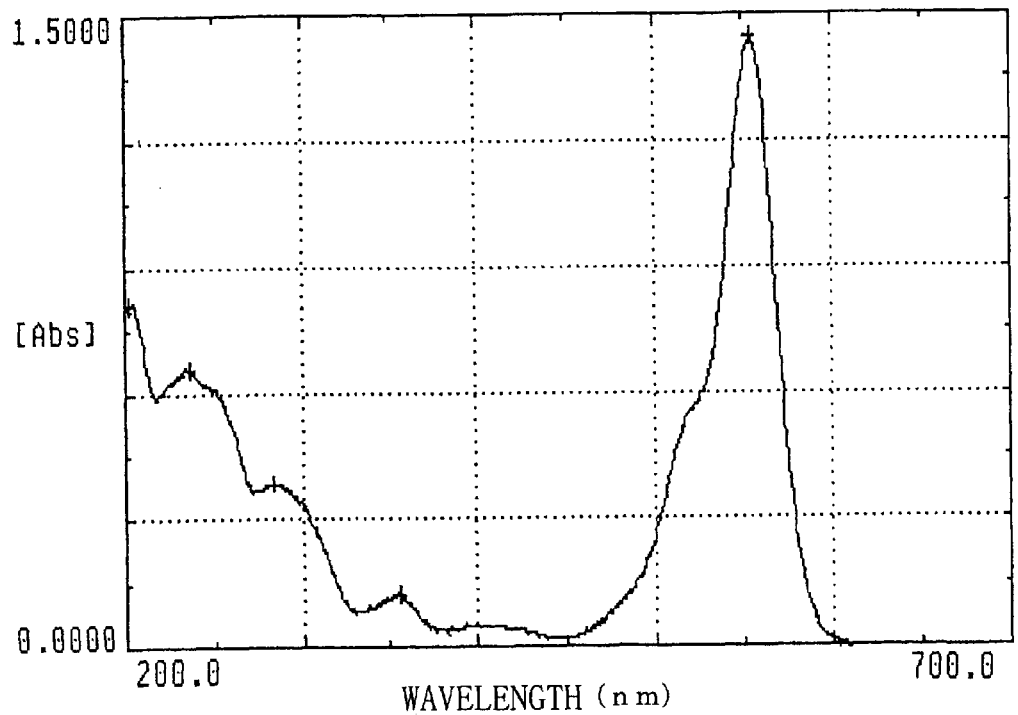
FIG. 6 shows the result of UV-visible region spectrophotometry of the carboxytetramethylrhodamine-labeled 3'-deoxyuridine-5'-triphosphate (a compound of the general formula [I] where V is —C≡C— and n=4) obtained in Example 5.

The absorption spectrum for UV-visible region resulting from spectroscopy of the obtained TMR-3'dUTP n4) (measurement wavelength; 700 nm to 200 nm, reference; distilled water) performed by using DU640 UV-visible region spectrophotometer [Beckman] is shown in FIG. 6.

Reference Example 26
Synthesis of 6-methoxy-2-methylthio-9-{2',5'-bis(O-tert-butyldimethylsilyl)-3'-O-[(imidazol-1-yl)thiocarbonyl]-β-D-ribofuranosyl}-7-deazapurine (Compound 25)

6-Methoxy-2-methylthio-9-(β-D-ribofuranosyl)-7-deazapurine (Compound 23, 12.86 g, 39.28 mmol) was dissolved in THF (580 ml), added with pyridine (16.8 ml, 208 mmol), silver nitrate (15.55 g, 91.5 mmol) and tert-butyldimethylsilyl chloride (13.80 g, 91.5 mmol), and stirred at room temperature overnight. After the reaction was completed, the precipitates were removed by filtration through celite, and the filtrate was concentrated, dissolved in chloroform, and washed with 0.2 N hydrochloric acid and saturated saline. The chloroform layer was dried over anhydrous magnesium sulfate, and the chloroform was evaporated to afford 24.0 g of crude 6-methoxy-2-methylthio-9-[2',5'-bis(O-tert-butyldimethylsilyl)-β-D-ribofuranosyl]-7-deazapurine (Compound 24). The resulting Compound 24 (24.0 g) was dissolved in DMF (400 ml), added with 1,1'-thiocarbonyldiimidazole (35.0 g, 196.5 mmol), and stirred at room temperature overnight. After the reaction was completed, the reaction mixture was added with ethyl acetate and water, and the organic layer was washed with saturated saline. The ethyl acetate layer was dried over anhydrous magnesium sulfate, and concentrated under reduced pressure, and the resulting residue was purified by silica gel column chromatography (eluent; ethyl acetate-chloroform mixed solvent) to afford 20.45 g of a novel substance, 6-methoxy-2-methylthio-9-{2',5'-bis(O-tert-butyldimethylsilyl)-3'-O-[(imidazol-1-yl)thiocarbonyl]-β-D-ribofuranosyl}-7-deazapurine (Compound 25, yield; 78.2%).

Reference Example 27
Synthesis of 6-methoxy-2-methylthio-9-[2',5'-bis(O-tert-butyldimethylsilyl)-3'-deoxy-β-D-ribofuranosyl]-7-deazapurine (Compound 26)

6-Methoxy-2-methylthio-9-{2',5'-bis(O-tert-butyldimethylsilyl)-3'-O-[(imidazol-1-yl)thiocarbonyl]-β-D-ribofuranosyl}-7-deazapurine (Compound 25, 20.45 g, 30.7 mmol) was dissolved in toluene (1 L), added with 2,2'-azobis(isobutyronitrile) (1.01 g, 6.1 mmol) and n-tributyltin hydride (16.5 ml, 61.4 mmol), and stirred at 80° C. under nitrogen gas flow for 30 minutes. After the reaction was completed, the toluene was evaporated, and the residue was purified by silica gel column chromatography (eluent; ethyl acetate-n-hexane mixed solvent) to afford 14.57 g of a novel substance, 6-methoxy-2-methylthio-9-[2',5'-bis(O-tert-butyldimethylsilyl)-3'-deoxy-β-D-ribofuranosyl]-7-deazapurine (Compound 26, yield; 87.9%).

143 mg of octynyl)-3'-deoxyadenosine-5'-triphosphate (Compound 22) was obtained (yield; 35%).

Reference Example 28
Synthesis of 7-iodo-6-methoxy-2-methylthio-9-[2',5'-bis(O-tert-butyldimethylsilyl)-3'-deoxy-β-D-ribofuranosyl]-7-deazapurine (Compound 27)

6-Methoxy-2-methylthio-9-[2',5'-bis(O-tert-butyldimethylsilyl)-3'-deoxy-β-D-ribofuranosyl]-7-deazapurine (Compound 26, 15.57 g, 28.84 mmol) was dissolved in DMF, added with N-iodosuccinimide (7.79 g, 34.61 mmol), and stirred at room temperature for five hours under nitrogen gas flow while shielded from light. After the reaction was completed, the reaction mixture was cooled to 0° C., and added with ethyl acetate and water, and the organic layer was washed with 5% sodium thiosulfate solution, saturated sodium hydrogencarbonate solution, and saturated saline. The ethyl acetate layer was dried over anhydrous magnesium sulfate, and the ethyl acetate was evaporated. The residue was purified by silica gel column chromatography (eluent; chloroform-n-hexane mixed solvent) to afford 19.06 g of a novel substance, 7-iodo-6-methoxy-2-methylthio-9-[2',5'-bis(O-tert-butyldimethylsilyl)-3'-deoxy-β-D-ribofuranosyl]-7-deazapurine (Compound 27, yield; 99.3%).

$^1$H-NMR (270 MHz, DMSO-$d_6$) δ ppm: −0.10, −0.06, 0.12, 0.13 (4s, 12H, 4MeSi), 0.80, 0.93 (2s, 18H, 2t-Bu), 1.90–2.10 (m, 1H, 3'-Ha), 2.18–2.28 (m, 1H, 3'-Hb), 2.54 (s, 3H, SMe), 3.72 (dd, 1H, J=2.7, 11.6 Hz, 5'-Ha), 3.94 (dd, 1H, J=2.2, 11.6 Hz, 5'-Hb), 4.03 (s, 3H, OMe), 4.32–4.48 (m, 2H, 2'-H, 4'-H), 6.07 (d, 1H, J=3.0 Hz, 1'-H), 7.59 (s, 1H, 8-H)

Reference Example 29
Synthesis of 7-iodo-2-methylthio-9-[2',5'-bis(O-tert-butyldimethylsilyl)-3'-deoxy-β-D-ribofuranosyl]-7-deazapurin-6-one (Compound 28)

4-Thiocresol (3.36 g, 27.0 mmol) was dissolved in methanol, and added with sodium methoxide (1.61 g, 29.7 mmol), and the methanol was evaporated after stirring for five minutes. This residue was added with 7-iodo-6-methoxy-2-methylthio-9-[2',5'-bis(O-tert-butyldimethylsilyl)-3'-deoxy-β-D-ribofuranosyl]-7-deazapurine (Compound 27, 4.00 g, 6 mmol) dissolved in toluene (150 ml) and hexamethylphosphoramide (10 ml, 57.1 mmol), and refluxed under nitrogen gas flow for 4.5 hours. After the reaction was completed, ethyl acetate and water were added to the reaction mixture, and the organic layer was washed with saturated saline. The organic layer was dried anhydrous magnesium sulfate, and concentrated under reduced pressure, and the resulting residue was purified by silica gel column chromatography (eluent; methylene chloride-methanol mixed solvent) to afford 2.35 g of a novel substance, 7-iodo-2-methylthio-9-[2',5'-bis(O-tert-butyldimethylsilyl)-3'-deoxy-β-D-ribofuranosyl]-7-deazapurin-6-one (Compound 28, yield; 59.9%).

$^1$H-NMR (270 MHz, DMSO-d$_6$) δ ppm: 0.06, 0.08, 0.20, 0.24 (4s, 12H, 4MeSi), 0.92, 1.03 (2s, 18H, 2t-Bu), 2.07–2.13 (m, 1H, 3'-Ha), 2.34–2.38 (m, 1H, 3'-Hb), 2.63 (s, 3H, SMe), 3.81–4.05 (m, 2H, 5'-Ha,b), 4.46–4.57 (m, 2H, 2'-H, 4'-H), 6.12 (d, 1H, J=3.0 Hz, 1'-H), 7.47 (s, 1H, 8-H), 12.44 (s, 1H, 1-H)

Reference Example 30

Synthesis of 7-iodo-2',5'-bis(O-tert-butyldimethylsilyl)-3'-deoxy-7-deazaguanosine (Compound 29)

7-Iodo-2-methylthio-9-[2',5'-bis(O-tert-butyldimethylsilyl)-3'-deoxy-β-D-ribofuranosyl]-7-deazapurin-6-one (Compound 28, 2.30 g, 3.53 mmol) was dissolved in methylene chloride (90 ml), cooled to 0° C., added with m-chloroperbenzoic acid (0.96 g, 3.88 mmol), and stirred at 0° C. for 15 minutes and at room temperature for one hour. After the reaction was completed, the reaction mixture was washed with saturated sodium hydrogencarbonate solution and saturated saline, and dried over anhydrous magnesium sulfate, and the methylene chloride was evaporated. The resulting residue was purified by silica gel column chromatography (eluent; chloroform-methanol mixed solvent) to afford 2.02 g of a sulfoxide compound (yield; 83.9%). This compound was dissolved in 1,4-dioxane (20 ml), cooled to −78° C., added with aqueous ammonia (60 ml), and heated to 110° C. for six hours. After the reaction was completed, the reaction mixture was concentrated under reduced pressure, and the resulting residue was purified by silica gel column chromatography (eluent; methylene chloride-methanol mixed solvent) to afford 1.60 g of a novel substance, 7-iodo-2',5'-bis(O-tert-butyldimethylsilyl)-3'-deoxy-7-deazaguanosine (Compound 29, yield; 73.1%).

Reference Example 31

Synthesis of 3'-deoxy-7-iodo-7-deazaguanosine (Compound 30)

7-Iodo-2',5'-bis(O-tert-butyldimethylsilyl)-3'-deoxy-7-deazaguanosine (Compound 29, 1.6 g, 2.58 mmol) was dissolved in THF (50 ml), added with 1 M tetrabutylammonium fluoride (6.2 ml, 6.17 mmol), and stirred at room temperature overnight. After the reaction was completed, the reaction mixture was concentrated under reduced pressure, and the residue was purified by silica gel column chromatography (eluent; chloroform-methanol mixed solvent), and crystallized from methanol to afford 0.80 g of a novel substance, 3'-deoxy-7-iodo-7-deazaguanosine (Compound 30, yield; 79.1%). Melting point: 176–178° C. (decomposition)

$^1$H-NMR (270 MHz, DMSO-d6) δ ppm: 1.81–1.89 (m, 1H, 3'-Ha), 2.10–2.20 (m, 1H, 3'-Hb), 3.43–3.64 (m, 2H, 5'-Ha,b), 4.18–4.29 (m, 2H, 2'-H, 4'-H), 4.91 (t, 1H, J=5.5 Hz, 5'-OH), 5.46 (d, 1H, J=4.3 Hz, 2'-OH), 5.80 (d, 1H, J=2.4 Hz, 1'-H), 6.30 (brs, 2H, 2-NH$_2$), 7.10 (s, 1H, 8-H), 10.45 (brs, 1H, 1-H)

Reference Example 32

Synthesis of 3'-deoxy-7-(6"-trifluoroacetamido-1"-hexynyl)-7-deazaguanosine (Compound 31)

To a solution of 3'-deoxy-7-iodo-7-deazaguanosine (Compound 30, 765 mg, 2.0 mmol) in DMF (10 ml), the 6-trifluoroacetamido-1-hexyne obtained in Reference Example 7 (1.16 g, 6.0 mmol), cuprous (I) iodide (76.4 mg, 0.40 mmol), tetrakis(triphenylphosphine)palladium (0) (226 mg, 0.20 mmol), and triethylamine (0.56 ml, 4.0 mmol) were added under nitrogen gas flow, and allowed to react at room temperature for one hour. The reaction mixture was diluted with methylene chloride-methanol mixture (20 ml), added with ion exchange resin AG1X8 (HCO$_3^-$ type, 2.0 g), and stirred for 30 minutes. After filtration of the reaction mixture, the filtrate was concentrated, and the resulting residue was purified by silica gel column chromatography (eluent; chloroform-methanol mixed solution) to afford 616 mg of a novel substance, 3'-deoxy-7-(6"-trifluoroacetamido-1"-hexynyl)-7-deazaguanosine (Compound 31, yield; 69.5%). Melting point: 185–187° C.

$^1$H-NMR (270 MHz, DMSO-d$_6$) δ ppm: 1.47–1.68 (m, 4H, —(CH$_2$)$_2$—), 1.80–1.88 (m, 1H, 3'-Ha), 2.09–2.19 (m, 1H, 3'-Hb), 2.38 (t, 2H, J=6.9 Hz, CCCH$_2$), 3.25 (q, 2H, J=6.8 Hz, CH$_2$N), 3.42–3.62 (m, 2H, 5'-Ha,b), 4.17–4.30 (m, 2H, 2'-H, 4'-H), 4.90 (t, 1H, J=5.5 Hz, 5'-OH), 5.45 (d, 1H, J=4.3 Hz, 2'-OH), 5.80 (d, 1H, J=2.7 Hz, 1'-H), 6.28 (brs, 2H, 2-NH$_2$), 7.11 (s, 1H, 8-H), 9.42 (brs, 1H, NHTfa), 10.39 (s, 1H, 1-H)

Reference Example 33

Synthesis of 7-deaza-7-(6"-amino1"-hexynyl)-3'-deoxyguanosine-5'-triphosphate (Compound 32)

3'-Deoxy-7-(6"-trifluoroacetamido-1"-hexynyl)-7-deazaguanosine (Compound 31, 133 mg, 0.3 mmol) was dissolved in triethyl phosphate (1.33 ml), cooled to −20° C., added with phosphorus oxychloride (25 μl), and stirred at −20° C. After 30 minutes, the reaction mixture was added with further phosphorus oxychloride (22 μl), and further stirred overnight. This reaction mixture was added to 0.5 M solution of tris(tri-n-butylammonium)pyrophosphate in DMF (3.6 ml) cooled to −20° C., and stirred at room temperature for three hours. After the reaction was completed, the reaction mixture was added with a triethylamine-water mixture (4 ml), washed with ether, and purified by DEAE-Toyopearl ion exchange column chromatography (1.7×30 cm, eluent; triethylammonium hydrogencarbonate buffer (pH 7.5), 0 M→0.6 M linear gradient (total volume; 2 L)). The purified product was added with 25% aqueous ammonia (20 ml), left stand for one hour, and then concentrated under reduced pressure, and the obtained residue was purified again by DEAE-Toyopearl ion exchange column chromatography (1.7×30 cm, eluent; triethylammonium hydrogencarbonate buffer (pH 7.5), 0 M→0.3 M linear gradient (total volume; 1 L)) to afford 108 mg of a novel substance, 7-deaza-7-(6"-amino-1"-hexynyl)-3'-deoxyguanosine-5'-triphosphate (Compound 32, yield; 36.4%).

Example 6

Synthesis of R110-labeled 7-deaza-3'-deoxyguanosine-5'-triphosphate (a compound of general formula [I] where V is —C≡C— and n=4)

7-Deaza-7-(6"-amino-1"-hexynyl)-3'-deoxyguanosine-5'-triphosphate (Compound 32, 8 μmol) and 5-carboxyrhodamine-110-bis-trifluoroacetate succinimide ester (Molecular Probe, 15 μmol) were dissolved in DMF (500 μl) and water (250 μl), added with triethylamine (0.16 ml) and pyridine (0.29 ml), and stirred overnight. The reaction mixture was diluted with water (30 ml), and purified by DEAE-Toyopearl ion exchange column chromatography (1.7×30 cm, eluent; triethylammonium hydrogencarbonate buffer (pH 7.5), 0.1 M→0.8 M linear gradient (total volume; 1 L)) to afford 3.38 μmol (yield; 42.3%) of R110-labeled 7-deaza-3'-deoxyguanosine-5'-triphosphate represented by the following formula [a compound of the general formula [I] where V is —C≡C— and n=4, abbreviated as R110-3'dGTP(n4) hereinafter].

solution) to afford 918 mg of 3'-deoxy-5-(3"-trifluoroacetamido-1"-propynyl)uridine (yield; 55.3%).

¹H-NMR (270 MHz, DMSO-d₆) δ ppm: 1.89–1.92 (m, 1H, 3'-Ha), 2.17–2.26 (m, 1H, 3'-Hb), 3.53, 3.76 (2dd, 2H, J=3.1, 11.9; 2.7, 12.1 Hz, 5'-Ha,b), 4.22–4.30 (m, 4H, 2'-H, 4'-H, —CH₂—), 5.20 (brs, 1H, 5'-OH), 5.52 (d, 1H, J=4.0 Hz, 2'-OH), 5.75 (d, 1H, J=1.9 Hz, 1'-H), 8.34 (s, 1H, 6-H), 10.06 (t, 1H, J=5.4 Hz, NHTfa), 11.67 (s, 1H, NH)

Reference Example 36
Synthesis of 5-(3"-amino-1"-propynyl)-3'-deoxyuridine-5'-triphosphate 3'-Deoxy-5-(3"-trifluoroacetamido-1"-propynyl)uridine (42 mg, 0.11 mmol) was dissolved in triethyl phosphate (1.13 ml), cooled to −20° C., then added with phosphorus oxychloride (25 μl), and stirred at −20° C. After 30 minutes,

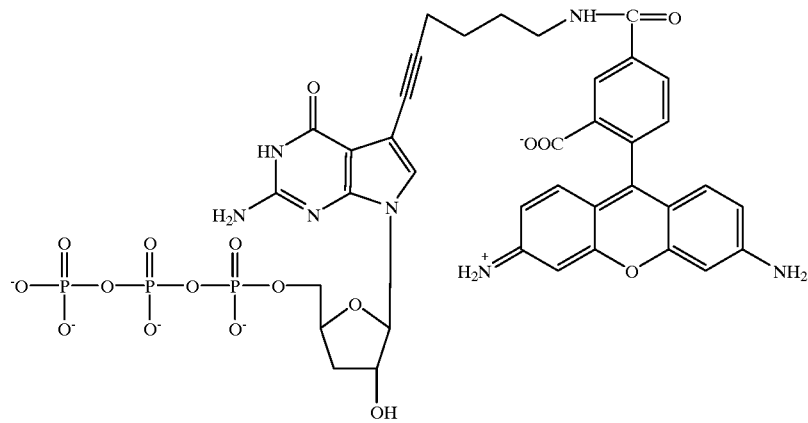

Figure 7:
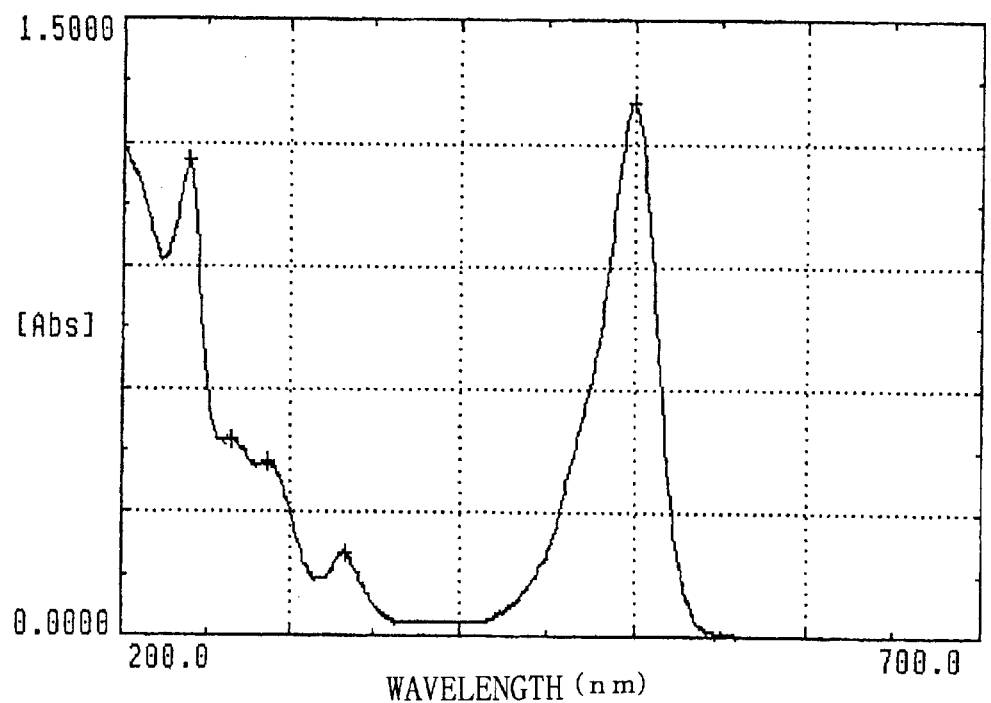
FIG. 7 shows the result of UV-visible region spectrophotometry of the carboxyrhodamine-110-labeled 7-deaza-3'-deoxyguanosine-5'-triphosphate (a compound of general formula [I] where V is —C≡C— and n=4) obtained in Example 6.

The absorption spectrum for UV-visible region resulting from spectroscopy of the obtained R110-3'dGTP (n4) (measurement wavelength; 700 nm to 200 nm, reference; distilled water) performed by using DU640 UV-visible region spectrophotometer [Beckman] is shown in FIG. 7.

Reference Example 34
Synthesis of N-propargyltrifluoroacetamide

Propargylamine (Aldrich, 25 g, 0.45 mol) was added dropwise to methyl trifluoroacetate (Tokyo Chemical Industry Co., Ltd., 69.2 g, 0.54 mol) cooled to 0° C. They were allowed to react at 0° C. for two hours to afford 43.8 g (86.0%) of N-propargyltrifluoroacetamide after purification by vacuum distillation (23 mmHg, boiling point; 77° C.).

Reference Example 35
Synthesis of 3'-deoxy-5-(3"-trifluoroacetamido-1"-propynyl)uridine To a solution of 3'-deoxy-5-iodouridine (Compound 2, 1.56 g, 4.4 mmol) in DMF (22 ml), the N-propargyltrifluoroacetamide obtained in Reference Example 34 (1.54 ml, 13.2 mmol), cuprous (I) iodide (168 mg, 0.88 mmol), tetrakis(triphenylphosphine)palladium (0) (508 mg, 0.44 mmol), and triethylamine (1.23 ml, 8.8 mmol) were added under nitrogen gas flow, and allowed to react at room temperature for four hours. The reaction mixture was concentrated under reduced pressure, and the resulting residue was dissolved in a methylene chloride-methanol mixture (40 ml), added with ion exchange resin AG1X8 (Biolad, HCO₃⁻ type, 4 g), and stirred for 30 minutes. After filtration of the reaction mixture, the filtrate was concentrated, and the resulting residue was purified by silica gel column chromatography (eluent; methylene chloride-methanol mixed the reaction mixture was added with further phosphorus oxychloride (22 μl), and stirred for further five hours. This reaction mixture was added to 0.5 M solution of the tris(tri-n-butylammonium)pyrophosphate obtained in Reference Example 4 in DMF (3.6 ml) cooled to −20° C., and stirred at room temperature for two hours. After the reaction was completed, the reaction mixture was added with a triethylamine-water mixture (4 ml), left stand overnight, added with 25% aqueous ammonia (20 ml), and left stand for four hours. The reaction mixture was washed with ether, and concentrated to dryness, and the obtained residue was purified by DEAE-Toyopearl ion exchange column chromatography (Tosoh Corporation, 1.2×30 cm, eluent; triethylammonium hydrogencarbonate buffer (pH 7.5), 0 M→0.3 M linear gradient (total volume; 1 L)) to afford 115 mg of 5-(3"-amino-1"-propynyl)-3'-deoxyuridine-5'-triphosphate (yield; 41.3%).

Reference Example 37
Synthesis of TMR-labeled 3'-deoxyuridine-5'-triphosphate (a compound of the general formula [I] where V is —C≡C— and n=1)

A solution of 5-carboxytetramethylrhodamine succinimide ester (Molecular Probe, 15 mg) in DMF (0.9 ml) was added to 5-(3"-amino-1"-propynyl)-3'-deoxyuridine-5'-triphosphate (10.5 μmol) in 1 M triethylammonium hydrogencarbonate buffer (pH 9.05, 1.2 ml), and stirred at room temperature overnight. The reaction mixture was diluted with water (30 ml), and purified by DEAE-Toyopearl ion exchange column chromatography (1.2×30 cm, eluent; triethylammonium hydrogencarbonate buffer (pH7.5), 0.05 M→0.7 M linear gradient (total volume; 2 L)) to afford 7.38 μmol (yield; 70.2%) of TMR-labeled 3'-deoxyuridine-5'- triphosphate [a compound of the general formula [I] where n=1, abbreviated as TMR-3'dUTP(n1) hereinafter].

Reference Example 38

Synthesis of 3'-deoxy-5-(3"-trifluoroacetamido-1"-propynyl)cytidine

To a solution of 3'-deoxy-5-iodocytidine (Compound 6, 1.0 g, 2.83 mmol) in DMF (14 ml), the N-propargyltrifluoroacetamide obtained in Reference Example 2 (0.99 ml, 8.50 mmol), cuprous (I) iodide (108 mg, 0.566 mmol), tetrakis(triphenylphosphine)palladium (0) (327 mg, 0.283 mmol), and triethylamine (0.8 ml, 5.66 mmol) were added under nitrogen gas flow, and allowed to react at room temperature for 30 minutes. The reaction mixture was diluted with a methylene chloride-methanol mixture (25 ml), added with ion exchange resin AG1X8 ($HCO_3^-$ type, 2.6 g), and stirred for 30 minutes. After filtration of the reaction mixture, the filtrate was concentrated, and the resulting residue was purified by silica gel column chromatography (eluent; methylene chloride-methanol mixed solution) to afford 879 mg of 3'-deoxy-5-(3"-trifluoroacetamido-1"-propynyl)cytidine (yield; 82.5%).

$^1$H-NMR (270 MHz, DMSO-$d_6$) δ ppm: 1.64–1.71 (m, 1H, 3'-Ha), 1.86–1.96 (m, 1H, 3'-Hb), 3.52–3.57 (m, 1H, 5'-Ha), 3.79–3.83 (m, 1H, 5'-Hb), 4.14–4.28 (m, 4H, 2'-H, 4'-H, —CH$_2$—), 5.18 (t, 1H, J=5.0Hz, 5'-OH), 5.53 (d, 1H, J=3.8 Hz, 2'-OH), 5.63 (s, 1H, 1'-H), 6.76 (brs, 1H, NH$_2$a), 7.74 (brs, 1H, NH$_2$b), 8.38 (s, 1H, 6-H), 9.93 (brs, 1H, NHTfa)

Reference Example 39

Synthesis of 5-(3"-amino1"-propynyl)-3'-deoxycytidine-5'-triphosphate

3'-Deoxy-5-(3"-trifluoroacetamido-1"-propynyl) cytidine (113 mg, 0.3 mmol) was dissolved in triethyl phosphate (1.13 ml), cooled to –20° C., added with phosphorus oxychloride (25 μl), and stirred at –20° C. After 30 minutes, the reaction mixture was added with further phosphorus oxychloride (22 μl), and stirred for further five hours. This reaction mixture was added to 0.5 M solution of the tris(tri-n-butylammonium)pyrophosphate obtained in Reference Example 4 in DMF (3.6 ml) cooled to –20° C., and stirred at room temperature for two hours. After the reaction was completed, the reaction mixture was added with a triethylamine-water mixture (4 ml), left overnight, then added with 25% aqueous ammonia (20 ml), and left stand for four hours. The reaction mixture was washed with ether, and concentrated to dryness, and the resulting residue was purified by DEAE-Toyopearl ion exchange column chromatography (1.2×30 cm, eluent; triethylammonium hydrogencarbonate buffer (pH 7.5), 0 M→0.3 M linear gradient (total volume; 1 L)) to afford 115 mg of 5-(3"-amino-1"-propynyl)-3'-deoxycytidine-5'-triphosphate (yield; 41.3%).

Reference Example 40

Synthesis of XR-labeled 3'-deoxycytidine-5'-triphosphate (a compound of the general formula [I] where V is —C≡C— and n=1)

To 5-(3"-amino-1"-propynyl)-3'-deoxycytidine-5'-triphosphate (8 μmol) dissolved in 1 M triethylammonium hydrogencarbonate buffer (pH 9.05, 0.4 ml), a solution of 5-carboxy-X-rhodamine succinimide ester (Molecular Probe, 15 mg) in DMF (0.9 ml) was added, and stirred at room temperature overnight. The reaction mixture was diluted with water (30 ml), and purified by DEAE-Toyopearl ion exchange column chromatography (1.2×30 cm, eluent; triethylammonium hydrogencarbonate buffer (pH 7.5), 0.1 M→0.7 M linear gradient (total volume; 2 L)) to afford 2.93 μmol (yield; 36.6%) of XR-labeled 3'-deoxycytidine-5'-triphosphate [a compound of the general formula [I] where V is —C≡C— and n=1, abbreviated as XR-3'dCTP(n1) hereinafter].

Reference Example 41

Synthesis of 7-deaza-7-(3"-trifluoroacetamido-1"-propynyl)-3'-deoxyadenosine

To a solution of 7-iodo-3'-deoxy-7-deazaadenosine (Compound 18, 0.5 g, 1.33 mmol) in DMF (6.7 ml), the N-propargyltrifluoroacetamide obtained in Reference Example 34 (0.47 ml, 3.99 mmol), cuprous (I) iodide (51 mg, 0.266 mmol), tetrakis(triphenylphosphine)palladium (0) (154 mg, 0.133 mmol), and triethylamine (0.37 ml, 2.66 mmol) were added under nitrogen gas flow, and allowed to react at room temperature for 30 minutes. The reaction mixture was diluted with a methylene chloride-methanol mixture (12 ml), added with ion exchange resin AG1X8 ($HCO_3^-$ type, 1.22 g), and stirred for 30 minutes. After filtration of the reaction mixture, the filtrate was concentrated, and the resulting residue was purified by silica gel column chromatography (eluent; methylene chloride-methanol mixed solution) to afford 436 mg of 7-deaza-7-(3"-trifluoroacetamido-1"-propynyl)-3'-deoxyadenosine (yield; 82.3%).

$^1$H-NMR (270 MHz, DMSO-$d_6$) δ ppm: 1.83–1.91 (m, 1H, 3'-Ha), 2.14–2.24 (m, 1H, 3'-Hb), 3.48–3.56 (m, 1H, 5'-Ha), 3.66–3.73 (m, 1H, 5'-Hb), 4.30–4.35 (m, 4H, 2'-H, 4'-H, —CH$_2$—), 5.08 (t, 1H, J=5.5 Hz, 5'-OH), 5.59 (d, 1H, J=3.8 Hz, 2'-OH), 6.02 (d, 1H, J=2.2 Hz, 1'-H), 6.80 (brs, 2H, NH$_2$), 7.79 (s, 1H, 8-H), 8.12 (s, 1H, 2-H), 10.08 (brs, 1H, NHTfa)

Reference Example 42

Synthesis of 7-deaza-7-(3"-amino-1"-propynyl)-3'-deoxyadenosine-5'-triphosphate

7-Deaza-7-(3"-trifluoroacetamido-1"-propynyl)-3'-deoxyadenosine (120 mg, 0.3 mmol) was dissolved in triethyl phosphate (1.2 ml), cooled to –20° C., added with phosphorus oxychloride (25 μl), and stirred at –20° C. After 30 minutes, the reaction mixture was added with further phosphorus oxychloride (22 μl), and stirred for further four hours. This reaction mixture was added to 0.5 M solution of the tris(tri-n-butylammonium)pyrophosphate obtained in Reference Example 4 in DMF (3.6 ml) cooled to –20° C., and stirred at room temperature for three hours. After the reaction was completed, the reaction mixture was added with a triethylamine-water mixture (4 ml), left stand overnight, added with 25% aqueous ammonia (20 ml), and left stand for four hours. The reaction mixture was washed with ether, and concentrated to dryness, and the obtained residue was purified by DEAE-Toyopearl ion exchange column chromatography (1.2×30 cm, eluent; triethylammonium hydrogencarbonate buffer (pH 7.5), 0 M→0.3 M linear gradient (total volume; 1 L)) to afford 114 mg of 7-deaza-7-(3'-amino-1"-propynyl)-3'-deoxyadenosine-5'-triphosphate (yield; 39.9%).

Reference Example 43

Synthesis of R6G-labeled 7-deaza-3'-deoxyadenosine-5'-triphosphate (a compound of the general formula [I] where V is —C≡C— and n=1)

To 7-deaza-7-(3"-amino-1"-propynyl)-3'-deoxyadenosine-5'-triphosphate (8 μmol) dissolved in 1 M triethylammonium hydrogencarbonate buffer (pH 9.05, 0.4 ml), a solution of 5-carboxyrhodamine-6G succinimide ester (Molecular Probe, 14.5 mg) in DMF (0.8 ml) were added, and stirred at room temperature overnight. The reaction mixture was diluted with water (30 ml), and purified by DEAE-Toyopearl ion exchange column chromatography (1.2×30 cm, eluent; triethylammonium hydrogencarbonate buffer (pH 7.5), 0.1 M→0.6 M linear gradient (total volume; 2 L)) to afford 2.54 μmol (yield; 31.7%) of R6G-labeled 7-deaza-3'-deoxyadenosine-5'-triphosphate [a compound of the general formula [I] where V is —C≡C— and n=1, abbreviated as R6G-3'dATP(n1) hereinafter].

Reference Example 44

Synthesis of 3'-deoxy-7-(3"-trifluoroacetamido-1"-propynyl)-7-deazaguanosine

To a solution of 3'-deoxy-7-iodo-7-deazaguanosine (Compound 30, 0.65 g, 1.7 mmol) in DMF (8.5 ml), the N-propargyltrifluoroacetamide obtained in Reference Example 34 (0.58 ml, 5.0 mmol), cuprous (I) iodide (63 mg, 0.33 mmol), tetrakis(triphenylphosphine)palladium (0) (192 mg, 0.17 mmol), and triethylamine (0.46 ml, 3.31 mmol) were added under nitrogen gas flow, and allowed to reacted at room temperature for one hour. The reaction mixture was diluted with a methylene chloride-methanol mixture (16 ml), added with ion exchange resin AG1X8 ($HCO_3^-$ type, 1.6 g), and stirred for 30 minutes. After filtration of the reaction mixture, the filtrate was concentrated, and the resulting residue was purified by silica gel column chromatography (eluent; chloroform-methanol mixed solution) to afford 485 mg of 3'-deoxy-7-(3"-trifluoroacetamido-1"-propynyl)-7-deazaguanosine (yield; 70.5%).

$^1$H-NMR (270 MHz, DMSO-$d_6$) δ ppm: 1.81–1.91 (m, 1H, 3'-Ha), 2.10–2.21 (m, 1H, 3'-Hb), 3.42–3.68 (m, 2H, 5'-Ha,b), 4.22–4.30 (m, 4H, 2'-H, 4'-H, —$CH_2$—), 4.94 (t, 1H, J=5.5 Hz, 5'-OH), 5.49 (d, 1H, J=4.3 Hz, 2'-OH), 5.81 (d, 1H, J=2.4 Hz, 1'-H), 6.32 (brs, 2H, 2-$NH_2$), 7.27 (s, 1H, 8-H), 10.05 (brs, 1H, NHTfa), 10.50 (brs, 1H, 1-H)

Reference Example 45

Synthesis of 7-deaza-7-(3"-amino-1"-propynyl)-3'-deoxyguanosine-5'-triphosphate

3'-Deoxy-7-(3"-trifluoroacetamido-1"-propynyl)-7-deazaguanosine (125 mg, 0.3 mmol) was dissolved in triethyl phosphate (1.25 ml), cooled to −20° C., added with phosphorus oxychloride (25 μl), and stirred at −20° C. After 30 minutes, the reaction mixture was added with further phosphorus oxychloride (22 μl), and further stirred overnight. This reaction mixture was added to 0.5 M solution of the tris(tri-n-butylammonium)pyrophosphate obtained in Reference Example 4 in DMF (3.6 ml) cooled to −20° C., and stirred at room temperature for three hours. After the reaction was completed, the reaction mixture was added with a triethylamine-water mixture (4 ml), washed with ether, and purified by DEAE-Toyopearl ion exchange column chromatography (1.2×30 cm, eluent; triethylammonium hydrogencarbonate buffer (pH 7.5), 0 M→0.6 M linear gradient (total volume; 2 L)). The purified product was added with 25% aqueous ammonia (15 ml), and left stand for one hour, and then concentrated under reduced pressure, and the obtained residue was purified again by DEAE-Toyopearl ion exchange column chromatography (1.2×30 cm, eluent; triethylammonium hydrogencarbonate buffer (pH 7.5), 0 M→0.3 M linear gradient (total volume; 1 L)) to afford 75 mg of 7-deaza-7-(3"-amino1"-propynyl)-3'-deoxyguanosine-5'-triphosphate (yield; 25.9%).

Reference Example 46

Synthesis of R110-labeled 7-deaza-3'-deoxyguanosine-5'-triphosphate (a compound of the general formula [I] where V is —C≡C— and n=1)

7-Deaza-7-(3"-amino-1"-propynyl)-3'-deoxyguanosine-5'-triphosphate (10.5 μmol) and 5-carboxyrhodamine-110-bis-trifluoroacetate succinimide ester (Molecular Probe, 31.5 mg) were dissolved in DMF (0.49 ml) and water (0.23 ml), added with triethylamine (0.16 ml) and pyridine (0.29 ml), and stirred overnight. The reaction mixture was diluted with water (30 ml), and purified by DEAE-Toyopearl ion exchange column chromatography (1.2×30 cm, eluent; triethylammonium hydrogencarbonate buffer (pH 7.5), 0.1 M→0.8 M linear gradient (total volume; 1 L)) to afford 3.67 μmol (yield; 34.9%) of R110-labeled 7-deaza-3'-deoxyguanosine-5'-triphosphate [a compound of the general formula [I] where V is —C≡C— and n=1, abbreviated as R110–3'dGTP(n1) hereinafter].

Example 7

Synthesis of R110-labeled 3'-deoxycytidine-5'-triphosphate (a compound of the general formula [I] where V is —C≡C— and n=4)

To 5-(6"-amino-1"-hexynyl)-3'-deoxycytidine-5'-triphosphate (Compound 8, 8 μmol) dissolved in a mixture of DMF (400 μl) and water (200 μl), triethylamine (20 μl) and 5-carboxyrhodamine-110-bis-trifluoroacetate succinimide ester (Molecular Probe, 21 μmol) were added, and stirred at room temperature overnight. The reaction mixture was diluted with water (30 ml), and purified by DEAE-Toyopearl ion exchange column chromatography (1.7×15 cm, eluent; triethylammonium hydrogencarbonate buffer (pH 7.5), 0.1 M→0.8 M linear gradient (total volume; 1 L)) to afford 5.83 μmol (yield; 72.9%) of R110-labeled 3'-deoxycytidine-5'-triphosphate represented by the following formula [a compound of the general formula [I] where V is —C≡C— and n=4, abbreviated as R110-3'dCTP(n4) hereinafter].

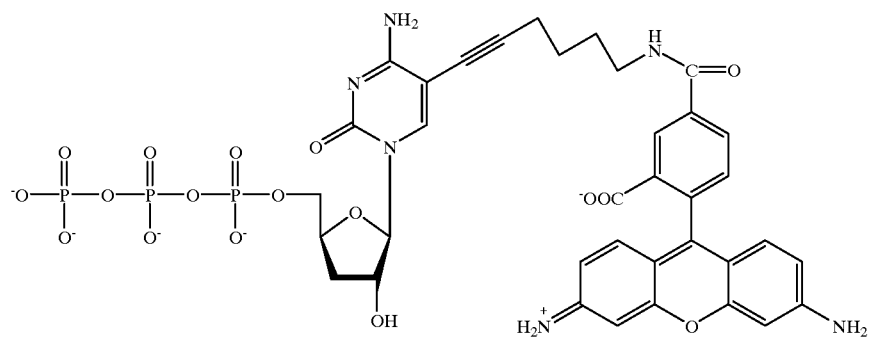

The absorption spectrum for UV-visible region resulting from spectroscopy of the obtained R110-3'dCTP(n4)

Figure 8:
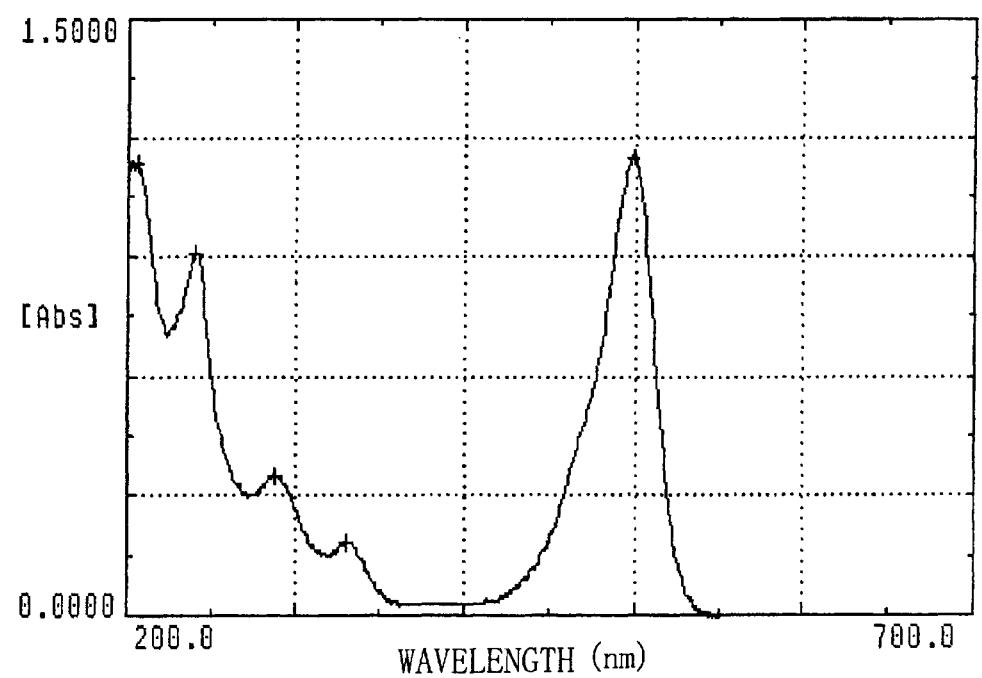
FIG. 8 shows the result of UV-visible region spectrophotometry of the carboxyrhodamine-110-labeled 3'-deoxycytidine-5'-triphosphate (a compound of the general formula [I] where V is —C≡C— and n=4) obtained in Example 7.

(measurement wavelength; 700 nm to 200 nm, reference; distilled water) performed by using DU640 UV-visible region spectrophotometer [Beckman] is shown in FIG. 8.

Example 8

Synthesis of R6G-labeled 3'-deoxycytidine-5'-triphosphate (a compound of the general formula [I] where V is —C≡C— and n=4)

To 5-(6"-amino-1"-hexynyl)-3'-deoxycytidine-5'-triphosphate (Compound 8, 8 μmol) dissolved in a mixture of DMF (2.9 ml) and water (0.9 ml), triethylamine (20 μl), and 6-carboxyrhodamine-6G succinimide ester (Molecular Probe, 16 μmol) were added, and stirred at room temperature overnight. The reaction mixture was diluted with water (30 ml), and purified by DEAE-Toyopearl ion exchange column chromatography (1.7×15 cm, eluent; triethylammonium hydrogencarbonate buffer (pH 7.5), 0.1 M→0.7 M linear gradient (total volume; 1 L)) to afford 5.83 μmol (yield; 43.1%) of R6G-labeled 3'-deoxycytidine-5'-triphosphate represented by the following formula [a compound of the general formula [I] where n=4, abbreviated as R6G-3'dCTP(n4) hereinafter].

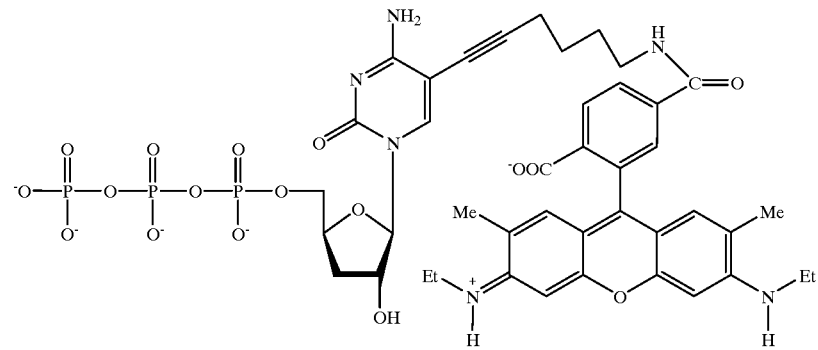

In the formula, Et represents an ethyl group, and Me represents a methyl group.

The absorption spectrum for UV-visible region resulting from spectroscopy of the obtained R6G-3'dCTP(n4)

Figure 9:
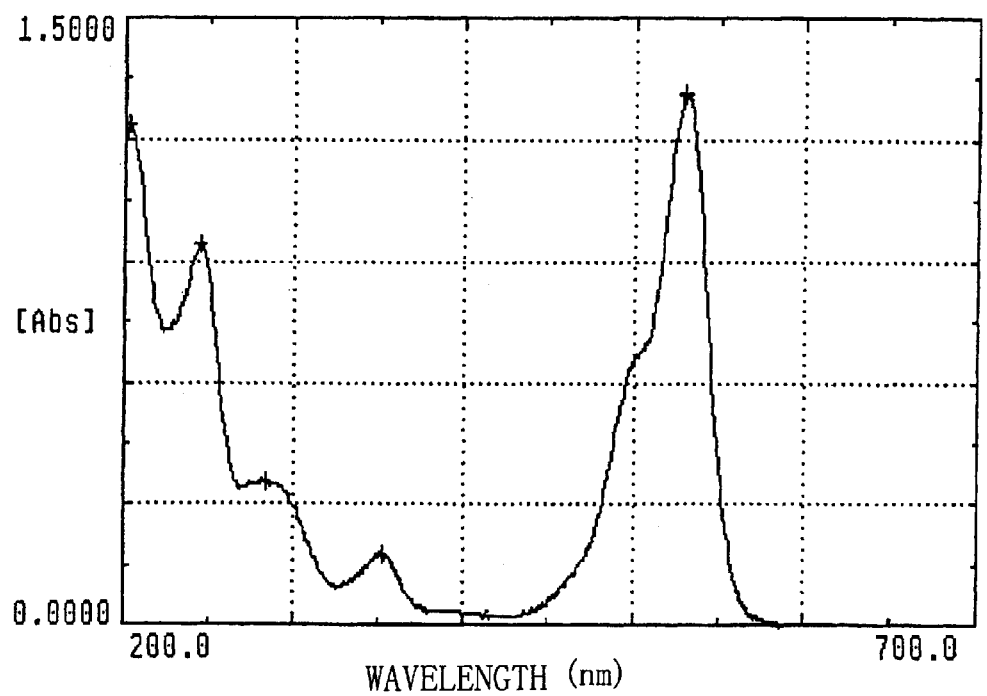
FIG. 9 shows the result of UV-visible region spectrophotometry of the carboxyrhodamine-6G-labeled 3'-deoxycytidine-5'-triphosphate (a compound of the general formula [I] where V is —C≡C— and n=4) obtained in Example 8.

(measurement wavelength; 700 nm to 200 nm, reference; distilled water) performed by using DU640 UV-visible region spectrophotometer [Beckman] is shown in FIG. 9.

Example 9

Synthesis of XR-labeled 7-deaza-3'-deoxyadenosine-5'-triphosphate (a compound of the general formula [I] where V is —C≡C— and n=4)

To 7-deaza-7-(6"-amino-1"-hexynyl)-3'-deoxyadenosine-5'-triphosphate (Compound 20, 8 μmol) dissolved in a mixture of DMF (400 μl) and water (400 μl), triethylamine (20 μl) and 6-carboxy-X-rhodamine succinimide ester (Molecular Probe, 22 μmol) were added, and stirred at room temperature overnight. The reaction mixture was diluted with water (30 ml), and purified by DEAE-Toyopearl ion exchange column chromatography (1.7×15 cm, eluent; triethylammonium hydrogencarbonate buffer (pH 7.5), 0.1 M→0.6 M linear gradient (total volume; 1 L)) to afford 4.39 μmol (yield; 54.8%) of XR-labeled 7-deaza-3'-deoxyadenosine-5'-triphosphate represented by the following formula [a compound of the general formula [I] where V is —C≡C— and n=4, abbreviated as XR-3'dATP(n4) hereinafter].

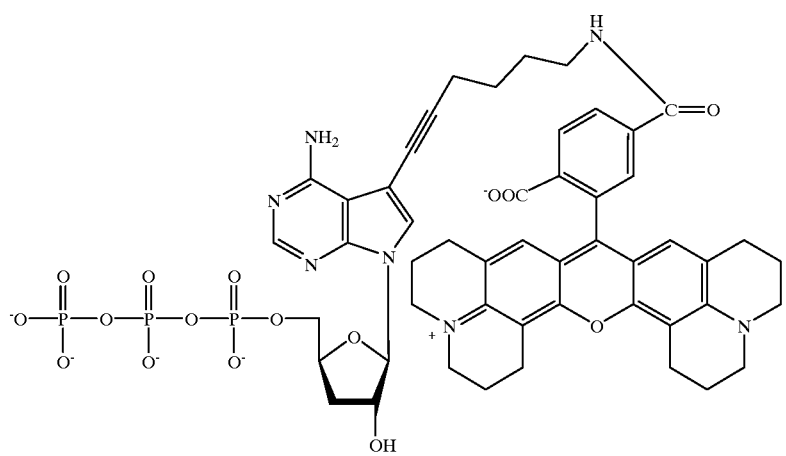

Figure 10:
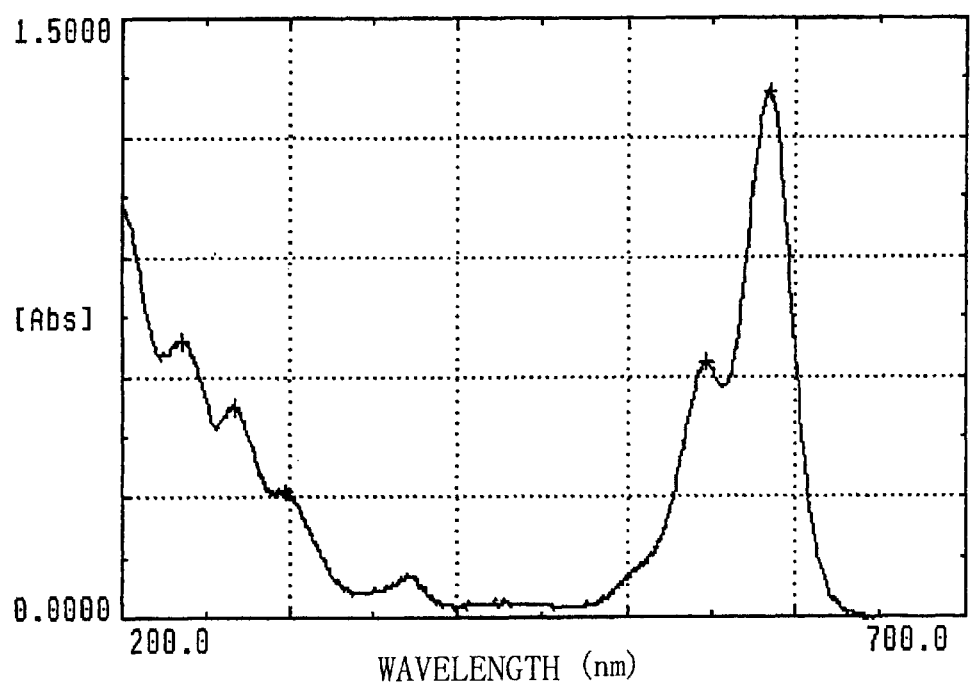
FIG. 10 shows the result of UV-visible region spectrophotometry of the carboxyrhodamine-X-labeled 7-deaza-3'-deoxyadenosine-5'-triphosphate (a compound of the general formula [I] where V is —C≡C— and n=4) obtained in Example 9.

The absorption spectrum for UV-visible region resulting from spectroscopy of the obtained XR-3'dATP(n4) (measurement wavelength; 700 nm to 200 nm, reference; distilled water) performed by using DU640 UV-visible region spectrophotometer [Beckman] is shown in FIG. 10.

Example 10
Synthesis of XR-labeled 7-deaza-3'-deoxyguanosine-5'-triphosphate (a compound of the general formula [I] where V is —C≡C— and n=4)

7-Deaza-7-(6"-amino-1"-hexynyl)-3'-deoxyguanosine-5'-triphosphate (Compound 32, 8 μmol) and 5-carboxy-X-rhodamine succinimide ester (Molecular Probe, 19 μmol) were dissolved in DMF (400 μl) and water (200 μl), added with triethylamine (20 μl), and stirred overnight. The reaction mixture was diluted with water (30 ml), and purified by DEAE-Toyopearl ion exchange column chromatography (1.7×15 cm, eluent; triethylammonium hydrogencarbonate (pH 7.5), 0.1 M→0.8 M linear gradient (total volume; 1 L)) to afford 2.68 μmol (yield; 33.5%) of XR-labeled 7-deaza-3'-deoxyguanosine-5'-triphosphate represented by the following formula [a compound of the general formula [I] where V is —C≡C— and n=4, abbreviated as XR-3'dGTP(n4) hereinafter].

R6G-3'dATP(n6) (the compound of Example 4)
R6G-3'dATP(n1) (the compound of Reference Example 43)
TMR-3'dUTP(n4) (the compound of Example 5)
TMR-3'dUTP(n1) (the compound of Reference Example 37)
R110-3'dGTP(n4) (the compound of Example 6)
R110-3'dGTP(n1) (the compound of Reference Example 46)

[Experimental procedure]

Atemplate DNA (1 μg) was added to a sample tube containing terminators, guanosine-5'-triphosphate (rGTP), uridine-5'-triphosphate (rUTP), adenosine-5'-triphosphate (rATP), and cytidine-5'-triphosphate (rCTP), MgCl$_2$, spermidine-(HCl)$_3$, dithiothreitol (DTT), Tris/HCl (pH 7.5) and T7 RNA polymerase in such amounts as their final concentrations should be as follows, and filled up to 10 μl with distilled water, which was used as a sample.

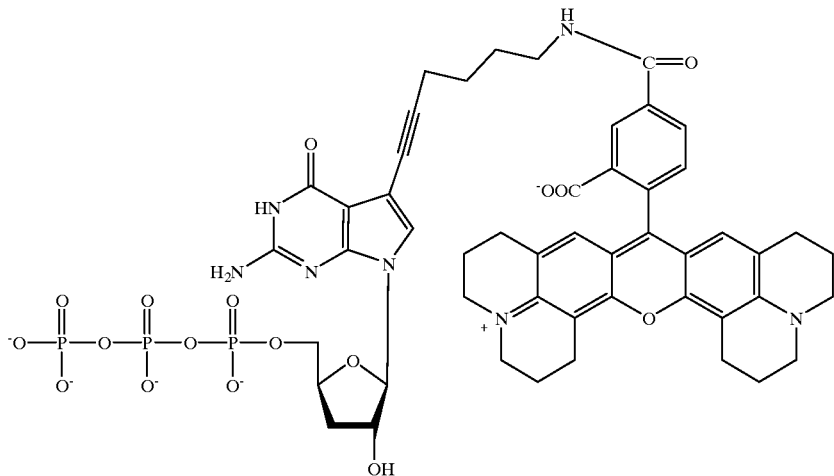

Figure 11:
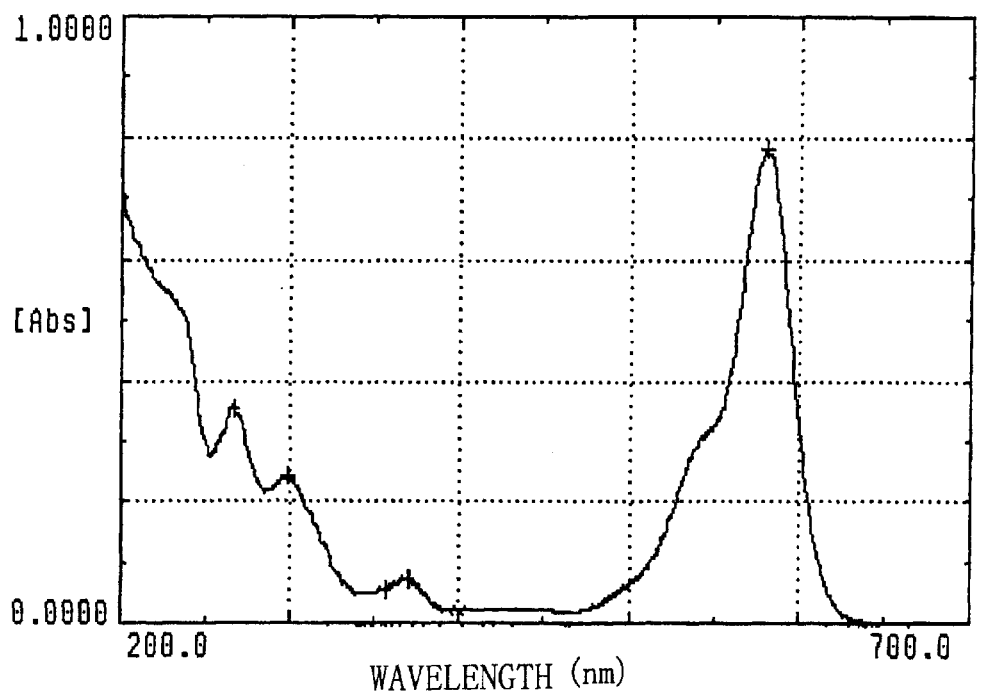
FIG. 11 shows the result of UV-visible region spectrophotometry of the carboxyrhodamine-X-labeled 7-deaza-3'-deoxyguanosine-5'-triphosphate (a compound of the general formula [I] where V is —C≡C— and n=4) obtained in Example 10.

The absorption spectrum for UV-visible region resulting from spectroscopy of the obtained XR-3'dGTP(n4) (measurement wavelength; 700 nm to 200 nm, reference; distilled water) performed by using DU640 UV-visible region spectrophotometer [Beckman] is shown in FIG. 11.

Experimental Example 1
Evaluation of incorporation rates of 3'-deoxyterminators with different linker chain lengths This evaluation was based on the method described in Proc. Natl. Acad. Sci. USA Vol. 86, pp.4076–4080, June 1989.

[Template DNA]
  pBSKS(+)/pvuII (Stratagene)
[Terminator]
  XR-3'dCTP(n4) (the compound of Example 1)
  XR-3'dCTP(n6) (the compound of Example 2)
  XR-3'dCTP(n1) (the compound of Reference Example 40)
  XR-3'dCTP(n3) (the compound of Reference Example 6)
  R6G-3'dATP(n4) (the compound of Example 3)

(Concentration)

| • Terminater | |
|---|---|
| XR-3'dCTP | 1 μM |
| R6G-3'dATP | 20 μM |
| TMR-3'dUTP | 10 μM |
| R110-3'dGTP | 1 μM |
| • rGTP | 500 μM |
| • rUTP | 500 μM |
| • rATP | 250 μM |
| • rCTP | 250 μM |
| • MgCl$_2$ | 5–10 mM |
| • Spermidine-(HCl)$_3$ | 2 mM |
| • DTT | 10 μmM |
| • Tris/HCl (pH 7.5) | 40 mM |
| • T7 RNA polymerase | 25 units/10 μl |

After 1 hour incubation of the sample at 37° C., the terminators not incorporated were removed by gel filtration, and the precipitates were collected by centrifugal separation. Subsequently, the precipitates were dissolved in 3 μg of formamide dye (10 mM EDTA containing 95% formamide), and heated to 80° C. for five minutes. After cooling, 1.5 µl of the solution was applied to 4% sequencing gel, and electrophoresed by ABI377 fluorescence automatic sequencer (ABI) for five hours. The final signals (bases) on the gel images of the sequencer were determined, and final base/terminator concentration was calculated as incorporation rates, and compared. The results were shown in Table 1.

TABLE 1

| Value of n in the general formula [I] | 1 | 3 | 4 | 6 |
|---|---|---|---|---|
| XR-3' dCTP | 1 | 1 | 50 | 50 |
| R6G-3' dATP | 1 | — | 10 | 10 |
| TMR-3' dUTP | 1 | — | 2 | — |
| R110-3' dGTP | 1 | — | 2 | — |

*The values in the table are represented as relative incorporation rates obtained from actual measured values of the final bases when the incorporation rate for n = 1 is normalized to 1

[Results]

As seen from Table 1, it was found that, for XR-3'dCTP and R6G-3'dATP, those of n=4 and 6 exhibited markedly improved incorporation rates in comparison with those of n=1. Also for TMR-3'dUTP and R110-3'dGTP, it was found that the incorporation rates of those of n=4 were markedly improved in comparison with those of n=1 from the comparison of the values of final bases. Further, it was also found that there was no substantial difference of the incorporation rate between that of n=1 and that of n=3 for XR-3'dCTP.

From the above, it can be seen that the incorporation rate of fluorescence-labeled 3'dNTP is markedly improved by using the value of n of 4 or higher. In other words, it can be seen that, by using them as terminators in methods for determining nucleotide sequences of DNA based on the chain termination method utilizing RNA polymerases, the nucleotide sequences of DNA can be determined with high sensitivity in short time by simple operation.

Reference Example 47
Synthesis of 6-trifluoroacetamido-1-hexene
1) Synthesis of 5-hexenyl-p-toluenesulfonate To an ice-cooled solution of p-toluenesulfonyl chloride (54.78 g, 287 mmol) in pyridine (100 ml), 5-hexen-1-ol (Tokyo Chemical Industry Co., Ltd., 20 ml, 239 mmol) was added dropwise, and stirred at 5° C. for 16 hours. The reaction mixture was poured into iced water (500 ml), and extracted with ether (500 ml). The ether layer was washed with cold 1N-hydrochloric acid, saturated aqueous sodium hydrogencarbonate and saturated saline, dried over magnesium sulfate, and concentrated under reduced pressure to afford 44.37 g of 5-hexenyl-p-toluenesulfonate (yield; 72.9%).

2) Synthesis of 6-iodo-1-hexene

A mixture of 5-hexenyl-p-toluenesulfonate (44.3 g, 174 mmol), sodium iodide (31.3 g, 209 mmol) and acetone (250 ml) was allowed to react under reflux for three hours. After cooling, the precipitates were removed by filtration, and the filtrate was concentrated. The resulting residue was dissolved in ether (500 ml), washed with saturated aqueous sodium hydrogensulfite, saturated aqueous sodium hydrogencarbonate and saturated saline, dried over magnesium sulfate, and concentrated under reduced pressure to afford 31.27 g of 6-iodo-1-hexene (yield; 85.5%).

3) Synthesis of 6-trifluoroacetamido-1-hexene

To a solution of sodium hydride (60% oil, 14.89 g, 372 mmol) in DMF (370 ml), trifluoroacetamido (50.39 g, 446 mmol) was added portionwise as about 10 portions with ice cooling. Subsequently, a solution of 6-iodo-1-hexene (31.27 g, 149 mmol) in DMF (130 ml) was added to the reaction mixture, and stirred at room temperature for three hours. The reaction mixture was added with saturated aqueous ammonium chloride (300 ml) and ether (300 ml) for extraction. The ether layer was washed twice with saturated saline (300 ml), dried over magnesium sulfate, and concentrated under reduced pressure, and the resulting residue was purified by silica gel column chromatography (eluent; hexane-ethyl acetate mixed solvent) to afford 24.36 g of 6-trifluoroacetamido-1-hexene (yield; 83.8%).

$^1$H-NMR (270 MHz, CDCl$_3$) δ ppm: 1.39–1.69 (m, 4H, —CH$_2$(CH$_2$)$_2$CH$_2$—), 2.04–2.14 (m, 2H, H$_2$C=C—), 3.37 (dd, 2H, J=7.0, 13.8 Hz, CH$_2$N), 4.96–5.06 (m, 2H, =CH CH$_2$), 5.71–5.86 (m, 1H, H$_2$C=CH), 6.45 (brs, 1H, NHTfa)

Reference Example 48
Synthesis of 3'-deoxy-5-(6"-trifluoroacetamido-1"-hexenyl) uridine (Compound 33)

A solution of palladium chloride (1.77 g, 10 mmol) and lithium chloride (0.85 g, 20 mmol) in methanol (100 ml) was stirred overnight to prepare 0.1 M solution of lithium tetrachloropalladate. 3'-Deoxyuridine (Compound 1, 1.14 g, 5 mmol) and mercury (II) acetate (1.60 g, 5 mmol) were dissolved in water (50 ml), and stirred at 60° C. for five hours. The reaction mixture was concentrated under reduced pressure, and the residue was suspended in anhydrous methanol (55 ml), add with the 0.1 M solution of lithium tetrachloropalladate prepared above (55 ml) and the 6-trifluoroacetamido-1-hexene obtained in Reference Example 47 (3.42 g, 17.5 mmol), and allowed to react under reflux for 16 hours. The reaction mixture was saturated with hydrogen sulfide gas, then the precipitates were removed by filtration through celite, and the filtrate was concentrated. The resulting residue was purified by silica gel column chromatography (eluent; dichloromethane-methanol mixed solution), and HPLC (column; Wakosil II 5C18 RS Prep, 20.0×250 mm, eluent; acetonitrile-water mixed solution) to afford 454 mg of a novel substance, 3'-deoxy-5-(6"-trifluoroacetamido-1"-hexenyl)uridine (Compound 33, yield; 21.6%).

$^1$H-NMR (270 MHz, DMSO-d$_6$) δ ppm: 1.25–1.55 (m, 4H, —(CH$_2$)$_2$—), 1.68–1.80 (m, 1H, 3'-Ha), 1.95–2.18 (m, 3H, 3'-Hb and =CHCH$_2$), 3.05–3.25(m, 2H, CH$_2$N), 3.50–3.60 (m, 1H, 5'-Ha), 3.70–3.85 (m, 1H, 5'-Hb), 4.15–4.36 (m, 2H, 2'-H and 4'-H), 5.22 (t, 1H, J=5.1 Hz, 5'-OH), 5.54 (d, 1H, J=4.3 Hz, 2'-OH), 5.66 (d, 1H, J=1.6 Hz, 1'-H), 6.03 (d, 1H, J=15.7 Hz, —CH=CHCH$_2$—), 6.38 (dt, 1H, J=7.0, 16.2 Hz, —CH=CHCH$_2$—), 8.18 (s, 1H, 6-H), 9.39 (brs, 1H, NHTfa), 11.32 (s, 1H, 3-NH)

Reference Example 49
Synthesis of 3'-deoxy-5-(6"-trifluoroacetamido-1"-hexenyl) uridine (Compound 33)

To a solution of 3'-deoxy-5-iodouridine (Compound 2, 300 mg, 0.85 mmol) in DMF (4.25 ml), the 6-trifluoroacetamido-1-hexene obtained in Reference Example 47 (496 mg, 2.54 mmol), cuprous (I) iodide (32.3 mg, 0.17 mmol), tetrakis(triphenylphosphine)palladium (0) (97.9 mg, 0.085 mmol), and triethylamine (0.24 ml, 1.69 mmol) were added, and allowed to react at 60° C. for 18 hours under nitrogen gas flow. The reaction mixture was diluted with a methylene chloride-methanol mixture (9.3 ml), added with ion exchange resin AG1X8 (Biolad, HCO$_3^-$ type, 0.68 g), and stirred for 30 minutes. After filtration of the reaction mixture, the filtrate was concentrated, and the resulting residue was purified by silica gel column chromatography (eluent; methylene chloride-methanol mixed solution), and HPLC (column; Wakosil II 5C18 RS Prep, 20.0×250 mm, eluent; acetonitrile-water mixed solution) to afford 127 mg of a novel substance, 3'-deoxy-5-(6"-trifluoroacetamido-1"-hexenyl)uridine (Compound 33, yield; 35.5%).

$^1$H-NMR (270 MHz, DMSO-d$_6$) δ ppm: 1.25–1.55 (m, 4H, —(CH$_2$)$_2$—), 1.68–1.80 (m, 1H, 3'-Ha), 1.95–2.18 (m, 3H, 3'-Hb and =CHCD$_2$), 3.05–3.25 (m, 2H, CH$_2$N), 3.50–3.60 (m, 1H, 5'-Ha), 3.70–3.85 (m, 1H, 5'-Hb), 4.15–4.36 (m, 2H, 2$^1$-H and 4'-H), 5.22 (t, 1H, J=5.1 Hz, 5'-OH), 5.54 (d, 1H, J=4.3 Hz, 2'-OH), 5.66 (d, 1H, J=1.6 Hz, 1'-H), 6.03 (d, 1H, J=15.7 Hz, —CH=CHCH$_2$—), 6.38 (dt, 1H, J=7.0, 16.2 Hz, —CH=CHCH$_2$—), 8.18 (s, 1H., 6-H), 9.39 (brs, 1H, NHTfa), 11.32 (s, 1H, 3-NH)

Reference Example 50
Synthesis of 5-(6"-amino-1"-hexenyl)-31 -deoxyuridine-5'-triphosphate (Compound 34)

3'-Deoxy-5-(6"-trifluoroacetamido1"-hexenyl)uridine (Compound 33, 126.4 mg, 0.3 mmol) was dissolved in triethyl phosphate (1.26 ml), cooled to −20° C., added with phosphorus oxychloride (41.9 μl), and stirred at −20° C. After 30 minutes, the reaction mixture was added with further phosphorus oxychloride (55.9 μl), and further stirred for 23 hours. This reaction mixture was added to 0.5 M solution of tris(tri-n-butylammonium)pyrophosphate in DMF (3.6 ml) cooled to −20° C., and stirred at room temperature for three hours. After the reaction was completed, the reaction mixture was added with a triethylamine-water mixture (15 ml), and left stand overnight. The reaction mixture was washed with ether, and purified by DEAE-Toyopearl ion exchange column chromatography (1.7×40 cm, eluent; triethylammonium hydrogencarbonate buffer (pH 7.5), 0 M→0.3 M linear gradient (total volume; 1 L)) . The purified product was added with 17% aqueous ammonia (60 ml), and left stand at 5° C. for 17 hours, and then concentrated under reduced pressure, and the obtained residue was purified again by DEAE-Toyopearl ion exchange column chromatography (1.7×40 cm, eluent; triethylammonium hydrogencarbonate buffer (pH 7.5), 0 M→0.3 M linear gradient (total volume; 1 L)) to afford 65.3 mg of a novel substance, 5-(6"-amino-1"-hexenyl)-3'-deoxyuridine-5'-triphosphate (Compound 34, yield; 22.4%).

Example 11
Synthesis of TMR-labeled 3'-deoxyuridine-5'-triphosphate (a compound of the general formula [I] where V is —CH=CH— and n=4)

To 5-(6"-amino-1"-hexenyl)-3'-deoxyuridine-5'-triphosphate (Compound 34, 14.8 μmol) dissolved in a mixture of DMF (300 μl) and water (300 μl), triethylamine (10 μl) and 6-carboxytetramethylrhodamine succinimide ester (Molecular Probe, 15.9 μmol) were added, and stirred at room temperature overnight. The reaction mixture was diluted with water (30 ml), and purified by DEAE-Toyopearl ion exchange column chromatography (1.7×15 cm, eluent; triethylammonium hydrogencarbonate buffer (pH 7.5), 0.05 M→0.65 M linear gradient (total volume; 1 L)) to afford 7.62 μmol (yield; 51.4%) of TMR-labeled 3'-deoxyuridine-5'-triphosphate represented by the following formula where the linker portion has a double bond and the number of n in the methylene chain is 4 [a compound of the general formula [I] where V is —CH=CH— and n=4, abbreviated as TMR-Allyl-3'dUTP(n4) hereinafter].

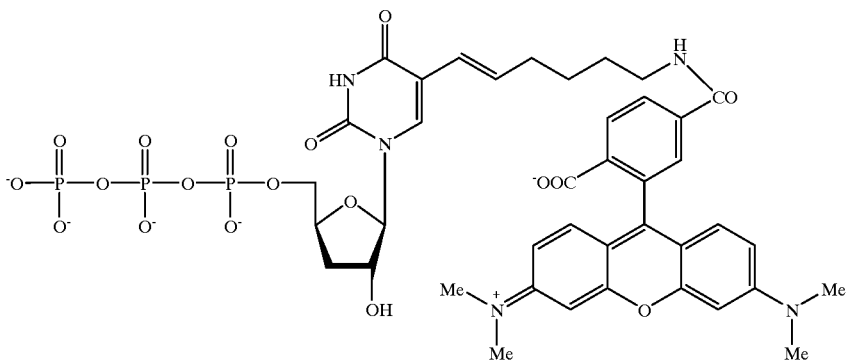

In the formula, Me represents a methyl group.

Figure 12:
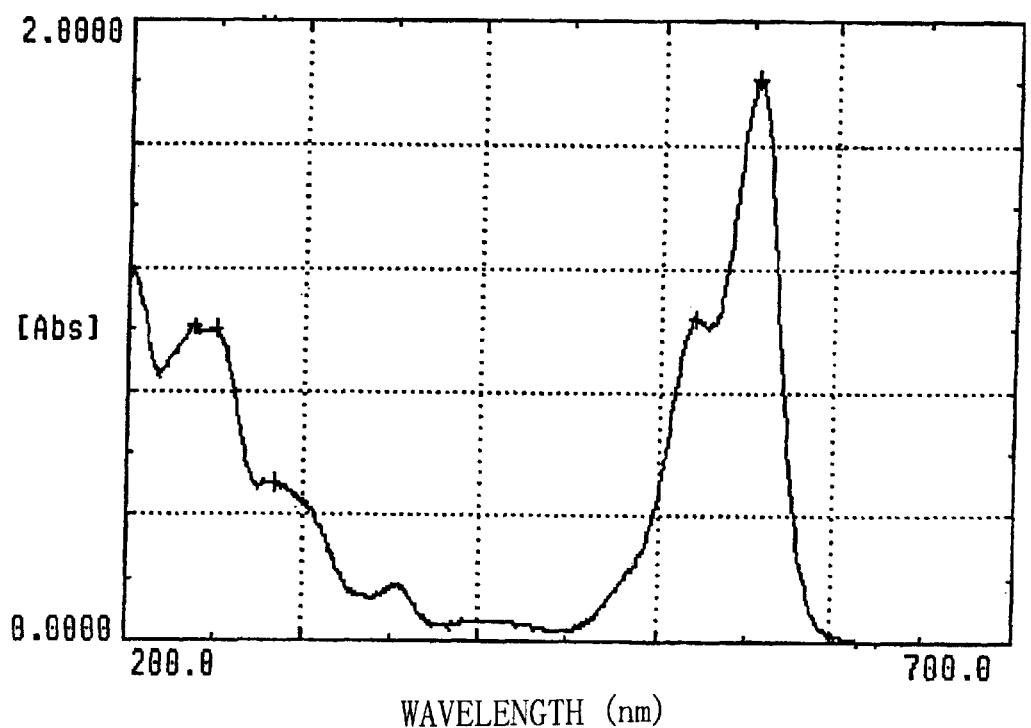
FIG. 12 shows the result of UV-visible region spectrophotometry of the carboxytetramethylrhodamine-labeled 3'-deoxyuridine-5'-triphosphate (a compound of the general formula [I] where V is —CH=CH— and n=4) obtained in Example 1

The absorption spectrum for UV-visible region resulting from spectrophotometry of the obtained TMR-Allyl-3'dUTP (n4) (measurement wavelength; 700 nm to 200 nm, reference; distilled water) performed by using DU640 UV-visible region spectrophotometer [Beckman] is shown in FIG. 12.

Experimental Example 2
Examination of 3'-deoxyterminators with different methylene chains as linker portion
[Template DNA]

PCR was performed by using the following materials (96° C. for one minute, 55° C. for 30 seconds, and 72° C. for one minute for one cycle, and 96° C. for 30 seconds, 55° C. for 30 seconds, 72° C. for one minute for 24 cycles), and the resulting PCR product (amplified DNA fragment of human thyroid stimulating hormone (TSH) βsubunit) was used as a template DNA.

Each material in a predetermined amount was added to a sample tube, filled up to a total volume of 10 μl with EXTaq buffer (Takara Shuzo), and used as a PCR mixture.
[Materials]

| | |
|---|---|
| • BluescriptII (Stratagene) introduced with human TSH β subunit DNA (accession No.S70586) | 1 pg |
| • Forward primer (5'-ACGTTGTAAAACGACGGCCAGT-3') | 0.1 M |
| • Reverse primer (5'-TAACAATTTCACAGGAAACA-3') | 0.1 M |

-continued

| | |
|---|---|
| • 2' dGTP | 200 μM |
| • 2' dTTP | 200 μM |
| • d' dATP | 200 μM |
| • EXTaq polymerase (Takara Shuzo) | 0.5 units |

[Terminator]

TMR-3'dUTP(n4) (the compound of Example 5)

TMR-Allyl-3'dUTP(n4) (the compound of Example 11)

[Experimental procedure]

The template DNA (10 ng) was added to a sample tube containing each of the terminators, guanosine-5'-triphosphate (rGTP), uridine-5'-triphosphate (rUTP), adenosine-5'-triphosphate (rATP), and cytidine-5'-triphosphate (rCTP), $MgCl_2$, spermidine-$(HCl)_3$, dithiothreitol (DTT), Tris/HCl (pH 7.5), yeast inorganic pyrophosphatase (PPase) and T7 RNA polymerase in such amounts as their final concentrations should be as follows, filled up to a total amount of 10 μl with distilled water, and used as a sample.

(Concentration)

| | |
|---|---|
| • Terminator | 10 μM |
| • rGTP | 500 μM |
| • rUTP | 500 μM |
| • rATP | 250 μM |
| • rCTP | 250 μM |
| • $MgCl_2$ | 5–10 mM |
| • Spermidine-$(HCl)_3$ | 2 mM |
| • DTT | 5 mM |
| • Tris/HCl (pH 7.5) | 40 mM |
| • Yeast PPase | 10 units |
| • T7 RNA polymerase (Gibco BRL) | 25 units |

After 30 minutes incubation of the sample at 37° C., the terminators not incorporated were removed by gel filtration using a Sephadex G25 column (Pharmacia), and the precipitates were collected by centrifugal separation. Subsequently, the precipitates were dissolved in 4 μl of formamide dye (10 mM EDTA containing 95% formamide), and heated to 90° C. for two minutes. After cooling, 2 μl of the solution was applied to 4% sequencing gel, and electrophoresed on ABI377 fluorescence automatic sequencer (ABI). The matrix-converted gel image (termination pattern) obtained in the sequencer with TMR-3'dUTP(n4) is shown in FIG. 13A, and the similarly matrix-converted gel image (termination pattern) obtained in the sequencer with TMR-Allyl-3 'dUTP(n4) is shown in FIG. 13B.

[Results]

Figure 13:
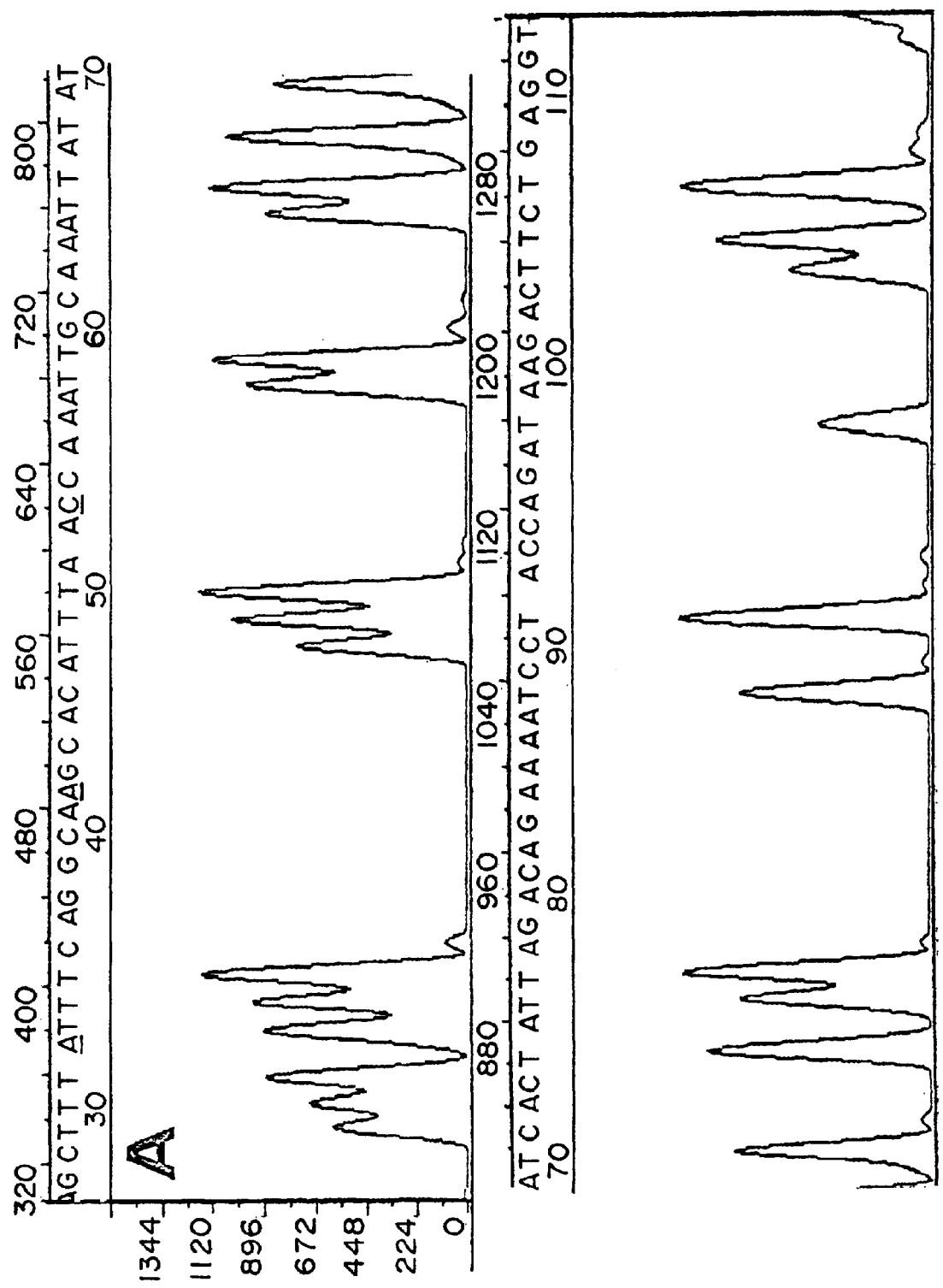
FIG. 13 shows the termination pattern obtained by using TMR-3'dUTP(n4) as the terminator (A), and the termination pattern obtained by using TMR-Allyl-3'dUTP(n4) as the terminator (B).
Figure 13:
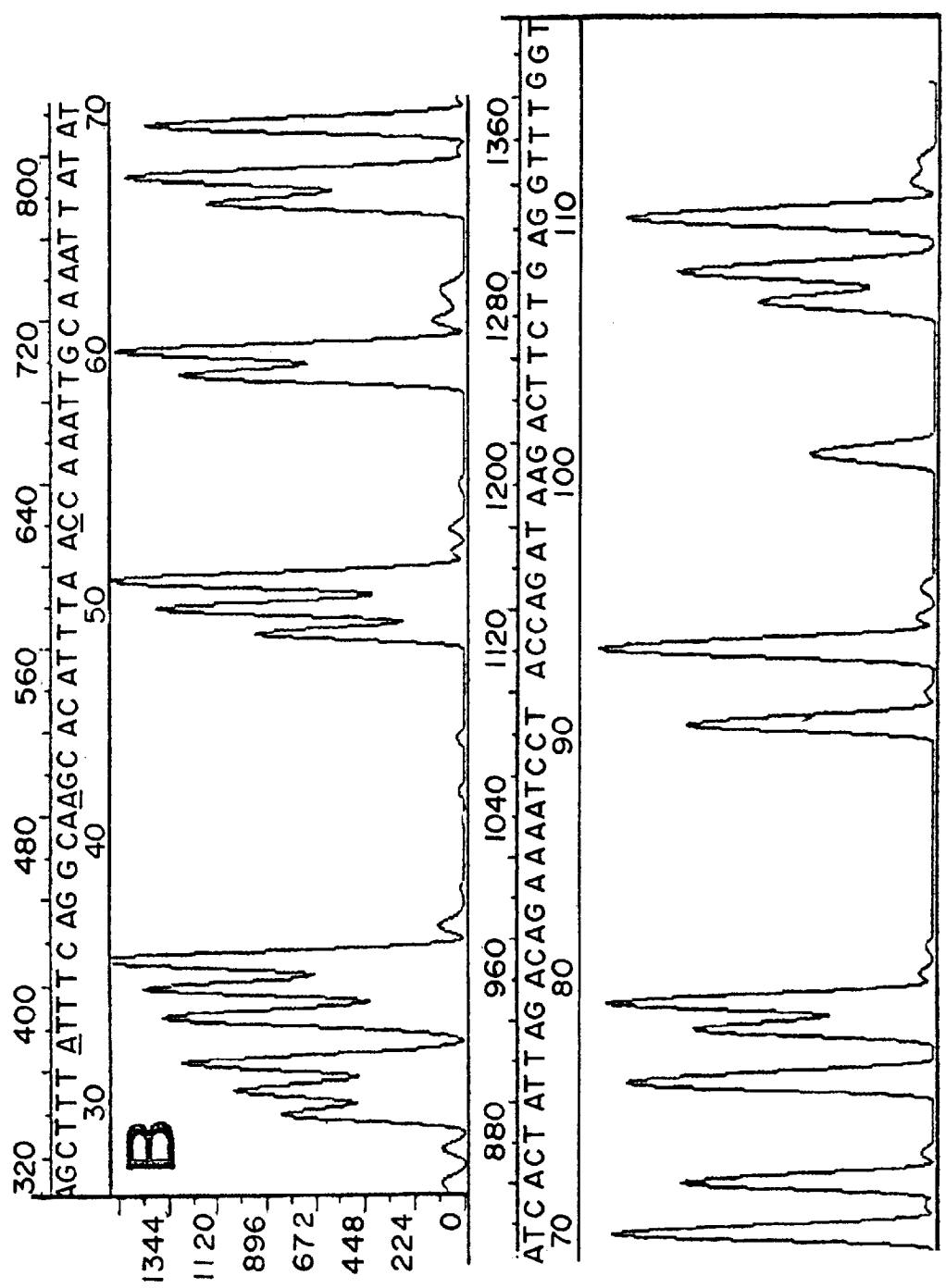

As clearly seen from FIGS. 13A and 13B, difference is not recognized between the termination patterns obtained with TMR-3'dUTP(n4) and TMR-Allyl-3'dUTP(n4), and therefore it was demonstrated that TMR-Allyl-3'dUTP(n4) is incorporated as efficiently as TMR-3'dUTP(n4).

Similar results were obtained when the experiment was repeated with the same conditions except that the amount of the terminator used was changed from 10 μM to 0.5 μM.

Reference Example 51

Synthesis of 3'-deoxy-5-(6"-trifluoroacetamido-1"-hexenyl) cytidine (Compound 35)

To a solution of 3'-deoxy-5-iodocytidine (Compound 6, 600 mg, 1.70 mmol) in DMF (8.5 ml), the 6-trifluoroacetamido-1-hexene obtained in Reference Example 47 (995 mg, 5.1 mmol), cuprous (I) iodide (64.7 mg, 0.34 mmol), tetrakis(triphenylphosphine)palladium (0) (196 mg, 0.17 mmol), and triethylamine (0.47 ml, 3.4 mmol) were added, and allowed to react at 60° C. for 18 hours under nitrogen gas flow. The reaction mixture was diluted with a methylene chloride-methanol mixture (20 ml), added with ion exchange resin AG1X8 (Biolad, $HCO_3^-$ type, 1.36 g), and stirred for 30 minutes. After filtration of the reaction mixture, the filtrate was concentrated, and the resulting residue was purified by silica gel column chromatography (eluent; methylene chloride-methanol mixed solution), and HPLC (column; Wakosil II 5C18 RS Prep, 20.0×250 mm, eluent; acetonitrile-water mixed solution) to afford 187 mg of a novel substance, 3'-deoxy-5-(6"-trifluoroacetamido-1"-hexenyl)cytidine (Compound 35, yield; 26.2%)

$^1$H-NMR (400 MHz, DMSO-$d_6$) δ ppm: 1.37–1.52 (m, 4H, —$(CH_2)_2$—), 1.64–1.68 (m, 1H, 3'-Ha), 1.90–1.97 (m, 1H, 3'-Hb), 2.07–2.12 (m, 2H, =CH$CH_2$), 3.18 (dd, 2H, J=6.8, 12.8 Hz, $CH_2$N), 3.53–3.56 (m, 1H, 5'-Ha), 3.80–3.82 (m, 1H, 5'-Hb), 4.10–4.30 (m, 2H, 2'-H and 4'-H), 5.15 (t, 1H, J=5.0 Hz, 5'-OH), 5.48 (d, 1H, J=4.0 Hz, 2'-OH), 5.65 (s, 1H, 1'-H), 5.87 (dt, 1H, J=6.8, 15.6 Hz, —CH=CHC$H_2$—), 6.18 (d, 1H, J=15.6 Hz, —CH=CHC$H_2$—), 6.91, 7.10 (2 br s, 2H, 4-$NH_2$), 8.26 (s, 1H, 6-H), 9.38 (brs, 1H, NHTfa)

Reference Example 52

Synthesis of 5-(6"-amino-1"-hexenyl)-3'-deoxycytidine-5'-triphosphate (Compound 36)

3'-Deoxy-5-(6"-trifluoroacetamido-1"-hexenyl)cytidine (Compound 35, 126.1 mg, 0.3 mmol) was dissolved in triethyl phosphate (1.26 ml), cooled to −20° C., added with phosphorus oxychloride (25.1 μl), and stirred at −20° C. After 30 minutes, the reaction mixture was added with further phosphorus oxychloride (22.3 μl), and further stirred for four hours. This reaction mixture was added to 0.5 M solution of tris(tri-n-butylammonium)pyrophosphate in DMF (3.6 ml) cooled to −20° C., and stirred at room temperature for three hours. After the reaction was completed, the reaction mixture was added with a triethylamine-water mixture (5 ml), and left stand overnight. The reaction mixture was washed with ether, and purified by DEAE-Toyopearl ion exchange column chromatography (1.7×40 cm, eluent; triethylammonium hydrogencarbonate buffer (pH 7.5), 0 M→0.3 M linear gradient (total volume; 1 L)). The purified product was added with 17% aqueous ammonia (60 ml), and left stand at 5° C. for 15 hours, and then concentrated under reduced pressure, and the obtained residue was purified again by DEAE-Toyopearl ion exchange column chromatography (1.7×40 cm, eluent; triethylammonium hydrogencarbonate buffer (pH 7.5), 0 M→0.3 M linear gradient (total volume; 1 L)) to afford 175 mg of a novel substance, 5-(6"-amino-1"-hexenyl)-3'-deoxycytidine -5'-triphosphate (Compound 36, yield; 60.2%).

Example 12

Synthesis of XR-labeled 3'-deoxycytidine-5'-triphosphate (a compound of the general formula [I] where V is —CH=CH— and n=4)

To 5-(6"-amino-1"-hexenyl)-3'-deoxycytidine-5'-triphosphate (Compound 36, 10 μmol) dissolved in a mixture of DMF (300 μl) and water (300 μl), triethylamine (10 μl) and 6-carboxy-X-rhodamine succinimide ester (Molecular Probe, 25 μmol) were added, and stirred at room temperature overnight. The reaction mixture was diluted with water (30 ml), and purified by DEAE-Toyopearl ion exchange column chromatography (1.7×15 cm, eluent; triethylammonium hydrogencarbonate buffer (pH 7.5), 0.05 M→0.65 M linear gradient (total volume; 1 L)) to afford 6.55 μmol (yield; 65.5%) of XR-labeled 3'-deoxycytidine-5-triphosphate represented by the following formula where the linker portion has a double bond and the number of n in the methylene chain is 4 [a compound of the general formula [I] where V is —CH=CH— and n=4, abbreviated as XR-Allyl-3'dCTP(n4) hereinafter].

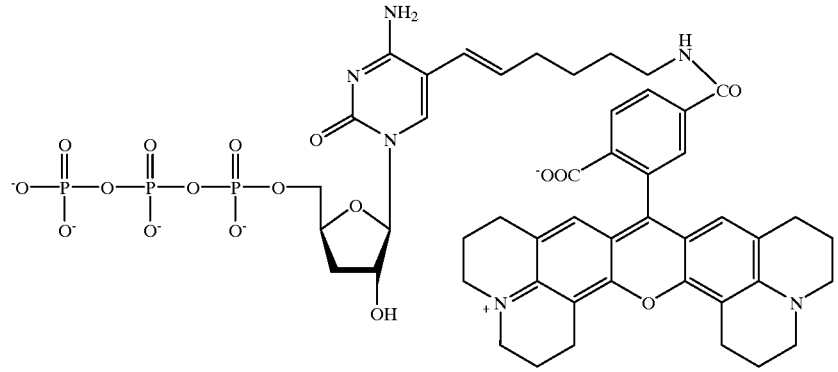

Figure 14:
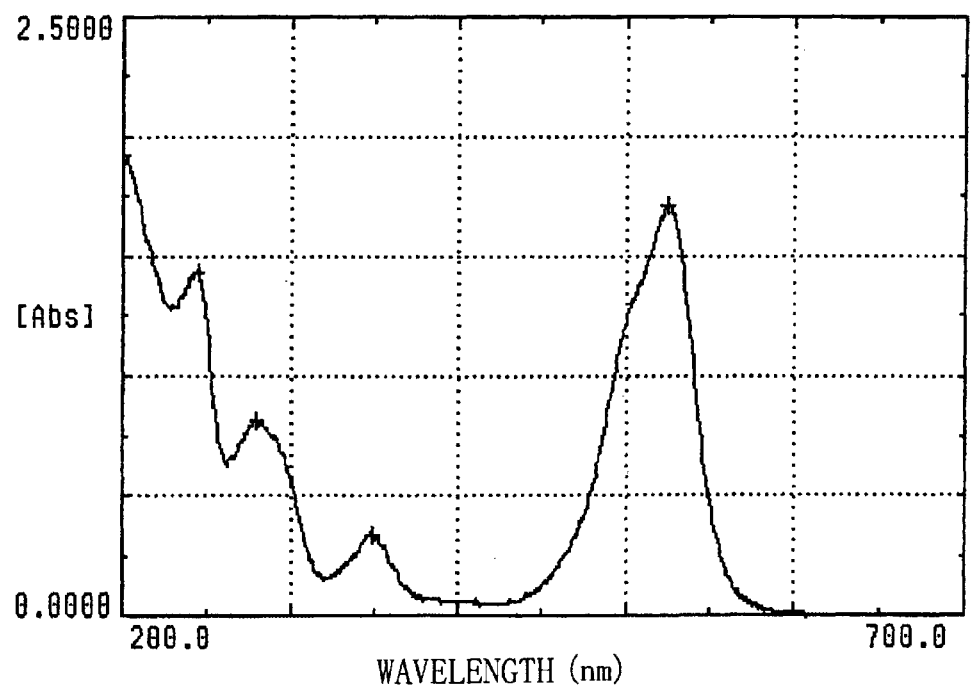
FIG. 14 shows the result of UV-visible region spectrophotometry of the carboxyrhodamine-X-labeled 3'-deoxycytidine-5'-triphosphate (a compound of the general formula [I] where V is —CH=CH— and n=4) obtained in Example 12.

The absorption spectrum for UV-visible region resulting from spectrophotometry of the obtained XR-Allyl-3'dCTP (n4) (measurement wavelength; 700 nm to 200 nm, reference; distilled water) performed by using DU640 UV-visible region spectrophotometer [Beckman] is shown in FIG. 14.

Reference Example 53
Synthesis of 7-(6"-trifluoroacetamido-1"-hexenyl)-3'-deoxy-7-deazaadenosine (Compound 37)

To a solution of 7-iodo-3'-deoxy-7-deazaadenosine (Compound 18, 600 mg, 1.60 mmol) in DMF (8.0 ml), the 6-trifluoroacetamido-1-hexene obtained in Reference Example 47 (912 mg, 4.80 mmol), cuprous (I) iodide (62 mg, 0.32 mmol), tetrakis(triphenylphosphine)palladium (0) (184 mg, 0.16 mmol), and triethylamine (0.44 ml, 3.2 mmol) were added, and allowed to react at 60 °C. for 18 hours under nitrogen gas flow. The reaction mixture was diluted with a methylene chloride-methanol mixture (16 ml), added with ion exchange resin AG1X8 (Biolad, $HCO_3^-$ type, 1.50 g), and stirred for 30 minutes. After filtration of the reaction mixture, the filtrate was concentrated, and the resulting residue was purified by silica gel column chromatography (eluent; methylene chloride-methanol mixed solution), and HPLC (column; Wakosil II 5C18 RS Prep, 20.0×250 mm, eluent; acetonitrile-water mixed solution) to afford 175 mg of a novel substance, 7-(6"-trifluoroacetamido-1"-hexenyl)-3'-deoxy-7-deazaadenosine (Compound 37, yield; 24.8%).

$^1$H-NMR (400 MHz, DMSO-$d_6$) δ ppm: 1.23–1.54 (m, 4H, —(CH$_2$)$_2$—), 1.87–1.90 (m, 1H, 3'-Ha), 2.19–2.20 (m, 3H, 3'-Hb and =CHCH$_2$), 3.20 (dd, 2H, J=6.6, 13.0 Hz, CH$_2$N), 3.46–3.62 (m, 2H, 5'-Ha and 5'-Hb), 4.25–4.38 (m, 2H, 2'-H and 4'-H), 5.01 (t, 1H, J=5.6 Hz, 5'-OH), 5.50 (d, 1H, J=4.8 Hz, 2'-OH), 5.95 (dt, 1H, J=7.2, 15.2 Hz, —CH=CHCH$_2$—), 6.01 (d, 1H, J=2.4 Hz, 1'-H), 6.62 (br s, 2H, 6-NH2), 6.74 (d, 1H, J=15.2 Hz, —CH=CHCH$_2$—), 7.48 (s, 1H, 8-H), 8.03 (s, 1H, 2-H), 9.40 (brs, 1H, NHTfa)

Reference Example 54
Synthesis of 7-(6"-amino-1"-hexenyl)-3'-deoxy-7-deazaadenosine-5'-triphosphate (Compound 38)

7-(6"-trifluoroacetamido-1"-hexenyl)-3'-deoxy-7-deazaadenosine (Compound 37, 133 mg, 0.3 mmol) was dissolved in triethyl phosphate (1.26 ml), cooled to −20° C., added with phosphorus oxychloride (25.1 μl), and stirred at −20° C. After 30 minutes, the reaction mixture was added with further phosphorus oxychloride (22.3 μl), and further stirred for six hours. This reaction mixture was added to 0.5 M solution of tris(tri-n-butylammonium)pyrophosphate in DMF (3.6 ml) cooled to −20° C., and stirred at room temperature for three hours. After the reaction was completed, the reaction mixture was added with a triethylamine-water mixture (5 ml), and left stand overnight. The reaction mixture was washed with ether, and purified by DEAE-Toyopearl ion exchange column chromatography (1.7×40 cm, eluent; triethylammonium hydrogencarbonate buffer (pH 7.5), 0 M→0.3 M linear gradient (total volume; 1 L)). The purified product was added with 17% aqueous ammonia (60 ml), and left stand at 5° C. for 15 hours, and then concentrated under reduced pressure, and the obtained residue was purified again by DEAE-Toyopearl ion exchange column chromatography (1.7×40 cm, eluent; triethylammonium hydrogencarbonate buffer (pH 7.5), 0 M→0.3 M linear gradient (total volume; 1 L)) to afford 126 mg of a novel substance, 7-(6"-amino-1"-hexenyl)-3'-deoxy-7-deazaadenosine-5'-triphosphate (Compound 38, yield; 42.2%).

Example 13
Synthesis of R6G-labeled 3'-deoxy-7-deazaadenosine-5'-triphosphate (a compound of the general formula [I] where V is —CH=CH— and n=4)

To 7-(6"-amino-1"-hexenyl)-3'-deoxy-7-deazaadenosine-5'-triphosphate (Compound 38, 8 μmol) dissolved in a mixture of DMF (2 ml) and water (1 ml), triethylamine (10 μl) and 5-carboxyrhodamine 6G succinimide ester (Molecular Probe, 16 μmol) were added, and stirred at room temperature overnight. The reaction mixture was diluted with water (30 ml), and purified by DEAE-Toyopearl ion exchange column chromatography (1.7×15 cm, eluent; triethylammonium hydrogencarbonate buffer (pH 7.5), 0.05 M→0.65 M linear gradient (total volume; 1 L)) to afford 3.90 μmol (yield; 48.7%) of R6G-labeled 3'-deoxy-7-deazaadenosine-5'-triphosphate represented by the following formula where the linker portion has a double bond and the number of n in the methylene chain is 4 [a compound of the general formula [I] where V is —CH=CH— and n=4, abbreviated as R6G-Allyl-3'dATP(n4) hereinafter].

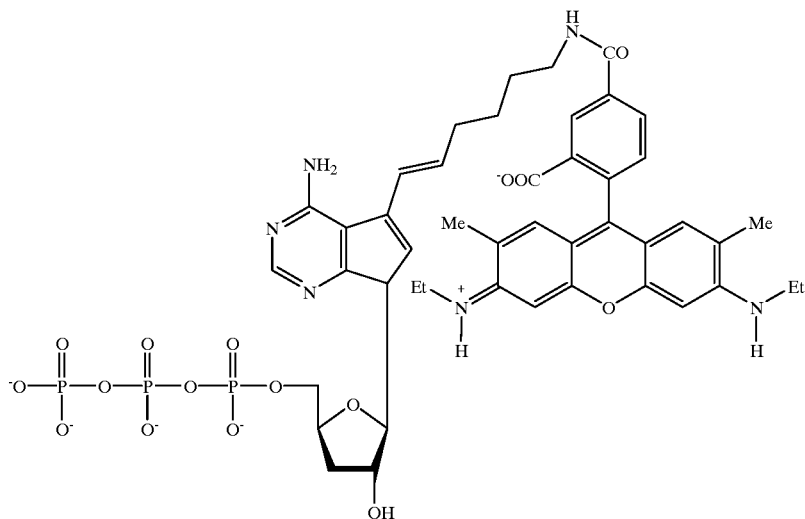

In the formula, Et represents an ethyl group, and Me represents a methyl group.

Figure 15:
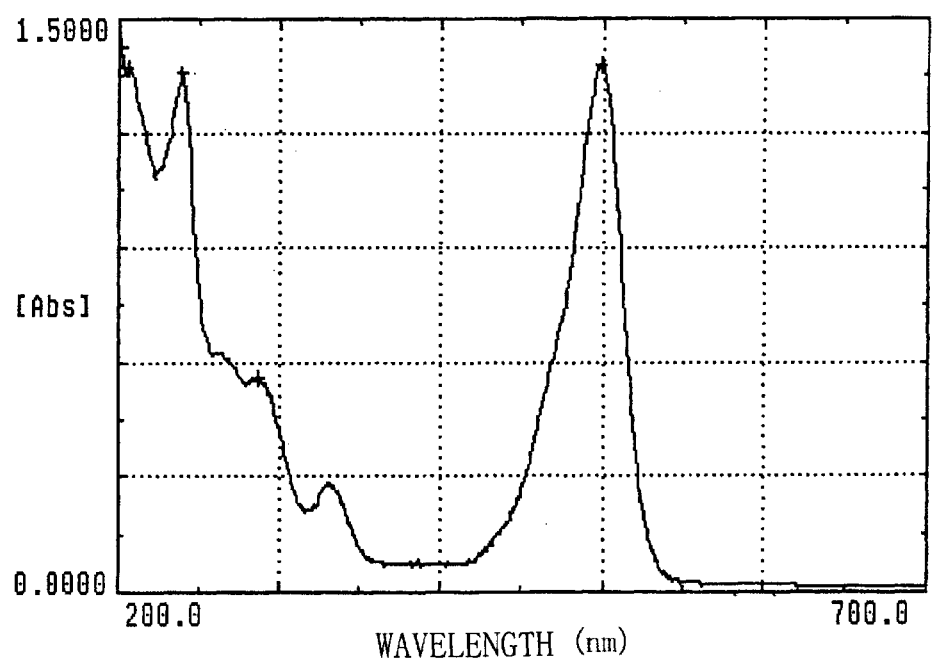
FIG. 15 shows the result of UV-visible region spectrophotometry of the carboxyrhodamine-6G-labeled 3'-deoxy-7-deazaadenosine-5'-triphosphate (a compound of the general formula [I] where V is —CH=CH— and n=4) obtained in Example 13.

The absorption spectrum for UV-visible region resulting from spectrophotometry of the obtained R6G-Allyl-3'dATP (n4) (measurement wavelength; 700 nm to 200 nm, reference; distilled water) performed by using DU640 UV-visible region spectrophotometer [Beckman] is shown in FIG. 15.

Reference Example 55
Synthesis of 7-(6"-trifluoroacetamido-1"-hexenyl)-3'-deoxy-7-deazaguanosine (Compound 39)

To a solution of 7-iodo-3'-deoxy-7-deazaguanosine (Compound 30, 1.31 g, 3.33 mmol) in DMF (16.67 ml), the 6-trifluoroacetamido1-hexene obtained in Reference Example 47 (1.90 g, 9.99 mmol), cuprous (I) iodide (130 mg, 0.66 mmol), tetrakis(triphenylphosphine)palladium (0) (385 mg, 0.33 mmol), and triethylamine (0.93 ml, 6.66 mmol) were added, and allowed to react at 60° C. for 18 hours under nitrogen gas flow. The reaction mixture was diluted with a methylene chloride-methanol mixture (40 ml), added with ion exchange resin AG1X8 (Biolad, $HCO_3^-$ type, 2.96 g), and stirred for 30 minutes. After filtration of the reaction mixture, the filtrate was concentrated, and the resulting residue was purified by silica gel column chromatography (eluent; methylene chloride-methanol mixed solution), and HPLC (column; Wakosil II 5C18 RS Prep, 20.0× 250 mm, eluent; acetonitrile-water mixed solution) to afford 439 mg of a novel substance, 3'-deoxy-7-(6"-trifluoroacetamido-1"-hexenyl)-7-deazaguanosine (Compound39, yield; 28.7%).

$^1$H-NMR (400 MHz, DMSO-$d_6$) δ ppm: 1.35–1.53 (m, 4H, —(CH$_2$)$_2$—), 1.85–1.89 (m, 1H, 31-Ha), 2.09–2.15 (m, 3H, 3'-Hb and =CHCCH$_2$), 3.19 (dd, 2H, J=6.8, 12.8 Hz, CH$_2$N), 3.43–3.56 (m, 2H, 5'-Ha and 5'-Hb), 4.10–4.30 (m, 2H, 2'-H and 4'-H), 4.84 (t, 1H, J=5.6 Hz, 5'-OH), 5.42 (d, 1H, J=4.4 Hz, 2'-OH), 5.81 (d, 1H, J=2.8 Hz, 1'-H), 6.21 (br s, 2H, 2-NH$_2$), 6.37 (d, 1H, J=15.6 Hz, —C<u>H</u>=CHCH$_2$—), 6.57 (dt, 1H, J=7.1, 15.6 Hz, —CH=C<u>H</u>CH$_2$—), 6.93 (s, 1H, 8-H), 9.39 (brs, 1H, NHTfa), 10.29 (s, 1H, 1-H)

Reference Example 56
Synthesis of 7-(6"-amino-1"-hexenyl)-3'-deoxy-7-deazaguanosine-5'-triphosphate (Compound 40)

7-(6"-Trifluoroacetamido-1b"-hexenyl)-3'-deoxy-7-deazaguanosine (Compound 39, 138 mg, 0.3 mmol) was dissolved in triethyl phosphate (1.26 ml), cooled to −20° C., added with phosphorus oxychloride (25.1 μl), and stirred at −20° C. After 30 minutes, the reaction mixture was added with further phosphorus oxychloride (22.3 μl), and further stirred for 8 hours. This reaction mixture was added to 0.5 M solution of tris(tri-n-butylammonium)pyrophosphate in DMF (3.6 ml) cooled to −20 ° C., and stirred at room temperature for three hours. After the reaction was completed, the reaction mixture was added with a triethylamine-water mixture (5 ml), and left stand overnight. The reaction mixture was washed with ether, and purified by DEAE-Toyopearl ion exchange column chromatography (1.7×40 cm, eluent; triethylammonium hydrogencarbonate buffer (pH 7.5), 0 M→0.3 M linear gradient (total volume; 1 L)). The purified product was added with 17% aqueous ammonia (60 ml), left stand at 5° C. for 16 hours, and then concentrated under reduced pressure, and the obtained residue was purified again by DEAE-Toyopearl ion exchange column chromatography (1.7×40 cm, eluent; triethylammonium hydrogencarbonate buffer (pH 7.5), 0 M→0.3 M linear gradient (total volume; 1 L)) to afford 122 mg of a novel substance, 7-(6"-amino-1"-hexenyl)-3'-deoxy-7-deazaguanosine-5'-triphosphate (Compound 40, yield; 40.4%).

Example 14
Synthesis of R110-labeled 3'-deoxy-7-deazaguanosine-5'-triphosphate (a compound of the general formula [I] where V is —CH=CH— and n=4)

To 7-(6"-amino-1"-hexenyl)-3'-deoxy-7-deazaguanosine-5'-triphosphate (Compound 40, 10 μmol) dissolved in a mixture of DMF (500 μl) and water (375 μl), triethylamine (25 μl) and 5-carboxyrhodamine-110-bis(trifluoroacetate) succinimide ester (Molecular Probe, 25 μmol) were added, and stirred at room temperature overnight. The reaction mixture was diluted with water (30 ml), and purified by DEAE-Toyopearl ion exchange column chromatography (1.7×15 cm, eluent; triethylammonium hydrogencarbonate buffer (pH 7.5), 0.05 M→0.65 M linear gradient (total volume; 1 L)) to afford 5.1 μmol (yield; 51.0%) of R110-labeled 3'-deoxy-7-deazaguanosine-5'-triphosphate represented by the following formula where the linker portion has a double bond and the number of n in the methylene chain is 4 [a compound of the general formula [I] where V is —CH=CH— and n=4, abbreviated as R110-Allyl-3'dGTP (n4) hereinafter].

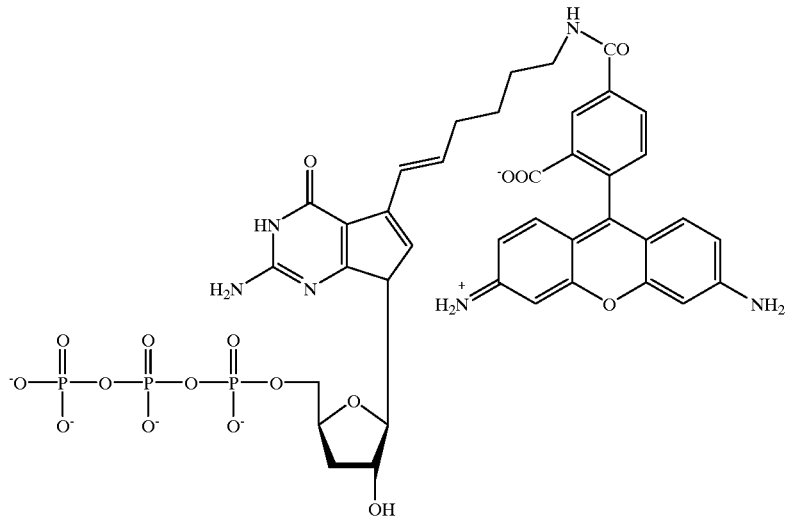

Figure 16:
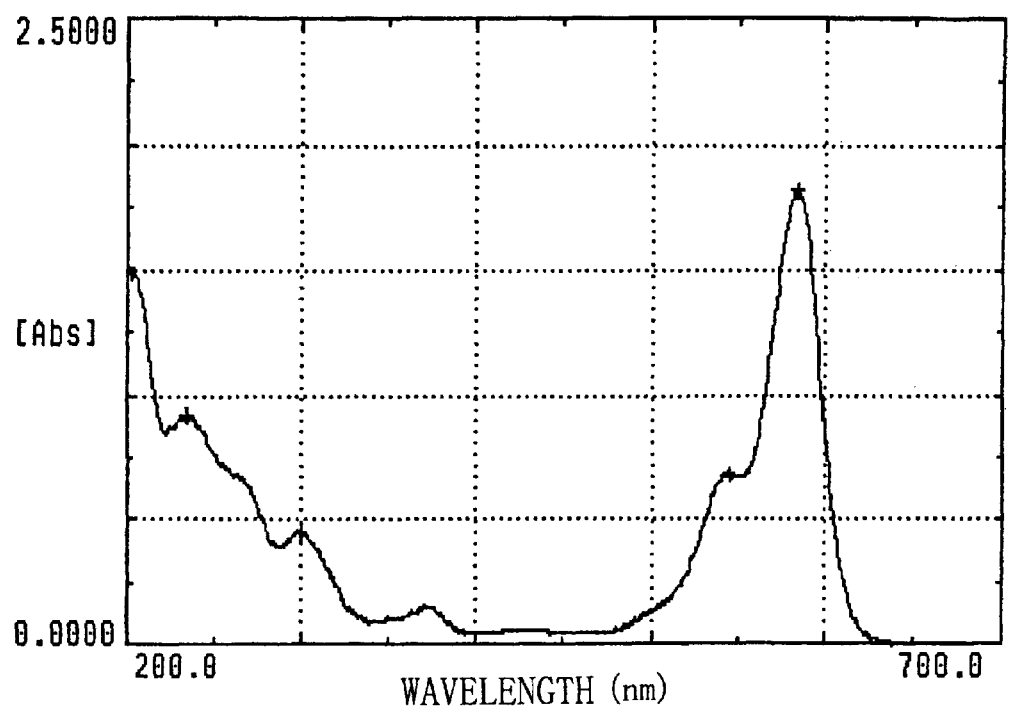
FIG. 16 shows the result of UV-visible region spectrophotometry of the carboxyrhodamine-110-labeled 3'-deoxy-7-deazaguanosine-5'-triphosphate (a compound of the general formula [I] where V is —CH=CH— and n=4) obtained in Example 14.

The absorption spectrum for UV-visible region resulting from spectrophotometry of the obtained R110-Allyl-3'dGTP (n4) (measurement wavelength; 700 nm to 200 nm, reference; distilled water) performed by using DU640 UV-visible region spectrophotometer [Beckman] is shown in FIG. 16.

As described above, the present invention provides fluorescence-labeled 3'-deoxyribonucleotide derivatives that are useful for safely determining target nucleotide sequences with high sensitivity in, for example, nucleic acid sequencing methods utilizing RNA polymerase activity. The fluorescence-labeled 3'-deoxyribonucleotide derivatives of the present invention provide notable advantage that target nucleotide sequences can be determined more accurately and more rapidly by a simple procedure in short time, when they are used in the chain termination methods utilizing RNA polymerases. Therefore, the present invention will make great contribution to the field.

What we claim is:

1. A 3'-deoxyribonucleotide derivative represented by the following general formula [I]:

Q—V—(CH$_2$)$_n$—NH—R   [I]

wherein Q represents a 3'-deoxyribonucleotide residue, n represents an integer not less than 4, V represents —C≡C— or —CH=CH—, and R represents a fluorescent group.

2. The 3'-deoxyribonucleotide derivative of claim 1, wherein n represents an integer of 4–10.

3. The 3'-deoxyribonucleotide derivative of claim 1, wherein n represents an integer of 4–8.

4. The 3'-deoxyribonucleotide derivative of claim 1, wherein n represents 4 or 6.

5. The 3'-deoxyribonucleotide derivative of the claim 1, wherein R is represented by the following general formula [VII]:

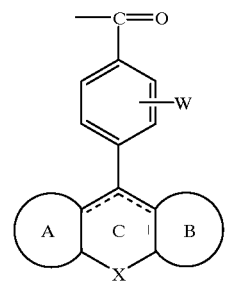   [VII]

wherein W represents a carboxyl group, X represents —O—, —S—, —NR'— where R' represents hydrogen atom, a lower alkyl group, an aralkyl group or an aryl group, or —CH$_2$—, one of the ring A and the ring B represents

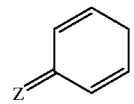

and the other one represents

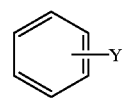

where Z represents O or =N$^+$R$_1$R$_2$, and Y represents OH or —NR$_1$R$_2$ where R$_1$ and R$_2$ each independently represent hydrogen atom or a lower alkyl group, or both of R$_1$ and R$_2$ represent a trimethylene group (provided that R$_1$ and R$_2$ represent two trimethylene groups, of which other end is bonded to either one of the carbon atoms next to the nitrogen atom to which the trimethylene group is bonded, the broken line — — — — — — in the ring C:

represents a bond present at a position decided by the structures of the ring A and the ring B, and the rings A, B and C and the benzene ring having W may optionally have one or more additional substituents.

6. The 3'-deoxyribonucleotide derivative of claim 5, wherein X is —O—.

7. The 3'-deoxyribonucleotide derivative of claim 6, wherein Z represents $=N^+R_1R_2$, and Y represents $—NR_1R_2$.

8. The 3'-deoxyribonucleotide derivative of claim 7, wherein $R_1$ and $R_2$ each independently represent hydrogen atom or a lower alkyl group having 1 to 6 carbon atoms, or both of $R_1$ and $R_2$ represent a trimethylene group.

9. The 3'-deoxyribonucleotide derivative of claim 8, wherein at least one of the rings A, B and C and the benzene ring having W has one or more lower alkyl group having 1 to 6 carbon atoms as additional substituents.

10. The 3'-deoxyribonucleotide derivative of claim 7, wherein at least one of the rings A, B and C and the benzene ring having W has one or more lower alkyl group having 1 to 6 carbon atoms as additional substituents.

11. The 3'-deoxyribonucleotide derivative of claim 6, wherein at least one of the rings A, B and C and the benzene ring having W has one or more lower alkyl group having 1 to 6 carbon atoms as additional substituents.

12. The 3'-deoxyribonucleotide derivative of claim 5, wherein Z represents $=N^+R_1R_2$, and Y represents $—NR_1R_2$.

13. The 3'-deoxyribonucleotide derivative of claim 12, wherein $R_1$ and $R_2$ each independently represent hydrogen atom or a lower alkyl group having 1 to 6 carbon atoms, or both of $R_1$ and $R_2$ represent a trimethylene group.

14. The 3'-deoxyribonucleotide derivative of claim 13, wherein at least one of the rings A, B and C and the benzene ring having W has one or more lower alkyl group having 1 to 6 carbon atoms as additional substituents.

15. The 3'-deoxyribonucleotide derivative of claim 12, wherein at least one of the rings A, B and C and the benzene ring having W has one or more lower alkyl group having 1 to 6 carbon atoms as additional substituents.

16. The 3'-deoxyribonucleotide derivative of claim 5, wherein at least one of the rings A, B and C and the benzene ring having W has one or more lower alkyl group having 1 to 6 carbon atoms as additional substituents.

17. The 3'-deoxyribonucleotide derivative of claim 5, wherein V is —CH=CH—.

18. The 3'-deoxyribonucleotide derivative of claim 5, wherein V is —C≡C—.

19. The 3'-deoxyribonucleotide derivative of claim 1, wherein V is —CH=CH—.

20. The 3'-deoxyribonucleotide derivative of claim 1, wherein V is —C≡C—.

21. A terminator composed of the 3'-deoxyribonucleotide derivative of claim 1, which is used for methods for determining nucleotide sequences utilizing RNA polymerases.

* * * * *

UNITED STATES PATENT AND TRADEMARK OFFICE
CERTIFICATE OF CORRECTION

PATENT NO. : 6,265,569 B1  
DATED : July 24, 2001  
INVENTOR(S) : Yoshihide Hayashizaki, Kaori Ozawa, Kazunari Fujio and Takumi Tanaka It is certified that error appears in the above-identified patent and that said Letters Patent is hereby corrected as shown below:

<u>Title page,</u>  
Item [73], after the first named Assignee "The Institute of Physical and Chemical Research (JP)" please add the following second Assignee -- Wako Pure Chemical Industries Ltd. (JP) --.

Signed and Sealed this

Fifth Day of February, 2002

Attest:

JAMES E. ROGAN  
*Attesting Officer*     *Director of the United States Patent and Trademark Office*